US012064432B2

(12) United States Patent
Reaume et al.

(10) Patent No.: US 12,064,432 B2
(45) Date of Patent: *Aug. 20, 2024

(54) TREATMENT OF ADIPOCYTES

(71) Applicants: Melior Pharmaceuticals I, Inc., Exton, PA (US); Board Of Supervisors Of Louisiana State University And Agricultural And Mechanical College, Baton Rouge, LA (US)

(72) Inventors: Andrew G. Reaume, Exton, PA (US); Weina Cong, Exton, PA (US); Frank Greenway, Baton Rouge, LA (US); Ann Coulter, Baton Rouge, LA (US)

(73) Assignees: Melior Pharmaceuticals I, Inc., Exton, PA (US); Board Of Supervisors Of Louisiana State University And Agricultural And Mechanical College, Baton Rouge, LA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/993,216

(22) Filed: Nov. 23, 2022

(65) Prior Publication Data

US 2023/0149404 A1    May 18, 2023

Related U.S. Application Data

(63) Continuation of application No. 16/997,447, filed on Aug. 19, 2020, now Pat. No. 11,534,442, which is a continuation of application No. 15/948,406, filed on Apr. 9, 2018, now Pat. No. 10,786,503.

(60) Provisional application No. 62/483,584, filed on Apr. 10, 2017.

(51) Int. Cl.
*A61K 31/513*    (2006.01)
*A61K 31/045*    (2006.01)

(52) U.S. Cl.
CPC .......... *A61K 31/513* (2013.01); *A61K 31/045* (2013.01)

(58) Field of Classification Search
CPC ....... A61K 31/045; A61K 31/513; A61P 3/00; A61P 3/04; A61P 3/10
See application file for complete search history.

(56) References Cited

U.S. PATENT DOCUMENTS

| | | |
|---|---|---|
| 3,174,901 A | 3/1965 | Sterne |
| 3,922,345 A | 11/1975 | Lipinski et al. |
| 4,080,454 A | 3/1978 | Lipinski |
| 4,824,851 A | 4/1989 | Takaya et al. |
| 5,476,855 A | 12/1995 | el Kouni et al. |
| 5,698,155 A | 12/1997 | Grosswald et al. |
| 5,721,114 A | 2/1998 | Abrahamsen et al. |
| 5,721,241 A | 2/1998 | el Kouni et al. |
| 6,004,925 A | 12/1999 | Dasseux et al. |
| 6,037,323 A | 3/2000 | Dasseux et al. |
| 6,410,255 B1 | 6/2002 | Pollok et al. |
| 7,429,564 B2 | 9/2008 | Arbit et al. |
| 7,776,870 B2 | 8/2010 | Reaume et al. |
| 8,343,985 B2 | 1/2013 | Reaume et al. |
| 8,835,448 B2 | 9/2014 | Reaume et al. |
| 9,216,959 B2 | 12/2015 | Reaume et al. |
| 10,251,883 B2 | 4/2019 | Reaume et al. |
| 10,786,503 B2 | 9/2020 | Reaume et al. |
| 11,033,548 B2 | 6/2021 | Reaume et al. |
| 11,534,442 B2 | 12/2022 | Reaume et al. |
| 2002/0151497 A1 | 10/2002 | Ben-Sasson |
| 2005/0009817 A1 | 1/2005 | Savoy et al. |
| 2005/0208054 A1 | 9/2005 | Czech et al. |
| 2006/0024365 A1 | 2/2006 | Vaya et al. |
| 2006/0035302 A1 | 2/2006 | Lee |
| 2006/0252777 A1 | 11/2006 | Kim et al. |
| 2007/0025953 A1 | 2/2007 | Jones |
| 2007/0049609 A1 | 3/2007 | Broka et al. |
| 2007/0093516 A1 | 4/2007 | Reaume et al. |
| 2007/0185070 A1 | 8/2007 | Pershadsingh |
| 2010/0004273 A1 | 1/2010 | Reaume et al. |
| 2010/0278804 A1 | 11/2010 | Reaume et al. |
| 2012/0046244 A1 | 2/2012 | Rogers et al. |

FOREIGN PATENT DOCUMENTS

| | | |
|---|---|---|
| CN | 1395560 | 2/2003 |
| EP | 1541694 | 6/2005 |
| GB | 1377308 | 12/1974 |
| JP | 2007037546 | 2/2007 |
| WO | 199401414 | 1/1994 |
| WO | 200151463 | 7/2001 |

(Continued)

OTHER PUBLICATIONS

Advisory Action dated Apr. 13, 2012 received in co-pending U.S. Appl. No. 12/837,067.
Blasioli et al., "Lyn/CD22/SHP-1 and their importance in autoimmunity", Curr Dir Autoimmun, 2002, 5, pp. 151-160.
Bozulic et al., "The influence of Lyn mkinase on Na, K-ATPase in porcine lens epithelium", Am J Physiol Cell Physiol, 2003, 286(1), pp C90-6.
Briggs et al., "Affinity of Src Family Kinase SH3 Domains for HIV Nef in vitro Does not Predict Kinase Activation by Nef in vivo", Biochemistry, 2000; 39, pp. 489-495.
Buchwald et al., "Long-term, continuous intravenous heparin administration by an implantable infusion pump in ambulatory patients with recurrent venous thrombosis", Surgery, 1987; 88(4), pp. 507-516.

(Continued)

*Primary Examiner* — Umamaheswari Ramachandran
(74) *Attorney, Agent, or Firm* — Armstrong Teasdale LLP

(57) ABSTRACT

The present disclosure provides compositions comprising a lyn kinase activator and TRPM8 agonist, and to methods of: reducing blood glucose levels, weight gain, or fat depot levels; treating metabolic syndrome, Syndrome X, obesity, prediabetes, type II diabetes, type I diabetes; treating hypercholesterolemia, hypertension, coronary heart disease, diabetic neuropathy, lipodystrophy, diabetic retinopathy, erectile dysfunction, kidney disease, dyslipidemia, dyslipoproteinemia, a peroxisome proliferator activated receptor-associated disorder, septicemia, a thrombotic disorder, or pancreatitis; inducing the beiging of adipocytes; and preventing pancreatic beta cell degeneration.

4 Claims, 13 Drawing Sheets

(56) References Cited

FOREIGN PATENT DOCUMENTS

| WO | 2002068394 | 9/2002 |
|---|---|---|
| WO | 2002095058 | 11/2002 |
| WO | 2007024863 | 3/2007 |
| WO | 2009015133 | 1/2009 |
| WO | 2011150300 | 12/2011 |
| WO | 2015127474 | 8/2015 |

OTHER PUBLICATIONS

Cnop et al., "Mechanisms of pancreatic beta cell death in type 1 and type 2 diabetes", Diabetes, 2005, v54 supplement 2, pp. s97-s107.
DeFronzo et al., "Mechanism of metformin action in obese and lean noninsulin-dependent diabetic subjects", J Clin Endocrinol Metab, 1991, 73(6), pp. 1294-1301.
DeWitt et al., "Outpatient Insulin Therapy in Type 1 and Type 2 Diabetes Mellitus", JAMA, 2003, v289(17), pp. 2254-2264 and pp. e1-e7.
During et al., "Controlled Release of Dopamine from a Polymeric Brain Implant: in vivo Characterization", Annals of Neurology, 1989, 25(4), pp. 351-356.
Final Office Action dated Apr. 12, 2016 in U.S. Appl. No. 14/364,792.
Final Office Action dated Apr. 10, 2014 received in copending U.S. Appl. No. 13/700,191.
Final Office Action dated Apr. 17, 2017 from related U.S. Appl. No. 13/700,191.
Final Office Action dated Feb. 21, 2019 in related U.S. Appl. No. 13/700,191.
Final Office Action dated Jul. 9, 2019 in related U.S. Appl. No. 14/364,792.
Final Office Action dated Mar. 12, 2008 received in copending U.S. Appl. No. 11/507,652.
Final Office Action dated Oct. 16, 2017 in U.S. Appl. No. 14/364,792.
Goodson, "Medical Applications Controlled Release", J Neurosurg, 1984, 2, pp. 115-138.
Howard et al., "Intracerebral drug delivery in rats with lesion-induced memory deficits", J Neurosurg, 1989, 71, pp. 105-112.
Ishikawa et al., "Requirements of src family kinase activity associated with CD45 for myeioma cell proliferation by interleukin-6", Blood, 2002, 99, pp. 2172-2178.
Johnson et al., "Phosphorylated immunoreceptor signaling motifs (ITAMs) exhibit unique abilities to bind and activate Lyn and Syk tyrosine kinases," J Immunol, 1995, 155(10), pp. 4596-4603.
Kidshealth, retrieved from http://kidshealth.org/parent!medical/endocrine/prevention.html on Sep. 8, 2015, 2 pages.
Langer and Wise, "Medical Applications of Controlled Release", CRC Pres, 1984, Boca Raton, FL. Too voluminous, not provided.
Langer et al., "Chemical and Physical Structure of Polymers as Carriers for Controlled Release of Bioactive Agents: A Review", JMS-Rev Macromol Chem Phys, 1983, 23(1), pp. 61-126.
Langer, "New methods of drug delivery", Science, 1990, 249(4976), pp. 1527-1533.
Levy et al., "Inhibition of calcification of bioprosthetic heart valves by local controlled-release diphosphonate", Science, 1985, 228(4696), pp. 190-192.
Lipinski et al., "Bronchodilator and antiulcer phenoxypyrimidinones," J Med Chem, 1980, 23(9), pp. 1026-1031.
Lopez-Berestein, "Treatment of Systemic Fungal Infections with Liposomal-Amphotericin B", ibid., 1989, pp. 317-327.
Ma et al., "Activation of the cold-sensing TRPM8 channel triggers UCP1-dependent thermogenesis and prevents obesity", Journal of Molecular Biology, 2012, 4, pp. 88-96.
Masuda et al., "Peptic Ulcer in Dabetes Millitus", Gastroenterologia Japonica, 1976, 11(1), pp. 1-4.
Mayerson et al., "The effects of rosiglitazone on linsulin sensitivity, lipolysis, and hepatic and skeletal muscle triglyceride content in patients with type 2 diabetes", Diabetes, 2002, 51(3), pp. 797-802.

Mayo Clinic, definition (retrieved from http://www.mayoclinic.org/diseases-conditions/type-1-diabetes/basics/definition/con20019573 on Feb. 27, 2017, 3 pages).
MedlinePlus (retrieved from https://www.nlm.nih.gov/medlineplus/ency/article/000305.htm on Sep. 8, 2015, 10 pages).
Meyer et al., "The benefits of metformin therapy during continuous subcutaneous insulin infusion treatment of type 1 diabetic patients", Diabetes Care, 2002, v25(12), pp. 2153-2158.
Muller et al., "Interaction of phosphatidylinositolglycan(-peptides) with plasma membrane lipid rafts triggers insulin-mimetic signaling in rat adipocytes", Arch of Biochem Biophys, 2002, 408, pp. 7-16.
Non-Final Office Action dated Apr. 17, 2015 received in related U.S. Appl. No. 14/182,380.
Non-Final Office Action dated May 20, 2015 in related U.S. Appl. No. 14/364,792.
Non-Final Office Action dated Oct. 7, 2015 received in U.S. Appl. No. 14/364,792.
Non-Final Office Action dated Aug. 30, 2016 in related U.S. Appl. No. 13/700,191.
Non-Final Office Action dated Jan. 18, 2018 in related U.S. Appl. No. 13/700,191.
Non-Final Office Action dated Apr. 11, 2013 received in copending U.S. Appl. No. 13/700,191.
Non-final Office Action dated Apr. 12, 2018 issued in related U.S. Appl. No. 15/684,130.
Non-Final Office Action dated Dec. 11, 2009 received in copending U.S. Appl. No. 11/507,652.
Non-Final Office Action dated Dec. 21, 2011 in co-pending U.S. Appl. No. 12/495,857.
Non-Final Office Action dated Dec. 30, 2016 received in related U.S. Appl. No. 14/941,473.
Non-final Office Action dated Jul. 31, 2012 in co-pending U.S. Appl. No. 12/495,857.
Non-Final Office Action dated Jun. 27, 2012 received in co-pending U.S. Appl. No. 12/527,801.
Non-Final Office Action dated Mar. 20, 2009 received in copending U.S. Appl. No. 11/507,652.
Non-Final Office Action dated May 28, 2013 received in copending U.S. Appl. No. 13/690,548.
Non-Final Office Action dated Nov. 16, 2011 received in copending U.S. Appl. No. 12/837,067.
Non-Final Office Action dated Apr. 4, 2023 in related U.S. Appl. No. 17/314,543.
Non-Final Office Action dated Sep. 10, 2008 received in copending U.S. Appl. No. 11/507,652.
Non-Final Office Action dated Sep. 7, 2007 received in copending U.S. Appl. No. 11/507,652.
Notice of Allowance dated Apr. 9, 2010 received in copending U.S. Appl. No. 11/507,652.
Notice of Allowance dated Aug. 31, 2012 received in co-pending U.S. Appl. No. 12/837,067.
Notice of Allowance dated Jan. 24, 2014 received in copending U.S. Appl. No. 13/690,548.
Notice of Allowance dated Jun. 6, 2013 received in copending U.S. Appl. No. 12/495,857.
Notice of Allowance dated May 26, 2017 in related U.S. Appl. No. 14/941,473.
Notice of Allowance dated Nov. 28, 2018 in related U.S. Appl. No. 15/684,130.
Notice of Allowance issued on Aug. 17, 2015 for related U.S. Appl. No. 14/182,380.
Ochman et al., "The Lyn Kinase Activator MLR-1023 is a Novel Insulin Receptor Potentiator that Elicits a Rapid-Onset and Durable Improvement in Glucose Homeostasis in Animal Models of Type 2 Diabetes", The Journal of Pharmacology and Experimental Therapeutics, 2012, 342(1), pp. 23-32.
Office Action dated Feb. 4, 2020 in related U.S. Appl. No. 16/286,976.
Office Action dated Oct. 29, 2018 in related U.S. Appl. No. 14/364,792.
Pubchem, Substance Record for SID 313487653, http://pubchem.ncbi.nlm.nih.gov/substance/313487653.
Pubchem, Substance Record for SID 313508515, http:/pubchem.ncbi.nlm.nih.gov/substance/313508515.

(56) References Cited

OTHER PUBLICATIONS

Raj et al., "Oral Insulin—A Perspective", Journal of Biomaterials Applications, 2003, 17, pp. 183-196.
Reaven, "Role of insulin resistance in human disease (syndrome X): an expanded definition", Annu Rev Med, 1993, 44, pp. 121-131.
Rossato et al., "Human white adipocytes express the cold receptor TRPM8 which activation induces UCP1 expression, mitochondrial activation and heat production", Molecular and Cellular Endocrinology, 2014, 383, pp. 137-146.
Saporito et al., "MLR-1 023:a drug candidate for type II diabetes with a novel molecular target discovered using an in vivo repositioning approach", Chemical Information Bulletin, 2007, v59(2), p. 28.
Sefton, "Implantable Pumps", CRC Crit Ref Biomed Eng, 1987, 14(3), pp. 201-240.
Smolen and Ball, "Controlled Drug Bioavailability, Drug Product Design and Performance," Wiley, New York, 1984.
SRC Kinase, [on line], Jan. 12, 2006, URL, http://www.cellsignal.com/pdf/7775.pdf.
St. Charles et al., "Health economic comparison between continuous subcutaneous insulin infusion and multiple daily injections of insulin for the treatment of adult type 1 diabetes in Canada", Clinical Therapeutics Excerptra Medica, 2009, 31(3), p. 657.
Summy et al., "AP23846, a novel and highly potent Src family kinase inhibitor, reduces vascular endothelial growth factor and interlieukin-8 expression in human solid tumor cell lines and abrogates downstream angiogenic processes", Mol CancerTher, 2005, 4(12), pp. 1900-1911.
Treat et al., "Liposomes in the Therapy of Infectious Disease and Cancer", Lopez-Berestein and Fidler (eds.), Liss, New York, 1989, pp. 353-365.
Wesch et al., "High throughput screening for protein kinase inhibitors", Comb Chem High Throughput Screen, 2005, 8(2), pp. 181-195.
Z-LYTE Kinase Assay Kits, 2008, Invitrogen website http://www.invitrogen.com.
Non-Final Office Action dated Jan. 21, 2021 in related U.S. Appl. No. 16/546,595.
Notice of Allowance dated Feb. 9, 2021 in related U.S. Appl. No. 16,286,976.
Non-Final Office Action dated Feb. 19, 2021 in related U.S. Appl. No. 16/737,200.
Final Office Action dated Jul. 1, 2021 received in U.S. Appl. No. 16/546,595.
Final Office Action dated Oct. 5, 2021 received in U.S. Appl. No. 16/737,200.
Final Office Action dated Jul. 21, 2022 in related U.S. Appl. No. 16/737,200.
Garcia et al., "Evaluation of markers of beige adipocytes in white adipose tissue of mouse", Nutrition and Metabolism, 2016, 13(14), pp. 1-14.
Non-Final Office Action dated Apr. 14, 2023 in related U.S. Appl. No. 16/737,200.
Final Office Action dated May 25, 2023 in related U.S. Appl. No. 16/546,595.
Chang-Chen et al., "B-cell Failure as a Complication of Diabetes", Rev Endocr Metab Disord, 2008, 9(4), pp. 329-343.
Non-Final Office Action dated Nov. 25, 2022 in related U.S. Appl. No. 16/546,595.
Hong et al., "Antidiabetic and Beta Cell-Protection Activities of Purple Corn Anthocyanins", Biomol Ther, 2013, 21(4), pp. 284-289.
Non-Final Office Action dated Aug. 14, 2023 in related U.S. Appl. No. 17/314,543.
Final Office Action dated Aug. 18, 2023 in related U.S. Appl. No. 16/737,200.
Notice of Allowance dated Jan. 11, 2024 in related U.S. Appl. No. 16/546,595.
Final Office Action dated Jan. 17, 2024 in related U.S. Appl. No. 17/314,543.
Advisory Action dated Nov. 20, 2023 in related U.S. Appl. No. 16/737,200.
Notice of Allowance dated Apr. 22, 2024 in related U.S. Appl. No. 17/314,543.

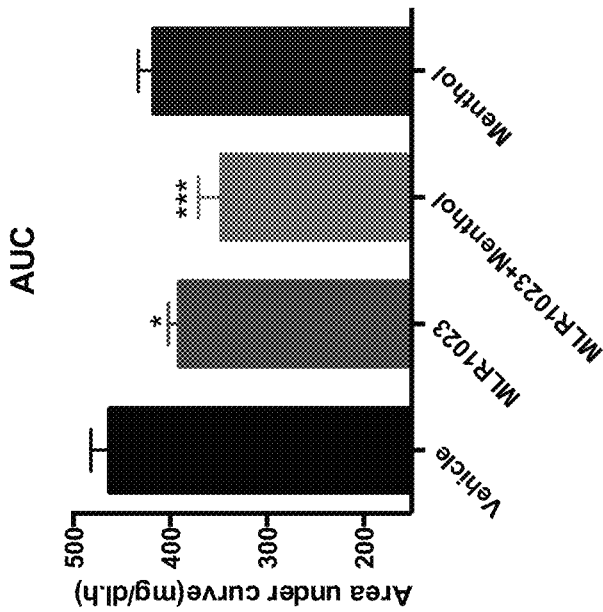
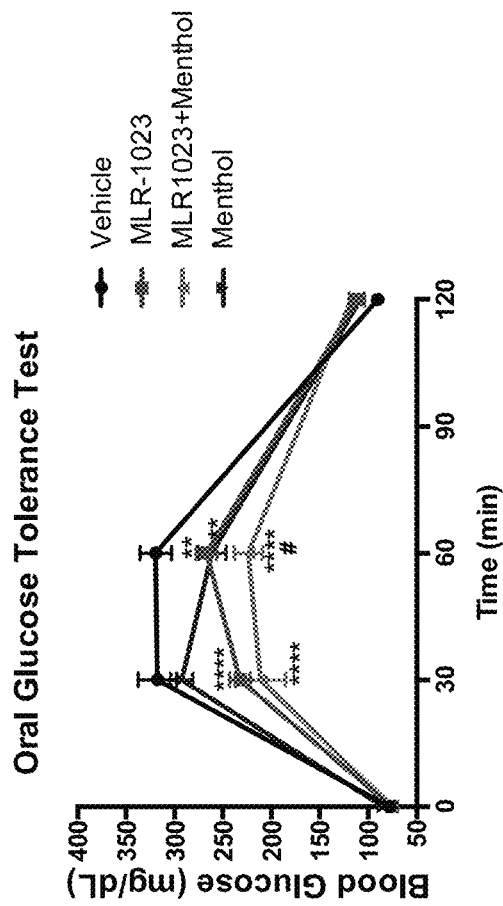
Figure 13

TREATMENT OF ADIPOCYTES

CROSS-REFERENCE TO RELATED APPLICATIONS

This application claims priority to U.S. Application No. 62/483,584, filed Apr. 10, 2017, which is incorporated herein by reference in its entirety.

FIELD

The present disclosure is directed, in part, to compositions comprising a lyn kinase activator and a TRPM8 agonist, and to methods of: reducing blood glucose levels, weight gain, or fat depot levels; treating metabolic syndrome, Syndrome X, obesity, prediabetes, type II diabetes, type I diabetes; treating hypercholesterolemia, hypertension, coronary heart disease, diabetic neuropathy, lipodystrophy, diabetic retinopathy, erectile dysfunction, kidney disease, dyslipidemia, dyslipoproteinemia, a peroxisome proliferator activated receptor-associated disorder, septicemia, a thrombotic disorder, or pancreatitis; inducing the beiging of adipocytes; and/or preventing pancreatic beta cell degeneration, by administering a lyn kinase activator and a TRPM8 agonist.

BACKGROUND

Lyn kinase is a member of the src family of non-receptor protein tyrosine kinases that is predominantly expressed in B-lymphoid and myeloid cells (see, Briggs et al., Biochemistry, 2000, 39, 489-495). Lyn kinase participates in signal transduction from cell surface receptors that lack intrinsic tyrosine kinase activity. Activation of the lyn kinase activity is necessary for proliferation of CD45+ myeloma cells stimulated by IL-6 (see, Ishikawa et al, Blood, 2002, 99, 2172-2178). Association of lyn and fyn with the proline-rich domain of glycoprotein VI regulates intracellular signaling (see, Suzuki-Inoue et al., J. Biol. Chem., 2002, 277, 21561-21566). The lyn/CD22/SHP-1 pathway is also important in autoimmunity (see, Blasioli et al., Curr. Dir. Autoimmun., 2002, 5, 151-160).

Obesity, hyperlipidemia, and diabetes have been shown to play a causal role in various disorders including, for example, atherosclerotic cardiovascular diseases, which currently account for a considerable proportion of morbidity in Western society. One human disorder, termed "Syndrome X" or "Metabolic Syndrome," is manifested by defective glucose metabolism (e.g., insulin resistance), elevated blood pressure (i.e., hypertension), and a blood lipid imbalance (i.e., dyslipidemia) (see, Reaven, Annu. Rev. Med., 1993, 44, 121-131).

For many years, there was believed to be only two kinds of fat cells: white adipocytes, which come from fat precursors, have a primary function to store fat and produce hormones; and brown adipocytes, which arise from muscle precursors, are full of mitochondria to burn fat to create non-shivering thermogenic energy. The presence of brown adipocyte tissue correlates with enhanced insulin sensitivity and energy expenditure. In comparison to white adipocytes, brown adipocytes secrete levels of adiponectin and resistin that enhance whole body glucose utilization. A third type of fat cell has been discovered: beige adipocytes, which are essentially white adipocytes that have been induced into energy-burning cells similar to brown adipocytes. One method of treating obesity may be to induce the creation of beige adipocytes from white adipocytes. A hallmark of both brown and beige adipocytes is the expression of thermogenic genes. However, while brown adipocytes express these genes at basal levels, beige adipocytes are thought to express them only in the presence of agonists such as adrenergic or naturetic peptides.

None of the currently commercially available drugs for modulating lyn kinase or managing elevated glucose levels have a general utility in regulating lipid, lipoprotein, insulin and glucose levels in the blood. Thus, compounds that have one or more of these utilities are clearly needed. Furthermore, there is a clear need to develop safer drugs that are efficacious at lowering serum cholesterol, increasing HDL serum levels, preventing coronary heart disease, and/or treating existing disease such as atherosclerosis, obesity, diabetes, and other diseases that are affected by glucose metabolism and/or elevated glucose levels.

SUMMARY

The present disclosure provides compositions comprising: a lyn kinase activator, or a pharmaceutically acceptable salt thereof, and a transient receptor potential cation channel subfamily M member 8 (TRPM8) agonist.

In some embodiments, the lyn kinase activator is of the formula:

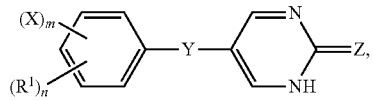

wherein: $R^1$ is an alkyl group; X is a halogen; Y is O, S, or NH; Z is O or S; and n is an integer from 0 to 5 and m is 0 or 1, wherein m+n is less than or equal to 5; or a pharmaceutically acceptable salt thereof.

In some embodiments, the lyn kinase activator is of the formula:

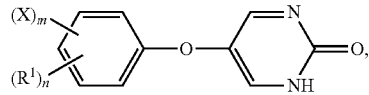

wherein: $R^1$ is an alkyl group; X is a halogen; and n is an integer from 0 to 5 and m is 0 or 1, wherein m+n is less than or equal to 5; or a pharmaceutically acceptable salt thereof.

In some embodiments, the lyn kinase activator is of the formula:

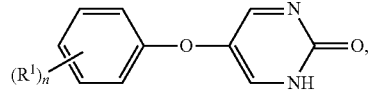

wherein $R^1$ is an alkyl group and n is an integer from 0 to 5; or a pharmaceutically acceptable salt thereof.

In some embodiments, the lyn kinase activator is of the formula:

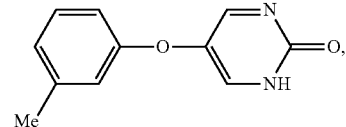 [SMILES: Cc1cccc(Oc2cnc(=O)[nH]c2)c1]

or a pharmaceutically acceptable salt thereof.

In some embodiments, the lyn kinase activator is of the formula:

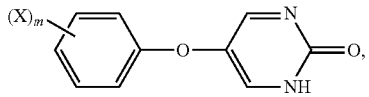

wherein X is a halogen and m is an integer from 0 to 1; or a pharmaceutically acceptable salt thereof.

In some embodiments, the lyn kinase activator is of the formula:

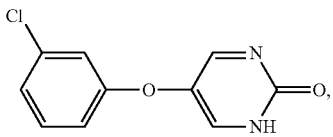 [SMILES: O=c1ncc(Oc2cccc(Cl)c2)c[nH]1]

or a pharmaceutically acceptable salt thereof.

In some embodiments, the lyn kinase activator is of the formula:

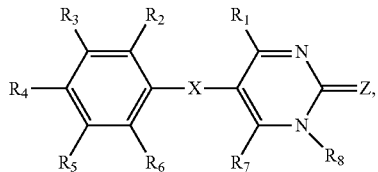

wherein: each of $R_1$, $R_2$, $R_3$, $R_4$, $R_5$, $R_6$, and $R_7$ are, independently, a hydrogen, alkoxy, alkyl, alkenyl, alkynyl, aryl, aryloxy, benzyl, cycloalkyl, halogen, heteroaryl, heterocycloalkyl, —CN, —OH, —NO$_2$, —CF$_3$, —CO$_2$H, —CO$_2$alkyl, or —NH$_2$; $R_8$ is an alkyl or hydrogen; X is O, S, NH, or N-alkyl; and Z is O or S; or a pharmaceutically acceptable salt thereof.

In some embodiments, the lyn kinase activator is of the formula:

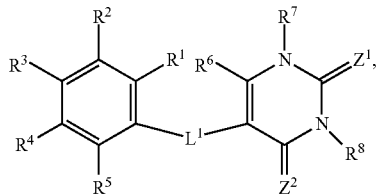

wherein: $R^1$ is H, halo, $C_{1-6}$alkyl, $C_{2-6}$alkenyl, $C_{2-6}$alkynyl, $C_{1-6}$haloalkyl, $C_{1-6}$hydroxyalkyl, $C_{3-6}$cycloalkyl, aryl, heteroaryl, CN, NO$_2$, OR$^{a1}$, SR$^{a1}$, C(O)R$^{b1}$, C(O)NR$^{c1}$R$^{d1}$, C(O)OR$^{a1}$, OC(O)R$^{b1}$, OC(O)NR$^{c1}$R$^{d1}$, NR$^{c1}$R$^{d1}$, NR$^{c1}$C(O)R$^{b1}$, NR$^{c1}$C(O)NR$^{c1}$R$^{d1}$, NR$^{c1}$C(O)OR$^{a1}$, NR$^{c1}$S(O)$_2$NR$^{c1}$R$^{d1}$, S(O)R$^{b1}$, S(O)NR$^{c1}$R$^{d1}$, S(O)$_2$R$^{b1}$, NR$^{c1}$S(O)$_2$R$^{b1}$, or S(O)$_2$NR$^{c1}$R$^{d1}$, wherein each of $C_{1-6}$alkyl, $C_{2-6}$alkenyl, $C_{2-6}$alkynyl, $C_{1-6}$haloalkyl, $C_{1-6}$hydroxyalkyl, $C_{3-6}$cycloalkyl, aryl, and heteroaryl, is optionally substituted by 1, 2, 3, 4, or 5 substituents independently selected from halo, $C_{1-6}$alkyl, $C_{2-6}$alkenyl, $C_{2-6}$alkynyl, $C_{1-6}$haloalkyl, $C_{1-6}$hydroxyalkyl, $C_{3-6}$cycloalkyl, aryl, heteroaryl, CN, NO$_2$, OR$^{a2}$, SR$^{a2}$, C(O)R$^{b2}$, C(O)NR$^{c2}$R$^{d2}$, C(O)OR$^{a2}$, OC(O)R$^{b2}$, OC(O)NR$^{c2}$R$^{d2}$, NR$^{c2}$R$^{d2}$, NR$^{c2}$C(O)R$^{b2}$, NR$^{c2}$C(O)NR$^{c2}$R$^{d2}$, NR$^{c2}$C(O)OR$^{a2}$, NR$^{c2}$S(O)NR$^{c2}$R$^{d2}$, S(O)R$^{b2}$, S(O)NR$^{c2}$R$^{d2}$, S(O)$_2$R$^{b2}$, NR$^{c2}$S(O)$_2$R$^{b2}$, and S(O)$_2$ NR$^{c2}$R$^{d2}$; $R^2$ is H, halo, $C_{1-6}$alkyl, $C_{2-6}$alkenyl, $C_{2-6}$alkynyl, $C_{1-6}$haloalkyl, $C_{1-6}$hydroxyalkyl, $C_{3-6}$cycloalkyl, aryl, heteroaryl, CN, NO$_2$, OR$^{a1}$, SR$^{a1}$, C(O)R$^{b}$, C(O)NR$^{c1}$R$^{d1}$, C(O)OR$^{a1}$, OC(O)R$^{b1}$OC(O)NR$^{c1}$R$^{d1}$, NR$^{c1}$R$^{d1}$, NR$^{c1}$C(O)R$^{b1}$, NR$^{c1}$C(O)NR$^{c1}$R$^{d1}$, NR$^{c1}$C(O)OR$^{a1}$, NR$^{c1}$S(O)$_2$NR$^{c1}$R$^{d1}$, S(O)R$^{b1}$, S(O)NR$^{c1}$R$^{d1}$, S(O)$_2$R$^{b1}$, NR$^{c1}$S(O)$_2$ R$^{b1}$, or S(O)$_2$NR$^{c1}$R$^{d1}$, wherein each of $C_{1-6}$alkyl, $C_{2-6}$alkenyl, $C_{2-6}$alkynyl, $C_{1-6}$haloalkyl, $C_{1-6}$hydroxyalkyl, $C_{3-6}$cycloalkyl, aryl, and heteroaryl, is optionally substituted by 1, 2, 3, 4, or 5 substituents independently selected from halo, $C_{1-6}$alkyl, $C_{2-6}$alkenyl, $C_{2-6}$alkynyl, $C_{1-6}$haloalkyl, $C_{1-6}$hydroxyalkyl, $C_{3-6}$cycloalkyl, aryl, heteroaryl, CN, NO$_2$, OR$^{a2}$, SR$^{a2}$, C(O)R$^{b2}$, C(O)NR$^{c2}$R$^{d2}$, C(O)OR$^{a2}$, OC(O)R$^{b2}$, OC(O)NR$^{c2}$R$^{d2}$, NR$^{c2}$R$^{d2}$, NR$^{c2}$C(O)R$^{b2}$ NR$^{c2}$C(O)NR$^{c2}$R$^{d2}$, NR$^{c2}$C(O)OR$^{a2}$, NR$^{c2}$S(O)NR$^{c2}$R$^{12}$, S(O)R$^{b2}$, S(O)NR$^{c2}$R$^{d2}$, S(O)$_2$R$^{b2}$ NR$^{c2}$S(O)$_2$R$^{b2}$, and S(O)$_2$ NR$^{c2}$R$^{d2}$; $R^3$ is H, halo, $C_{1-6}$alkyl, $C_{2-6}$alkenyl, $C_{2-6}$alkynyl, $C_{1-6}$haloalkyl, $C_{1-6}$hydroxyalkyl, $C_{3-6}$cycloalkyl, aryl, heteroaryl, CN, NO$_2$, OR$^{a1}$, SR$^{a1}$, C(O)R$^{b1}$, C(O)NR$^{c1}$R$^{d1}$, C(O)OR$^{a1}$, OC(O)R$^{b1}$, OC(O)NR$^{c1}$R$^{d1}$, NR$^{c1}$R$^{d1}$, NR$^{c1}$C(O)R$^{b1}$, NR$^{c1}$C(O)NR$^{c1}$R$^{d1}$, NR$^{c1}$C(O)OR$^{a1}$, NR$^{c1}$S(O)$_2$NR$^{c1}$R$^{d1}$, S(O)R$^{b1}$, S(O)NR$^{c1}$R$^{d1}$, S(O)$_2$R$^{b1}$, NR$^{c1}$S(O)$_2$ R$^{b1}$, or S(O)$_2$NR$^{c1}$R$^{d1}$, wherein each of $C_{1-6}$alkyl, $C_{2-6}$alkenyl, $C_{2-6}$alkynyl, $C_{1-6}$haloalkyl, $C_{1-6}$hydroxyalkyl, $C_{3-6}$cycloalkyl, aryl, and heteroaryl, is optionally substituted by 1, 2, 3, 4, or 5 substituents independently selected from halo, $C_{1-6}$alkyl, $C_{2-6}$alkenyl, $C_{2-6}$alkynyl, $C_{1-6}$haloalkyl, $C_{1-6}$hydroxyalkyl, $C_{3-6}$cycloalkyl, aryl, heteroaryl, CN, NO$_2$, OR$^{a2}$ SR$^{a2}$, C(O)R$^{b2}$, C(O)NR$^{c2}$R$^{d2}$, C(O)OR$^{a2}$, OC(O)R$^{b2}$, OC(O)NR$^{c2}$R$^{d2}$, NR$^{c2}$R$^{d2}$, NR$^{c2}$C(O)R$^{b2}$ NR$^{c2}$C(O)NR$^{c2}$R$^{d2}$, NR$^{c2}$C(O)OR$^{a2}$, NR$^{c2}$S(O)NR$^{c2}$R$^{12}$, S(O)R$^{b2}$, S(O)NR$^{c2}$R$^{d2}$, S(O)$_2$R$^{b2}$ NR$^{c2}$S(O)$_2$R$^{b2}$, and S(O)$_2$ NR$^{c2}$R$^{d2}$; $R^4$ is H, halo, $C_{1-6}$alkyl, $C_{2-6}$alkenyl, $C_{2-6}$alkynyl, $C_{1-6}$haloalkyl, $C_{1-6}$hydroxyalkyl, $C_{3-6}$cycloalkyl, aryl, heteroaryl, CN, NO$_2$, OR$^{a1}$, SR$^{a1}$, C(O)R$^{b1}$, C(O)NR$^{c1}$R$^{d1}$, C(O)OR$^{a1}$, OC(O)R$^{b1}$, OC(O)NR$^{c1}$R$^{d1}$, NR$^{c1}$R$^{d1}$, NR$^{c1}$C(O)R$^{b1}$, NR$^{c1}$C(O)NR$^{c1}$R$^{d1}$, NR$^{c1}$C(O)OR$^{a1}$, NR$^{c1}$S(O)$_2$NR$^{c1}$R$^{d1}$, S(O)R$^{b1}$, S(O)NR$^{c1}$R$^{d1}$, S(O)$_2$R$^{b1}$, NR$^{c1}$S(O)$_2$ R$^{b1}$, or S(O)$_2$NR$^{c1}$R$^{d1}$, wherein each of $C_{1-6}$alkyl, $C_{2-6}$alkenyl, $C_{2-6}$alkynyl, $C_{1-6}$haloalkyl, $C_{1-6}$hydroxyalkyl, $C_{3-6}$cycloalkyl, aryl, and heteroaryl, is optionally substituted by 1, 2, 3, 4, or 5 substituents independently selected from halo, $C_{1-6}$alkyl, $C_{2-6}$alkenyl, $C_{2-6}$alkynyl, $C_{1-6}$haloalkyl, $C_{1-6}$hydroxyalkyl, $C_{3-6}$cycloalkyl, aryl, heteroaryl, CN, NO$_2$, OR$^{a2}$ SR$^{a2}$, C(O)R$^{b2}$, C(O)NR$^{c2}$R$^{d2}$, C(O)OR$^{a2}$, OC(O)R$^{b2}$, OC(O)NR$^{c2}$R$^{d2}$, NR$^{c2}$R$^{d2}$, NR$^{c2}$C(O)R$^{b2}$ NR$^{c2}$C(O)NR$^{c2}$R$^{d2}$, NR$^{c2}$C(O)OR$^{a2}$, NR$^{c2}$S(O)NR$^{c2}$R$^{12}$, S(O)R$^{b2}$, S(O)NR$^{c2}$R$^{d2}$, S(O)$_2$R$^{b2}$ NR$^{c2}$S(O)$_2$R$^{b2}$, and S(O)$_2$ NR$^{c2}$R$^{d2}$; $R^5$ is H, halo, $C_{1-6}$alkyl, $C_{2-6}$alkenyl, $C_{2-6}$alkynyl, $C_{1-6}$haloalkyl, $C_{1-6}$hydroxyalkyl, $C_{3-6}$cycloalkyl, aryl, heteroaryl, CN, NO$_2$, OR$^{a1}$, SR$^{a1}$, C(O)R$^{b1}$, C(O)NR$^{c1}$R$^{d1}$, C(O)OR$^{a1}$, OC(O)R$^{b1}$, OC(O)NR$^{c1}$R$^{d1}$, NR$^{c1}$R$^{d1}$, NR$^{c1}$C(O)R$^{b1}$, NR$^{c1}$C(O)NR$^{c1}$R$^{d1}$, NR$^{c1}$C(O)OR$^{a1}$, NR$^{c1}$S(O)$_2$NR$^{c1}$R$^{d1}$, S(O)R$^{b1}$, S(O)NR$^{c1}$R$^{d1}$, S(O)$_2$R$^{b1}$, NR$^{c1}$S(O)$_2$ R$^{b1}$, or S(O)$_2$NR$^{c1}$R$^{d1}$, wherein each of $C_{1-6}$alkyl, $C_{2-6}$alkenyl, $C_{2-6}$alkynyl, $C_{1-6}$haloalkyl, $C_{1-6}$hydroxyalkyl, $C_{3-6}$cycloalkyl, aryl, and heteroaryl, is optionally substituted by 1, 2, 3, 4, or 5 substituents independently selected from halo, $C_{1-6}$alkyl, $C_{2-6}$alkenyl, $C_{2-6}$alkynyl, $C_{1-6}$haloalkyl, $C_{1-6}$hydroxyalkyl, $C_{3-6}$cycloalkyl, aryl, heteroaryl, CN, NO$_2$, OR$^{a2}$ SR$^{a2}$, C(O)R$^{b2}$, C(O)NR$^{c2}$R$^{d2}$, C(O)OR$^{a2}$, OC(O)R$^{b2}$, OC(O)NR$^{c2}$R$^{d2}$, NR$^{c2}$R$^{d2}$, NR$^{c2}$C(O)R$^{b2}$ NR$^{c2}$C(O)NR$^{c2}$R$^{d2}$, NR$^{c2}$C(O)OR$^{a2}$, NR$^{c2}$S(O)NR$^{c2}$R$^{d2}$, S(O)R$^{b2}$, S(O)NR$^{c2}$R$^{d2}$, S(O)$_2$R$^{b2}$ NR$^{c2}$S(O)$_2$R$^{b2}$, and S(O)$_2$ NR$^{c2}$R$^{d2}$; or two adjacent groups of R$^1$, R$^2$, R$^3$, R$^4$, and R$^5$ can link to form a fused cycloalkyl or fused heterocycloalkyl group, each optionally substituted by 1, 2, or 3 substituents independently selected from halo, C$_{1-6}$alkyl, C$_{2-6}$alkenyl, C$_{2-6}$alkynyl, C$_{1-6}$haloalkyl, C$_{1-6}$hydroxyalkyl, C$_{3-6}$cycloalkyl, aryl, heteroaryl, CN, NO$_2$, OR$^{a2}$, SR$^{a2}$, C(O)R$^{b2}$, C(O)NR$^{c2}$R$^{d2}$, C(O)OR$^{a2}$, OC(O)R$^{b2}$, OC(O)NR$^{c2}$R$^{d2}$, NR$^{c2}$R$^{d2}$, NR$^{c2}$C(O)R$^{b2}$ NR$^{c2}$C(O)NR$^{c2}$R$^{d2}$, NR$^{c2}$C(O)OR$^{a2}$, NR$^{c2}$S(O)NR$^{c2}$R$^{d2}$, S(O)R$^{b2}$, S(O)NR$^{c2}$R$^{d2}$, S(O)$_2$R$^{b2}$ NR$^{c2}$S(O)$_2$R$^{b2}$, and S(O)$_2$NR$^{c2}$R$^{d2}$; R$^6$ is H, halo, C$_{1-6}$alkyl, C$_{2-6}$alkenyl, C$_{2-6}$alkynyl, C$_{1-6}$haloalkyl, C$_{1-6}$hydroxyalkyl, C$_{3-6}$cycloalkyl, aryl, heteroaryl, CN, NO$_2$, OR$^{a1}$, SR$^{a1}$, C(O)R$^{b1}$, C(O)NR$^{c1}$R$^{d1}$, C(O)OR$^{a1}$, OC(O)R$^{b1}$, OC(O)NR$^{c1}$R$^{d1}$, NR$^{c1}$R$^{d1}$, NR$^{c1}$C(O)R$^{b1}$, NR$^{c1}$C(O)NR$^{c1}$R$^{d1}$, NR$^{c1}$C(O)OR$^{a1}$, NR$^{c1}$S(O)$_2$NR$^{c1}$R$^{d1}$, S(O)R$^{b1}$, S(O)NR$^{c1}$R$^{d1}$, S(O)$_2$R$^{b1}$, NR$^{c1}$S(O)$_2$R$^{b1}$, or S(O)$_2$NR$^{c1}$R$^{d1}$, wherein each of C$_{1-6}$alkyl, C$_{2-6}$alkenyl, C$_{2-6}$alkynyl, C$_{1-6}$haloalkyl, C$_{1-6}$hydroxyalkyl, C$_{3-6}$cycloalkyl, aryl, and heteroaryl, is optionally substituted by 1, 2, 3, 4, or 5 substituents independently selected from halo, C$_{1-6}$alkyl, C$_{2-6}$alkenyl, C$_{2-6}$alkynyl, C$_{1-6}$haloalkyl, C$_{1-6}$hydroxyalkyl, C$_{3-6}$cycloalkyl, CN, NO$_2$, OR$^{a2}$, SR$^{a2}$, C(O)R$^{b2}$, C(O)NR$^{c2}$R$^{d2}$, C(O)OR$^{a2}$, OC(O)R$^{b2}$, OC(O)NR$^{c2}$R$^{d2}$, NR$^{c2}$R$^{d2}$, NR$^{c2}$C(O)R$^{b2}$ NR$^{c2}$C(O)NR$^{c2}$R$^{d2}$, NR$^{c2}$C(O)OR$^{a2}$, NR$^{c2}$S(O)NR$^{c2}$R$^{d2}$, S(O)R$^{b2}$, S(O)NR$^{c2}$R$^{d2}$, S(O)$_2$R$^{b2}$ NR$^{c2}$S(O)$_2$R$^{b2}$, and S(O)$_2$NR$^{c2}$R$^{d2}$; R$^7$ is H, C$_{1-6}$alkyl, C$_{1-6}$haloalkyl, C$_{1-6}$hydroxyalkyl, C(O)R$^{b1}$, C(O)NR$^{c1}$R$^{d1}$, C(O)OR$^{a1}$, S(O)R$^{b1}$, S(O)NR$^{c1}$R$^{d1}$, S(O)$_2$R$^{b1}$, or S(O)$_2$NR$^{c1}$R$^{d1}$; R$^8$ is H, C$_{1-6}$alkyl, C$_{1-6}$haloalkyl, C$_{1-6}$hydroxyalkyl, C(O)R$^b$, C(O)NR$^{c1}$R$^{d1}$, C(O)OR$^{a1}$, S(O)R$^{b1}$, S(O)NR$^{c1}$R$^{d1}$, S(O)$_2$R$^{b1}$, or S(O)$_2$NR$^{c1}$R$^{d1}$; R$^{a1}$, R$^{b1}$, R$^{c1}$, and R$^{d1}$ are each, independently, selected from H, C$_{1-6}$alkyl, C$_{1-6}$haloalkyl, C$_{1-6}$hydroxyalkyl, C$_{2-6}$alkenyl, C$_{2-6}$alkynyl, aryl, cycloalkyl, heteroaryl, heterocycloalkyl, arylalkyl, heteroarylalkyl, cycloalkylalkyl, and heterocycloalkylalkyl, wherein each of C$_{1-6}$alkyl, C$_{1-6}$haloalkyl, C$_{1-6}$hydroxyalkyl, C$_{2-6}$alkenyl, C$_{2-6}$alkynyl, aryl, cycloalkyl, heteroaryl, heterocycloalkyl, arylalkyl, heteroarylalkyl, cycloalkylalkyl, and heterocycloalkylalkyl is optionally substituted with 1, 2, 3, 4, or 5 substituents independently selected from OH, NO$_2$, CN, amino, halo, C$_{1-6}$alkyl, C$_{1-6}$alkoxy, C$_{1-6}$haloalkyl, C$_{1-6}$hydroxyalkyl, and C$_{1-6}$haloalkoxy; or R$^{c1}$ and R$^{d1}$ together with the N atom to which they are attached form a 4-, 5-, 6-, or 7-membered heterocycloalkyl group or heteroaryl group, each optionally substituted with 1, 2, or 3 substituents independently selected from OH, NO$_2$, CN, amino, halo, C$_{1-6}$alkyl, C$_{1-6}$alkoxy, C$_{1-6}$haloalkyl, C$_{1-6}$hydroxyalkyl, and C$_{1-6}$haloalkoxy; R$^{a2}$, R$^{b2}$, R$^{c2}$, and R$^{d2}$ are each, independently, selected from H, C$_{1-6}$alkyl, C$_{1-6}$haloalkyl, C$_{1-6}$hydroxyalkyl, C$_{2-6}$alkenyl, C$_{2-6}$alkynyl, aryl, cycloalkyl, heteroaryl, heterocycloalkyl, arylalkyl, heteroarylalkyl, cycloalkylalkyl, and heterocycloalkylalkyl, wherein each of C$_{1-6}$alkyl, C$_{1-6}$haloalkyl, C$_{1-6}$hydroxyalkyl, C$_{2-6}$alkenyl, C$_{2-6}$alkynyl, aryl, cycloalkyl, heteroaryl, heterocycloalkyl, arylalkyl, heteroarylalkyl, cycloalkylalkyl, or heterocycloalkylalkyl is optionally substituted with 1, 2, or 3 substituents independently selected from OH, NO$_2$, CN, amino, halo, C$_{1-6}$alkyl, C$_{1-6}$alkoxy, C$_{1-6}$haloalkyl, C$_{1-6}$hydroxyalkyl, and C$_{1-6}$haloalkoxy; or R$^{c2}$ and R$^{d2}$ together with the N atom to which they are attached form a 4-, 5-, 6-, or 7-membered heterocycloalkyl group or heteroaryl group, each optionally substituted with 1, 2, or 3 substituents independently selected from OH, NO$_2$, CN, amino, halo, C$_{1-6}$alkyl, C$_{1-6}$alkoxy, C$_{1-6}$haloalkyl, C$_{1-6}$hydroxyalkyl, and C$_{1-6}$haloalkoxy; Z$^1$ is O, S, or NR$^9$; R$^9$ is H, OH, C$_{1-6}$alkoxy, C$_{1-6}$haloalkyl, C$_{1-6}$hydroxyalkyl, aryloxy, heteroaryloxy, CN, or NO$_2$; Z$^2$ is O, S, or NR$^{10}$; R$^{10}$ is H, OH, C$_{1-6}$alkoxy, C$_{1-6}$haloalkyl, C$_{1-6}$hydroxyalkyl, aryloxy, heteroaryloxy, CN, or NO$_2$; L$^1$ is O, S, or NR$^{11}$; and R$^{11}$ is H, C$_{1-6}$alkyl, C$_{1-6}$haloalkyl, C$_{1-6}$hydroxyalkyl, C(O)R$^{b1}$, C(O)NR$^{c1}$R$^{d1}$, C(O)OR$^{a1}$, S(O)R$^{b1}$, S(O)NR$^{c1}$R$^{d1}$, S(O)$_2$R$^{b1}$, or S(O)$_2$NR$^{c1}$R$^{d1}$; or a pharmaceutically acceptable salt thereof.

In some embodiments, the lyn kinase activator is of the formula:

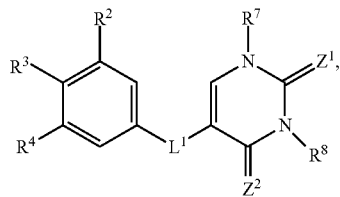

wherein: R$^2$, R$^3$, and R$^4$ are each, independently, H, halo, C$_{1-6}$alkyl, C$_{1-6}$hydroxyalkyl, or C$_{1-6}$haloalkyl; R$^7$ is H, C$_{1-6}$alkyl, C(O)R$^{b1}$, C(O)NR$^{c1}$R$^{d1}$, or C(O)OR$^{a1}$; R$^8$ is H, C$_{1-6}$alkyl, C(O)R$^{b1}$, C(O)NR$^{c1}$R$^{d1}$, or C(O)OR$^{a1}$; R$^{a1}$, R$^{b1}$, R$^{c1}$, and R$^{d1}$ are each, independently, selected from H, C$_{1-6}$alkyl, C$_{1-6}$haloalkyl, C$_{1-6}$hydroxyalkyl, C$_{2-6}$alkenyl, C$_{2-6}$alkynyl, aryl, cycloalkyl, heteroaryl, heterocycloalkyl, arylalkyl, heteroarylalkyl, cycloalkylalkyl, and heterocycloalkylalkyl, wherein each of C$_{1-6}$alkyl, C$_{1-6}$haloalkyl, C$_{1-6}$hydroxyalkyl, C$_{2-6}$alkenyl, C$_{2-6}$alkynyl, aryl, cycloalkyl, heteroaryl, heterocycloalkyl, arylalkyl, heteroarylalkyl, cycloalkylalkyl, and heterocycloalkylalkyl is optionally substituted with 1, 2, 3, 4, or 5 substituents independently selected from OH, NO$_2$, CN, amino, halo, C$_{1-6}$alkyl, C$_{1-6}$alkoxy, C$_{1-6}$haloalkyl, C$_{1-6}$hydroxyalkyl, and C$_{1-6}$haloalkoxy; or R$^{c1}$ and R$^{d1}$ together with the N atom to which they are attached form a 4-, 5-, 6-, or 7-membered heterocycloalkyl group or heteroaryl group, each optionally substituted with 1, 2, or 3 substituents independently selected from OH, NO$_2$, CN, amino, halo, C$_{1-6}$alkyl, C$_{1-6}$alkoxy, C$_{1-6}$haloalkyl, C$_{1-6}$hydroxyalkyl, and C$_{1-6}$haloalkoxy; Z$^1$ is O or S; Z$^2$ is O or S; and L$^1$ is O or S; or a pharmaceutically acceptable salt thereof.

In some embodiments, the lyn kinase activator is of the formula:

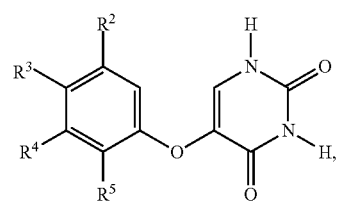

wherein: R$^2$, R$^3$, R$^4$, and R$^5$ are each, independently, H, F, Cl, CH$_3$, SCH$_3$, OCH$_3$, C(CH$_3$)$_3$, CH(CH$_3$)$_2$, or C$_2$H$_5$; or a pharmaceutically acceptable salt thereof.

In some embodiments, the lyn kinase activator is of the formula:

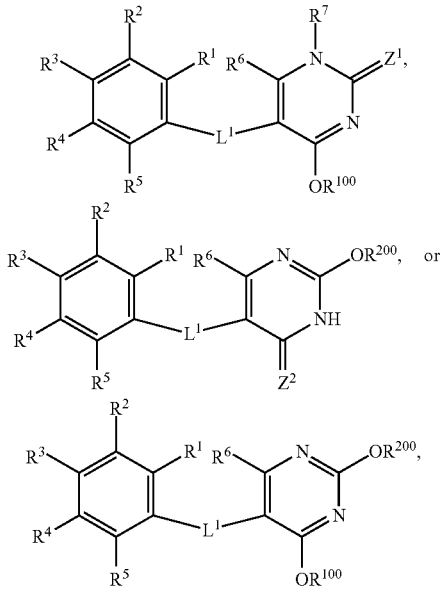

wherein: $R^1$ is H, halo, $C_{1-6}$alkyl, $C_{2-6}$alkenyl, $C_{2-6}$alkynyl, $C_{1-6}$haloalkyl, $C_{1-6}$hydroxyalkyl, $C_{3-6}$cycloalkyl, aryl, heteroaryl, CN, $NO_2$, $OR^{a1}$ $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)NR^{c1}R^{d1}$, $NR^{c1}C(O)OR^{a1}$, $NR^{c1}S(O)_2NR^{c1}R^{d1}$, $S(O)R^{b1}$, $S(O)NR^{c1}R^{d1}$, $S(O)_2R^{b1}$, $NR^{c1}S(O)_2R^{b1}$, or $S(O)_2NR^{c1}R^{d1}$, wherein each of $C_{1-6}$alkyl, $C_{2-6}$alkenyl, $C_{2-6}$alkynyl, $C_{1-6}$haloalkyl, $C_{1-6}$hydroxyalkyl, $C_{3-6}$cycloalkyl, aryl, and heteroaryl, is optionally substituted by 1, 2, 3, 4, or 5 substituents independently selected from halo, $C_{1-6}$alkyl, $C_{2-6}$alkenyl, $C_{2-6}$alkynyl, $C_{1-6}$haloalkyl, $C_{1-6}$hydroxyalkyl, $C_{3-6}$cycloalkyl, aryl, heteroaryl, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$, $NR^{c2}C(O)NR^{c2}R^{d2}$, $NR^{c2}C(O)OR^{a2}$, $NR^{c2}S(O)NR^{c2}R^{d2}$, $S(O)R^{b2}$, $S(O)NR^{c2}R^{d2}$, $S(O)_2R^{b2}$ $NR^{c2}S(O)_2R^{b2}$, and $S(O)_2 NR^{c2}R^{d2}$; $R^2$ is H, halo, $C_{1-6}$alkyl, $C_{2-6}$alkenyl, $C_{2-6}$alkynyl, $C_{1-6}$haloalkyl, $C_{1-6}$hydroxyalkyl, $C_{3-6}$cycloalkyl, aryl, heteroaryl, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)NR^{c1}R^{d1}$, $NR^{c1}C(O)OR^{a1}$, $NR^{c1}S(O)_2NR^{c1}R^{d1}$, $S(O)R^{b1}$, $S(O)NR^{c1}R^{d1}$, $S(O)_2R^{b1}$, $NR^{c1}S(O)_2R^{b1}$, or $S(O)_2NR^{c1}R^{d1}$, wherein each of $C_{1-6}$alkyl, $C_{2-6}$alkenyl, $C_{2-6}$alkynyl, $C_{1-6}$haloalkyl, $C_{1-6}$hydroxyalkyl, $C_{3-6}$cycloalkyl, aryl, and heteroaryl, is optionally substituted by 1, 2, 3, 4, or 5 substituents independently selected from halo, $C_{1-6}$alkyl, $C_{2-6}$alkenyl, $C_{2-6}$alkynyl, $C_{1-6}$haloalkyl, $C_{1-6}$hydroxyalkyl, $C_{3-6}$cycloalkyl, aryl, heteroaryl, CN, $NO_2$, $OR^{a2}$ $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$, $NR^{c2}C(O)NR^{c2}R^{d2}$, $NR^{c2}C(O)OR^{a2}$, $NR^{c2}S(O)NR^{c2}R^{12}$, $S(O)R^{b2}$, $S(O)NR^{c2}R^{d2}$, $S(O)_2R^{b2}$ $NR^{c2}S(O)_2R^{b2}$, and $S(O)_2 NR^{c2}R^{d2}$; $R^3$ is H, halo, $C_{1-6}$alkyl, $C_{2-6}$alkenyl, $C_{2-6}$alkynyl, $C_{1-6}$haloalkyl, $C_{1-6}$hydroxyalkyl, $C_{3-6}$cycloalkyl, aryl, heteroaryl, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)NR^{c1}R^{d1}$, $NR^{c1}C(O)OR^{a1}$, $NR^{c1}S(O)_2NR^{c1}R^{d1}$, $S(O)R^{b1}$, $S(O)NR^{c1}R^{d1}$, $S(O)_2R^{b1}$, $NR^{c1}S(O)_2R^{b1}$, or $S(O)_2NR^{c1}R^{d1}$, wherein each of $C_{1-6}$alkyl, $C_{2-6}$alkenyl, $C_{2-6}$alkynyl, $C_{1-6}$haloalkyl, $C_{1-6}$hydroxyalkyl, $C_{3-6}$cycloalkyl, aryl, and heteroaryl, is optionally substituted by 1, 2, 3, 4, or 5 substituents independently selected from halo, $C_{1-6}$alkyl, $C_{2-6}$alkenyl, $C_{2-6}$alkynyl, $C_{1-6}$haloalkyl, $C_{1-6}$hydroxyalkyl, $C_{3-6}$cycloalkyl, aryl, heteroaryl, CN, $NO_2$, $OR^{a2}$ $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$ $NR^{c2}C(O)NR^{c2}R^{d2}$, $NR^{c2}C(O)OR^{a2}$, $NR^{c2}S(O)NR^{c2}R^{d2}$, $S(O)R^{b2}$, $S(O)NR^{c2}R^{d2}$, $S(O)_2R^{b2}$ $NR^{c2}S(O)_2R^{b2}$, and $S(O)_2 NR^{c2}R^{d2}$; $R^4$ is H, halo, $C_{1-6}$alkyl, $C_{2-6}$alkenyl, $C_{2-6}$alkynyl, $C_{1-6}$haloalkyl, $C_{1-6}$hydroxyalkyl, $C_{3-6}$cycloalkyl, aryl, heteroaryl, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)NR^{c1}R^{d1}$, $NR^{c1}C(O)OR^{a1}$, $NR^{c1}S(O)_2NR^{c1}R^{d1}$, $S(O)R^{b1}$, $S(O)NR^{c1}R^{d1}$, $S(O)_2R^{b1}$, $NR^{c1}S(O)_2 R^{b1}$, or $S(O)_2NR^{c1}R^{d1}$, wherein each of $C_{1-6}$alkyl, $C_{2-6}$alkenyl, $C_{2-6}$alkynyl, $C_{1-6}$haloalkyl, $C_{1-6}$hydroxyalkyl, $C_{3-6}$cycloalkyl, aryl, and heteroaryl, is optionally substituted by 1, 2, 3, 4, or 5 substituents independently selected from halo, $C_{1-6}$alkyl, $C_{2-6}$alkenyl, $C_{2-6}$alkynyl, $C_{1-6}$haloalkyl, $C_{1-6}$hydroxyalkyl, $C_{3-6}$cycloalkyl, aryl, heteroaryl, CN, $NO_2$, $OR^{a2}$ $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$ $NR^{c2}C(O)NR^{c2}R^{d2}$, $NR^{c2}C(O)OR^{a2}$, $NR^{c2}S(O)NR^{c2}R^{d2}$, $S(O)R^{b2}$, $S(O)NR^{c2}R^{d2}$, $S(O)_2R^{b2}$ $NR^{c2}S(O)_2R^{b2}$, and $S(O)_2 NR^{c2}R^{d2}$; $R^5$ is H, halo, $C_{1-6}$alkyl, $C_{2-6}$alkenyl, $C_{2-6}$alkynyl, $C_{1-6}$haloalkyl, $C_{1-6}$hydroxyalkyl, $C_{3-6}$cycloalkyl, aryl, heteroaryl, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)NR^{c1}R^{d1}$, $NR^{c1}C(O)OR^{a1}$, $NR^{c1}S(O)_2NR^{c1}R^{d1}$, $S(O)R^{b1}$, $S(O)NR^{c1}R^{d1}$, $S(O)_2R^{b1}$ $NR^{c1}S(O)_2R^{b1}$, or $S(O)_2NR^{c1}R^{d1}$, wherein each of $C_{1-6}$alkyl, $C_{2-6}$alkenyl, $C_{2-6}$alkynyl, $C_{1-6}$haloalkyl, $C_{1-6}$hydroxyalkyl, $C_{3-6}$cycloalkyl, aryl, and heteroaryl, is optionally substituted by 1, 2, 3, 4, or 5 substituents independently selected from halo, $C_{1-6}$alkyl, $C_{2-6}$alkenyl, $C_{2-6}$alkynyl, $C_{1-6}$haloalkyl, $C_{1-6}$hydroxyalkyl, $C_{3-6}$cycloalkyl, aryl, heteroaryl, CN, $NO_2$, $OR^{a2}$ $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$ $NR^{c2}C(O)NR^{c2}R^{d2}$, $NR^{c2}C(O)OR^{a2}$, $NR^{c2}S(O)NR^{c2}R^{d2}$, $S(O)R^{b2}$, $S(O)NR^{c2}R^{d2}$, $S(O)_2R^{b2}$ $NR^{c2}S(O)_2R^{b2}$, and $S(O)_2 NR^{c2}R^{d2}$; or two adjacent groups of $R^1$, $R^2$, $R^3$, $R^4$, and $R^5$ can link to form a fused cycloalkyl or fused heterocycloalkyl group, each optionally substituted by 1, 2, or 3 substituents independently selected from halo, $C_{1-6}$alkyl, $C_{2-6}$alkenyl, $C_{2-6}$alkynyl, $C_{1-6}$haloalkyl, $C_{1-6}$hydroxyalkyl, $C_{3-6}$cycloalkyl, aryl, heteroaryl, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$ $NR^{c2}C(O)NR^{c2}R^{d2}$, $NR^{c2}C(O)OR^{a2}$, $NR^{c2}S(O)NR^{c2}R^{d2}$, $S(O)R^{b2}$, $S(O)NR^{c2}R^{d2}$, $S(O)_2R^{b2}$ $NR^{c2}S(O)_2R^{b2}$, and $S(O)_2NR^{c2}R^{d2}$; $R^6$ is H, halo, $C_{1-6}$alkyl, $C_{2-6}$alkenyl, $C_{2-6}$alkynyl, $C_{1-6}$haloalkyl, $C_{1-6}$hydroxyalkyl, $C_{3-6}$cycloalkyl, aryl, heteroaryl, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)NR^{c1}R^{d1}$, $NR^{c1}C(O)OR^{a1}$, $NR^{c1}S(O)_2NR^{c1}R^{d1}$, $S(O)R^{b1}$, $S(O)NR^{c1}R^{d1}$, $S(O)_2R^{b1}$, $NR^{c1}S(O)_2R^{b1}$, or $S(O)_2NR^{c1}R^{d1}$, wherein each of $C_{1-6}$alkyl, $C_{2-6}$alkenyl, $C_{2-6}$alkynyl, $C_{1-6}$haloalkyl, $C_{1-6}$hydroxyalkyl, $C_{3-6}$cycloalkyl, aryl, and heteroaryl, is optionally substituted by 1, 2, 3, 4, or 5 substituents independently selected from halo, $C_{1-6}$alkyl, $C_{2-6}$alkenyl, $C_{2-6}$alkynyl, $C_{1-6}$haloalkyl, $C_{1-6}$hydroxyalkyl, $C_{3-6}$cycloalkyl, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$ $NR^{c2}C(O)NR^{c2}R^{d2}$, $NR^{c2}C(O)OR^{a2}$, $NR^{c2}S(O)NR^{c2}R^{d2}$, $S(O)R^{b2}$, $S(O)NR^{c2}R^{d2}$, $S(O)_2R^{b2}$ $NR^{c2}S(O)_2R^{b2}$, and $S(O)_2 NR^{c2}R^{d2}$; $R^7$ is H, $C_{1-6}$alkyl, $C_{1-6}$haloalkyl, C(O)R$^{b1}$, C(O)NR$^{c1}$R$^{d1}$, C(O)OR$^{a1}$, S(O)R$^{b1}$, S(O)NR$^{c1}$R$^{d1}$, S(O)$_2$R$^{b1}$, or S(O)$_2$NR$^{c1}$R$^{d1}$; R$^{a1}$, R$^{b1}$, R$^{c1}$, and R$^{d1}$ are each, independently, selected from H, C$_{1-6}$alkyl, C$_{1-6}$haloalkyl, C$_{1-6}$hydroxyalkyl, C$_{2-6}$alkenyl, C$_{2-6}$alkynyl, aryl, cycloalkyl, heteroaryl, heterocycloalkyl, arylalkyl, heteroarylalkyl, cycloalkylalkyl, and heterocycloalkylalkyl, wherein each of C$_{1-6}$alkyl, C$_{1-6}$haloalkyl, C$_{1-6}$hydroxyalkyl, C$_{2-6}$alkenyl, C$_{2-6}$alkynyl, aryl, cycloalkyl, heteroaryl, heterocycloalkyl, arylalkyl, heteroarylalkyl, cycloalkylalkyl, and heterocycloalkylalkyl is optionally substituted with 1, 2, 3, 4, or 5 substituents independently selected from OH, NO$_2$, CN, amino, halo, C$_{1-6}$alkyl, C$_{1-6}$alkoxy, C$_{1-6}$haloalkyl, C$_{1-6}$hydroxyalkyl, and C$_{1-6}$haloalkoxy; or R$^{c1}$ and R$^{d1}$ together with the N atom to which they are attached form a 4-, 5-, 6-, or 7-membered heterocycloalkyl group or heteroaryl group, each optionally substituted with 1, 2, or 3 substituents independently selected from OH, NO$_2$, CN, amino, halo, C$_{1-6}$alkyl, C$_{1-6}$alkoxy, C$_{1-6}$haloalkyl, C$_{1-6}$hydroxyalkyl, and C$_{1-6}$haloalkoxy; R$^{a2}$, R$^{d2}$, R$^{c2}$, and R are each, independently, selected from H, C$_{1-6}$alkyl, C$_{1-6}$haloalkyl, C$_{1-6}$hydroxyalkyl, C$_{2-6}$alkenyl, C$_{2-6}$alkynyl, aryl, cycloalkyl, heteroaryl, heterocycloalkyl, arylalkyl, heteroarylalkyl, cycloalkylalkyl, and heterocycloalkylalkyl, wherein each of C$_{1-6}$alkyl, C$_{1-6}$haloalkyl, C$_{1-6}$hydroxyalkyl, C$_{2-6}$alkenyl, C$_{2-6}$alkynyl, aryl, cycloalkyl, heteroaryl, heterocycloalkyl, arylalkyl, heteroarylalkyl, cycloalkylalkyl, or heterocycloalkylalkyl is optionally substituted with 1, 2, or 3 substituents independently selected from OH, NO$_2$, CN, amino, halo, C$_{1-6}$alkyl, C$_{1-6}$alkoxy, C$_{1-6}$haloalkyl, C$_{1-6}$hydroxyalkyl, and C$_{1-6}$haloalkoxy; or R$^{c2}$ and R$^{d2}$ together with the N atom to which they are attached form a 4-, 5-, 6-, or 7-membered heterocycloalkyl group or heteroaryl group, each optionally substituted with 1, 2, or 3 substituents independently selected from OH, NO$_2$, CN, amino, halo, C$_{1-6}$alkyl, C$_{1-6}$alkoxy, C$_{1-6}$haloalkyl, C$_{1-6}$hydroxyalkyl, and C$_{1-6}$haloalkoxy; Z$^1$ is O, S, or NR$^9$; R$^9$ is H, OH, C$_{1-6}$alkoxy, C$_{1-6}$haloalkyl, C$_{1-6}$hydroxyalkyl, aryloxy, heteroaryloxy, CN, or NO$_2$; Z$^2$ is O, S, or NR$^{10}$; R$^{10}$ is H, OH, C$_{1-6}$alkoxy, C$_{1-6}$haloalkyl, C$_{1-6}$hydroxyalkyl, aryloxy, heteroaryloxy, CN, or NO$_2$; L$^1$ is O, S, or NR$^{11}$; R$^{11}$ is H, C$_{1-6}$alkyl, C$_{1-6}$haloalkyl, C$_{1-6}$hydroxyalkyl, C(O)R$^{b1}$, C(O)NR$^{c1}$R$^{d1}$, C(O)OR$^{a1}$, S(O)R$^{b1}$, S(O)NR$^{c1}$R$^{d1}$, S(O)$_2$R$^{b1}$, or S(O)$_2$NR$^{c1}$R$^{d1}$; R$^{100}$ is a hydroxyl protecting group, C$_{1-6}$alkyl, C$_{2-6}$alkenyl, C$_{2-6}$alkynyl, C$_{1-6}$haloalkyl, C$_{1-6}$hydroxyalkyl, C$_{3-6}$cycloalkyl, heterocycloalkyl, aryl, heteroaryl, C(O)R$^b$, C(O)NR$^{c1}$R$^{d1}$, C(O)OR$^{a1}$, S(O)R$^{b1}$, S(O)NR$^{c1}$R$^{d1}$, S(O)$_2$R$^{b1}$, S(O)$_2$NR$^{c1}$R$^{d1}$, S(O)$_2$OR$^{e1}$, P(O)OR$^{f1}$OR$^{g1}$, or Si(R$^{h1}$)$_3$, wherein each of C$_{1-6}$alkyl, C$_{2-6}$alkenyl, C$_{2-6}$alkynyl, C$_{1-6}$haloalkyl, C$_{1-6}$hydroxyalkyl, C$_{3-6}$cycloalkyl, aryl, and heteroaryl, is optionally substituted by 1, 2, 3, 4 or 5 substituents independently selected from halo, C$_{1-6}$alkyl, C$_{2-6}$alkenyl, C$_{2-6}$alkynyl, C$_{1-6}$haloalkyl, C$_{1-6}$hydroxyalkyl, C$_{3-6}$cycloalkyl, aryl, heteroaryl, CN, NO$_2$, OR$^{a2}$, SR$^{a2}$, C(O)R$^{b2}$, C(O)NR$^{c2}$R$^{d2}$, C(O)OR$^{a2}$, OC(O)R$^{b2}$, OC(O)NR$^{c2}$R$^{d2}$, NR$^{c2}$R$^{d2}$, NR$^{c2}$C(O)R$^{b2}$, NR$^{c2}$C(O)NR$^{c2}$R$^{d2}$, NR$^{c2}$C(O)OR$^{a2}$, NR$^{c2}$S(O)NR$^{c2}$R$^{d2}$, S(O)R$^{b2}$, S(O)NR$^{c2}$R$^{d2}$, S(O)$_2$R$^{b2}$ NR$^{c2}$S(O)$_2$R$^{b2}$, and S(O)$_2$NR$^{c2}$R$^{d2}$; R$^{200}$ is a hydroxyl protecting group, C$_{1-6}$alkyl, C$_{2-6}$alkenyl, C$_{2-6}$alkynyl, C$_{1-6}$haloalkyl, C$_{1-6}$hydroxyalkyl, C$_{3-6}$cycloalkyl, heterocycloalkyl, aryl, heteroaryl, C(O)R$^{b1}$, C(O)NR$^{c1}$R$^{d1}$, C(O)OR$^{a1}$, S(O)R$^{b1}$, S(O)NR$^{c1}$R$^{d1}$, S(O)$_2$R$^{b1}$, S(O)$_2$NR$^{e1}$R$^{d1}$, S(O)$_2$OR$^e$, P(O)OR$^{f1}$OR$^{g1}$, or Si(R$^{h1}$)$_3$, wherein each of C$_{1-6}$alkyl, C$_{2-6}$alkenyl, C$_{2-6}$alkynyl, C$_{1-6}$haloalkyl, C$_{1-6}$hydroxyalkyl, C$_{3-6}$cycloalkyl, aryl, and heteroaryl, is optionally substituted by 1, 2, 3, 4 or 5 substituents independently selected from halo, C$_{1-6}$alkyl, C$_{2-6}$alkenyl, C$_{2-6}$alkynyl, C$_{1-6}$haloalkyl, C$_{1-6}$hydroxyalkyl, C$_{3-6}$cycloalkyl, aryl, heteroaryl, CN, NO$_2$, OR$^{a2}$, SR$^{a2}$, C(O)R$^{b2}$, C(O)NR$^{c2}$R$^{d2}$, C(O)OR$^{a2}$, OC(O)R$^{b2}$ OC(O)NR$^{c2}$R$^{d2}$, NR$^{c2}$R$^{d2}$, NR$^{c2}$C(O)R$^{b2}$, NR$^{c2}$C(O)NR$^{c2}$R$^{d2}$, NR$^{c2}$C(O)OR$^{a2}$ NR$^{c2}$S(O)NR$^{c2}$R$^{d2}$, S(O)R$^{b2}$, S(O)NR$^{c2}$R$^{d2}$, S(O)$_2$R$^{b2}$, NR$^{c2}$S(O)$_2$R$^{b2}$, and S(O)$_2$NR$^{c2}$R$^{d2}$; each R$^{c1}$ is, independently, H, C$_{1-6}$alkyl, C$_{1-6}$haloalkyl, C$_{1-6}$hydroxyalkyl, C$_{2-6}$alkenyl, C$_{2-6}$alkynyl, aryl, cycloalkyl, heteroaryl, heterocycloalkyl, cycloalkylalkyl, heterocycloalkylalkyl, arylalkyl, or heteroarylalkyl; each R$^f$ is, independently, H, C$_{1-6}$alkyl, C$_{1-6}$haloalkyl, C$_{1-6}$hydroxyalkyl, C$_{2-6}$alkenyl, (C$_{1-6}$alkoxy)-C$_{1-6}$alkyl, C$_{2-6}$alkynyl, aryl, cycloalkyl, heteroaryl, heterocycloalkyl, arylalkyl, cycloalkylalkyl, heteroarylalkyl, or heterocycloalkylalkyl; each R$^{91}$ is, independently, H, C$_{1-6}$alkyl, C$_{1-6}$haloalkyl, C$_{1-6}$hydroxyalkyl, C$_{2-6}$alkenyl, C$_{2-6}$alkynyl, aryl, cycloalkyl, heteroaryl, or heterocycloalkyl; and each R$^{h1}$ is, independently, H, C$_{1-6}$alkyl, C$_{1-6}$haloalkyl, C$_{1-6}$hydroxyalkyl, C$_{2-6}$alkenyl, C$_{2-6}$alkynyl, aryl, cycloalkyl, heteroaryl, heterocycloalkyl, cycloalkylalkyl, heterocycloalkylalkyl, arylalkyl, or heteroarylalkyl; or a pharmaceutically acceptable salt thereof.

In some embodiments, the TRPM8 agonist is menthol, icilin, WS 3, or WS 23. In some embodiments, the TRPM8 agonist is menthol.

The present disclosure also provides methods of reducing blood glucose levels, weight gain, or fat depot levels in a mammal in need thereof, comprising administering to the mammal an effective amount of a composition as described herein, or comprising administering a lyn kinase activator and a TRPM8 agonist.

The present disclosure also provides methods of treating metabolic syndrome, Syndrome X, obesity, prediabetes, type II diabetes, type I diabetes in a mammal in need thereof, comprising administering to the mammal an effective amount of a composition as described herein, or comprising administering a lyn kinase activator and a TRPM8 agonist.

The present disclosure also provides methods of treating hypercholesterolemia, hypertension, coronary heart disease, diabetic neuropathy, lipodystrophy, diabetic retinopathy, erectile dysfunction, kidney disease, dyslipidemia, dyslipoproteinemia, a peroxisome proliferator activated receptor-associated disorder, septicemia, a thrombotic disorder, or pancreatitis in a mammal in need thereof, comprising administering to the mammal an effective amount of a composition as described herein, or comprising administering a lyn kinase activator and a TRPM8 agonist.

The present disclosure also provides methods of inducing the beiging of adipocytes in a mammal in need thereof, comprising administering to the mammal an effective amount of a composition as described herein, or comprising administering a lyn kinase activator and a TRPM8 agonist.

The present disclosure also provides methods of preventing pancreatic beta cell degeneration, comprising administering to the mammal an effective amount of a composition as described herein, or comprising administering a lyn kinase activator and a TRPM8 agonist.

BRIEF DESCRIPTION OF THE DRAWINGS

FIG. 10 (panel b) shows a corresponding Western blot.

FIG. 13 shows that menthol by itself does effect insulin sensitization or glycemic control in a rodent oral glucose tolerance test, whereas menthol potentiates the insulin sensitizing action of Compound 102 in a rodent oral glucose tolerance test.

DESCRIPTION OF EMBODIMENTS

Figure 1:
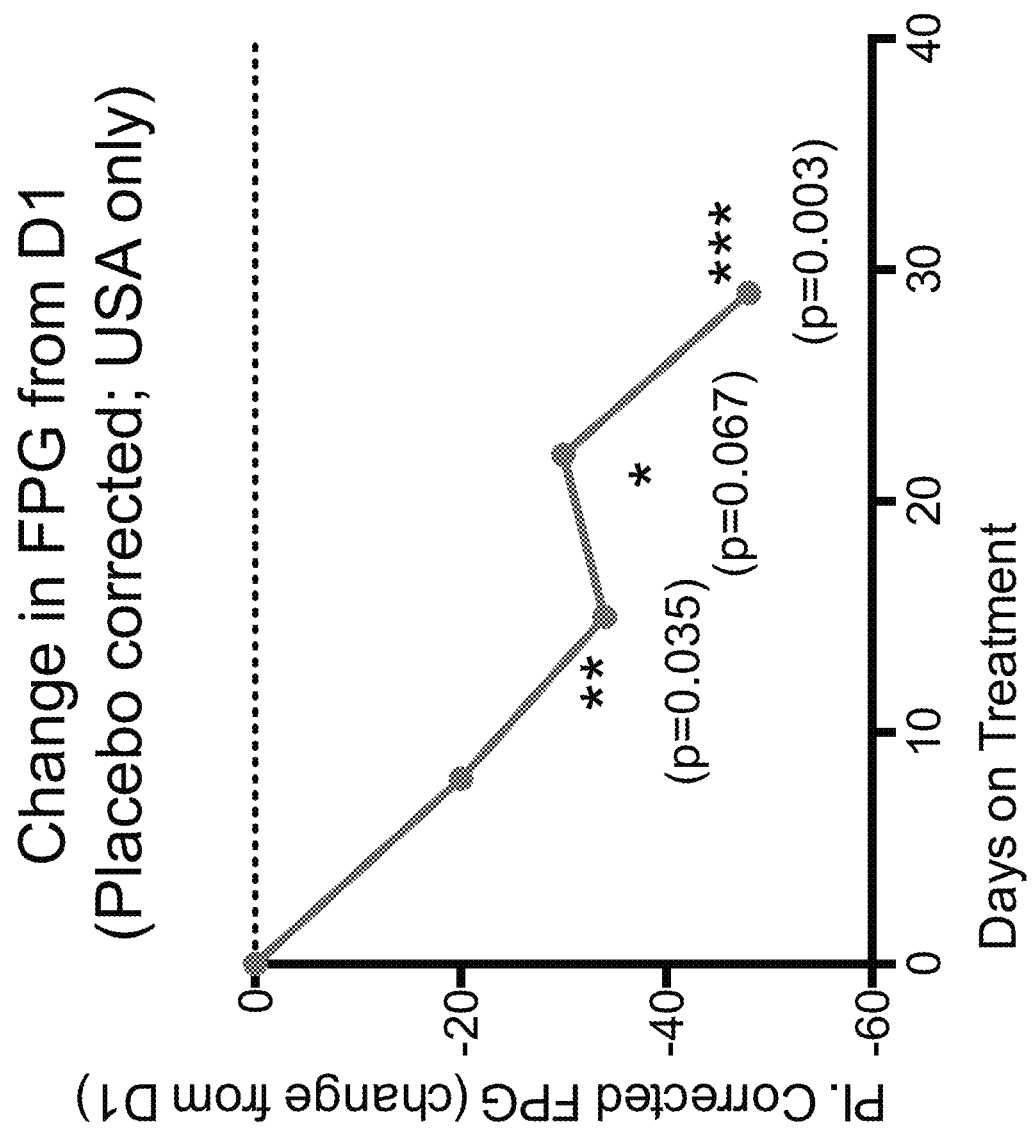
FIG. 1 shows the progressive reduction in fasting plasma glucose (FPG) upon treatment with Compound 102.

As used herein, the terms "a" or "an" means that "at least one" or "one or more" unless the context clearly indicates otherwise.

As used herein, the term "about" means that the numerical value is approximate and small variations would not significantly affect the practice of the disclosed embodiments. Where a numerical limitation is used, unless indicated otherwise by the context, "about" means the numerical value can vary by ±10% and remain within the scope of the disclosed embodiments.

As used herein, the term "alkoxy" means a straight or branched —O-alkyl group of 1 to 20 carbon atoms, including, but not limited to, methoxy, ethoxy, n-propoxy, isopropoxy, t-butoxy, and the like. In some embodiments, the alkoxy chain is from 1 to 10 carbon atoms in length, from 1 to 8 carbon atoms in length, from 1 to 6 carbon atoms in length, from 1 to 4 carbon atoms in length, from 2 to 10 carbon atoms in length, from 2 to 8 carbon atoms in length, from 2 to 6 carbon atoms in length, or from 2 to 4 carbon atoms in length. An alkoxy group can be unsubstituted or substituted with one or two suitable substituents.

As used herein, the term "alkyl" means a saturated hydrocarbon group which is straight-chained or branched. An alkyl group can contain from 1 to 20, from 2 to 20, from 1 to 10, from 2 to 10, from 1 to 8, from 2 to 8, from 1 to 6, from 2 to 6, from 1 to 4, from 2 to 4, from 1 to 3, or 2 or 3 carbon atoms. Examples of alkyl groups include, but are not limited to, methyl (Me), ethyl (Et), propyl (e.g., n-propyl and isopropyl), butyl (e.g., n-butyl, t-butyl, isobutyl), pentyl (e.g., n-pentyl, isopentyl, neopentyl), hexyl, isohexyl, heptyl, 4,4-dimethylpentyl, octyl, 2,2,4-trimethylpentyl, nonyl, decyl, undecyl, dodecyl, 2-methyl-1-propyl, 2-methyl-2-propyl, 2-methyl-1-butyl, 3-methyl-1-butyl, 2-methyl-3-butyl, 2-methyl-1-pentyl, 2,2-dimethyl-1-propyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, and the like. An alkyl group can be unsubstituted or substituted with one or two suitable substituents.

As used herein, the term "alkenyl" means a straight or branched alkyl group having one or more double carbon-carbon bonds and 2-20 carbon atoms, including, but not limited to, ethenyl, 1-propenyl, 2-propenyl, 2-methyl-1-propenyl, 1-butenyl, 2-butenyl, vinyl, allyl, pentenyl, hexenyl, butadienyl, pentadienyl, hexadienyl, 2-ethylhexenyl, 2-propyl-2-butenyl, 4-(2-methyl-3-butene)-pentenyl and the like. In some embodiments, the alkenyl chain is from 2 to 10 carbon atoms in length, from 2 to 8 carbon atoms in length, from 2 to 6 carbon atoms in length, or from 2 to 4 carbon atoms in length. The double bond of an alkenyl group can be unconjugated or conjugated to another unsaturated group. An alkenyl group can be unsubstituted or substituted with one or two suitable substituents.

As used herein, the term "alkynyl" means a straight or branched alkyl group having one or more triple carbon-carbon bonds and 2-20 carbon atoms, including, but not limited to, acetylene, 1-propylene, 2-propylene, ethynyl, propynyl, butynyl, pentynyl, hexynyl, methylpropynyl, 4-methyl-1-butynyl, 4-propyl-2-pentynyl, and 4-butyl-2-hexynyl, and the like. In some embodiments, the alkynyl chain is 2 to 10 carbon atoms in length, from 2 to 8 carbon atoms in length, from 2 to 6 carbon atoms in length, or from 2 to 4 carbon atoms in length. The triple bond of an alkynyl group can be unconjugated or conjugated to another unsaturated group. An alkynyl group can be unsubstituted or substituted with one or two suitable substituents.

As used herein, the term "animal" includes, but is not limited to, humans and non-human vertebrates such as wild, domestic, and farm animals.

As used herein, the term "aryl" means a monocyclic, bicyclic, or polycyclic (e.g., having 2, 3 or 4 fused rings) aromatic hydrocarbons. In some embodiments, aryl groups have from 6 to 20 carbon atoms or from 6 to 10 carbon atoms. Examples of aryl groups include, but are not limited to, phenyl, naphthyl, anthracenyl, phenanthrenyl, indanyl, indenyl, tetrahydronaphthyl, tolyl, fluorenyl, azulenyl, naphthyl, 5,6,7,8-tetrahydronaphthyl, and the like. An aryl group can be unsubstituted or substituted with one or two suitable substituents.

As used herein, the term "aryloxy" means an —O-aryl group, wherein aryl is as defined herein. An aryloxy group can be unsubstituted or substituted with one or two suitable substituents. The aryl ring of an aryloxy group can be a monocyclic ring, wherein the ring comprises 6 carbon atoms, referred to herein as "$(C_6)$aryloxy."

As used herein, the term "benzyl" means —CH$_2$-phenyl.

As used herein, the term "carbocycle" means a 5- or 6-membered, saturated or unsaturated cyclic ring, optionally containing O, S, or N atoms as part of the ring. Examples of carbocycles include, but are not limited to, cyclopentyl, cyclohexyl, cyclopenta-1,3-diene, phenyl, and any of the heterocycles recited herein.

As used herein, the term "carbonyl" group is a divalent group of the formula —C(O)—.

As used herein, the term "carrier" means a diluent, adjuvant, or excipient with which a compound is administered. Pharmaceutical carriers can be liquids, such as water and oils, including those of petroleum, animal, vegetable or synthetic origin, such as peanut oil, soybean oil, mineral oil, sesame oil and the like. The pharmaceutical carriers can also be saline, gum acacia, gelatin, starch paste, talc, keratin, colloidal silica, urea, and the like. In addition, auxiliary, stabilizing, thickening, lubricating and coloring agents can be used.

As used herein, the term, "compound" means all stereoisomers, tautomers, and isotopes of the compounds described herein.

As used herein, the terms "comprising" (and any form of comprising, such as "comprise", "comprises", and "comprised"), "having" (and any form of having, such as "have" and "has"), "including" (and any form of including, such as "includes" and "include"), or "containing" (and any form of containing, such as "contains" and "contain"), are inclusive or open-ended and do not exclude additional, unrecited elements or method steps.

As used herein, the term "cycloalkyl" means non-aromatic cyclic hydrocarbons including cyclized alkyl, alkenyl, and alkynyl groups that contain up to 20 ring-forming carbon atoms. Cycloalkyl groups can include mono- or polycyclic ring systems such as fused ring systems, bridged ring systems, and spiro ring systems. In some embodiments, polycyclic ring systems include 2, 3, or 4 fused rings. A cycloalkyl group can contain from 3 to 15, from 3 to 10, from 3 to 8, from 3 to 6, from 4 to 6, from 3 to 5, or 5 or 6 ring-forming carbon atoms. Ring-forming carbon atoms of a cycloalkyl group can be optionally substituted by oxo or sulfido. Examples of cycloalkyl groups include, but are not limited to, cyclopropyl, cyclobutyl, cyclopentyl, cyclohexyl, cycloheptyl, cyclooctyl, cyclononyl, cyclopentenyl, cyclohexenyl, cyclohexadienyl, cycloheptatrienyl, norbornyl, norpinyl, norcarnyl, adamantyl, and the like. Also included in the definition of cycloalkyl are moieties that have one or more aromatic rings fused (having a bond in common with) to the cycloalkyl ring, for example, benzo or thienyl derivatives of pentane, pentene, hexane, and the like (e.g., 2,3-dihydro-1H-indene-1-yl, or 1H-inden-2(3H)-one-1-yl). A cycloalkyl group can be unsubstituted or substituted by one or two suitable substituents.

As used herein, the term "halogen" means fluorine, chlorine, bromine, or iodine. Correspondingly, the meaning of the terms "halo" and "Hal" encompass fluoro, chloro, bromo, and iodo.

As used herein, the term "heteroaryl" means an aromatic heterocycle having up to ring-forming atoms (e.g., C) and having at least one heteroatom ring member (ring-forming atom) such as sulfur, oxygen, or nitrogen. In some embodiments, the heteroaryl group has at least one or more heteroatom ring-forming atoms, each of which are, independently, sulfur, oxygen, or nitrogen. In some embodiments, the heteroaryl group has from 3 to 20 ring-forming atoms, from 3 to 10 ring-forming atoms, from 3 to 6 ring-forming atoms, or from 3 to 5 ring-forming atoms. In some embodiments, the heteroaryl group contains 2 to 14 carbon atoms, from 2 to 7 carbon atoms, 2 to 5 carbon atoms, or 5 or 6 carbon atoms. In some embodiments, the heteroaryl group has 1 to 4 heteroatoms, 1 to 3 heteroatoms, or 1 or 2 heteroatoms. Heteroaryl groups include monocyclic and polycyclic (e.g., having 2, 3 or 4 fused rings) systems. Examples of heteroaryl groups include, but are not limited to, pyridyl, pyrimidinyl, pyrazinyl, pyridazinyl, triazinyl, furyl, quinolyl, isoquinolyl, thienyl, imidazolyl, thiazolyl, indolyl (such as indol-3-yl), pyrryl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, benzothienyl, purinyl, carbazolyl, benzimidazolyl, indolinyl, pyranyl, oxadiazolyl, isoxazolyl, triazolyl, thianthrenyl, pyrazolyl, indolizinyl, isoindolyl, isobenzofuranyl, benzoxazolyl, xanthenyl, 2H-pyrrolyl, pyrrolyl, 3H-indolyl, 4H-quinolizinyl, phthalazinyl, naphthyridinyl, quinazolinyl, phenanthridinyl, acridinyl, perimidinyl, phenanthrolinyl, phenazinyl, isothiazolyl, phenothiazinyl, isoxazolyl, furazanyl, phenoxazinyl, pyrazyl, phienyl, groups, and the like. Suitable heteroaryl groups include 1,2,3-triazole, 1,2,4-triazole, 5-amino-1,2,4-triazole, imidazole, oxazole, isoxazole, 1,2,3-oxadiazole, 1,2,4-oxadiazole, 3-amino-1,2,4-oxadiazole, 1,2,5-oxadiazole, 1,3,4-oxadiazole, pyridine, and 2-aminopyridine. A heteroaryl group can be unsubstituted or substituted with one or two suitable substituents.

As used herein, the term "heterocycle" or "heterocyclic ring" means a 5- to 7-membered mono- or bicyclic or 7- to 10-membered bicyclic heterocyclic ring system any ring of which may be saturated or unsaturated, and which consists of carbon atoms and from one to three heteroatoms chosen from N, O and S, and wherein the N and S heteroatoms may optionally be oxidized, and the N heteroatom may optionally be quaternized, and including any bicyclic group in which any of the above-defined heterocyclic rings is fused to a benzene ring. Particularly useful are rings containing one oxygen or sulfur, one to three nitrogen atoms, or one oxygen or sulfur combined with one or two nitrogen atoms. The heterocyclic ring may be attached at any heteroatom or carbon atom which results in the creation of a stable structure. Examples of heterocyclic groups include, but are not limited to, piperidinyl, piperazinyl, 2-oxopiperazinyl, 2-oxopiperidinyl, 2-oxopyrrolodinyl, 2-oxoazepinyl, azepinyl, pyrrolyl, 4-piperidonyl, pyrrolidinyl, pyrazolyl, pyrazolidinyl, imidazolyl, imidazolinyl, imidazolidinyl, pyridyl, pyrazinyl, pyrimidinyl, pyridazinyl, oxazolyl, oxazolidinyl, isoxazolyl, isoxazolidinyl, morpholinyl, thiazolyl, thiazolidinyl, isothiazolyl, quinuclidinyl, isothiazolidinyl, indolyl, quinolinyl, isoquinolinyl, benzimidazolyl, thiadiazoyl, benzopyranyl, benzothiazolyl, benzoxazolyl, furyl, tetrahydrofuryl, tetrahydropyranyl, thienyl, benzothienyl, thiamorpholinyl, thiamorpholinyl sulfoxide, thiamorpholinyl sulfone, and oxadiazolyl. Morpholino is the same as morpholinyl.

As used herein, the term "heterocycloalkyl" means non-aromatic heterocycles having up to 20 ring-forming atoms including cyclized alkyl, alkenyl, and alkynyl groups, where one or more of the ring-forming carbon atoms is replaced by a heteroatom such as an O, N, or S atom. Hetercycloalkyl groups can be mono or polycyclic (e.g., fused, bridged, or spiro systems). In some embodiments, the heterocycloalkyl group has from 1 to 20 carbon atoms, or from 3 to 20 carbon atoms. In some embodiments, the heterocycloalkyl group contains 3 to 14 ring-forming atoms, 3 to 7 ring-forming atoms, or 5 or 6 ring-forming atoms. In some embodiments, the heterocycloalkyl group has 1 to 4 heteroatoms, 1 to 3 heteroatoms, or 1 or 2 heteroatoms. In some embodiments, the heterocycloalkyl group contains 0 to 3 double bonds. In some embodiments, the heterocycloalkyl group contains 0 to 2 triple bonds. Examples of heterocycloalkyl groups include, but are not limited to, morpholino, thiomorpholino, piperazinyl, tetrahydrofuranyl, tetrahydrothienyl, 2,3-dihydrobenzofuryl, 1,3-benzodioxole, benzo-1,4-dioxane, piperidinyl, pyrrolidinyl, isoxazolidinyl, oxazolidinyl, isothiazolidinyl, pyrazolidinyl, thiazolidinyl, imidazolidinyl, pyrrolidino, piperidino, morpholinyl, thiomorpholinyl, pyranyl, pyrrolidin-2-one-3-yl, and the like. In addition, ring-forming carbon atoms and heteroatoms of a heterocycloalkyl group can be optionally substituted by oxo or sulfido. For example, a ring-forming S atom can be substituted by 1 or 2 oxo (form a $S(O)$ or $S(O)_2$). For another example, a ring-forming C atom can be substituted by oxo (form carbonyl). Also included in the definition of heterocycloalkyl are moieties that have one or more aromatic rings fused (having a bond in common with) to the nonaromatic heterocyclic ring including, but not limited to, pyridinyl, thiophenyl, phthalimidyl, naphthalimidyl, and benzo derivatives of heterocycles such as indolene, isoindolene, isoindolin-1-one-3-yl, 4,5,6,7-tetrahydrothieno[2,3-c]pyridine-5-yl, 5,6-dihydrothieno[2,3-c]pyridin-7(4H)-one-5-yl, and 3,4-dihydroisoquinolin-1(2H)-one-3yl groups. Ring-forming carbon atoms and heteroatoms of the heterocycloalkyl group can be optionally substituted by oxo or sulfido. A heterocycloalkyl group can be unsubstituted or substituted with one or two suitable substituents.

As used herein, the term "hydrocarbyl group" means a monovalent group selected from $(C_1-C_8)$alkyl, $(C_2-C_8)$alkenyl, and $(C_2-C_8)$alkynyl, optionally substituted with one or two suitable substituents. In some embodiments, the hydrocarbon chain of a hydrocarbyl group is from 1 to 6 carbon atoms in length, referred to herein as "$(C_1-C_6)$hydrocarbyl."

As used herein, the term "individual" or "patient," used interchangeably, means any animal, including mammals, such as mice, rats, other rodents, rabbits, dogs, cats, swine, cattle, sheep, horses, or primates, such as humans.

As used herein, the phrase "in need thereof" means that the animal or mammal has been identified as having a need for the particular method or treatment. In some embodiments, the identification can be by any means of diagnosis. In any of the methods and treatments described herein, the animal or mammal can be in need thereof.

As used herein, the phrase "integer from 1 to 5" means 1, 2, 3, 4, or 5.

As used herein, the term "mammal" means a rodent (i.e., a mouse, a rat, or a guinea pig), a monkey, a cat, a dog, a cow, a horse, a pig, or a human. In some embodiments, the mammal is a human.

As used herein, the term "modulate" refers to a change in the expression and/or activity of a protein. In an illustrative embodiment, "modulate" refers to increase or decrease the expression and/or activity of a protein.

As used herein, the term "n-membered", where n is an integer, typically describes the number of ring-forming atoms in a moiety, where the number of ring-forming atoms is n. For example, pyridine is an example of a 6-membered heteroaryl ring and thiophene is an example of a 5-membered heteroaryl ring.

As used herein, the phrase "optionally substituted" means that substitution is optional and therefore includes both unsubstituted and substituted atoms and moieties. A "substituted" atom or moiety indicates that any hydrogen on the designated atom or moiety can be replaced with a selection from the indicated substituent groups, provided that the normal valency of the designated atom or moiety is not exceeded, and that the substitution results in a stable compound. For example, if a methyl group is optionally substituted, then 3 hydrogen atoms on the carbon atom can be replaced with substituent groups.

As used herein, the phrase "pharmaceutically acceptable" means those compounds, materials, compositions, and/or dosage forms which are, within the scope of sound medical judgment, suitable for use in contact with tissues of humans and animals. In some embodiments, "pharmaceutically acceptable" means approved by a regulatory agency of the Federal or a state government or listed in the U.S. Pharmacopeia or other generally recognized pharmacopeia for use in animals, and more particularly in humans.

As used herein, the phrase "pharmaceutically acceptable salt(s)," includes, but is not limited to, salts of acidic or basic groups. Compounds that are basic in nature are capable of forming a wide variety of salts with various inorganic and organic acids. Acids that may be used to prepare pharmaceutically acceptable acid addition salts of such basic compounds are those that form non-toxic acid addition salts, i.e., salts containing pharmacologically acceptable anions including, but not limited to, sulfuric, thiosulfuric, citric, maleic, acetic, oxalic, hydrochloride, hydrobromide, hydroiodide, nitrate, sulfate, bisulfate, bisulfite, phosphate, acid phosphate, isonicotinate, borate, acetate, lactate, salicylate, citrate, acid citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate, bicarbonate, malonate, mesylate, esylate, napsydisylate, tosylate, besylate, orthophoshate, trifluoroacetate, and pamoate (i.e., 1,1'-methylene-bis-(2-hydroxy-3-naphthoate)) salts. Compounds that include an amino moiety may form pharmaceutically acceptable salts with various amino acids, in addition to the acids mentioned above. Compounds that are acidic in nature are capable of forming base salts with various pharmacologically acceptable cations. Examples of such salts include, but are not limited to, alkali metal or alkaline earth metal salts and, particularly, calcium, magnesium, ammonium, sodium, lithium, zinc, potassium, and iron salts. The present invention also includes quaternary ammonium salts of the compounds described herein, where the compounds have one or more tertiary amine moiety.

As used herein, the term "phenyl" means —$C_6H_5$. A phenyl group can be unsubstituted or substituted with one, two, or three suitable substituents.

As used herein, the terms "prevention" or "preventing" mean a reduction of the risk of acquiring a particular disease, condition, or disorder.

As used herein, the phrase "suitable substituent" or "substituent" means a group that does not nullify the synthetic or pharmaceutical utility of the compounds described herein or the intermediates useful for preparing them. Examples of suitable substituents include, but are not limited to: $C_1-C_6$alkyl, $C_1-C_6$alkenyl, $C_1-C_6$alkynyl, $C_5-C_6$aryl, $C_1-C_6$alkoxy, $C_3-C_5$heteroaryl, $C_3-C_6$cycloalkyl, $C_5-C_6$aryloxy, —CN, —OH, oxo, halo, haloalkyl, —$NO_2$, —$CO_2H$, —$NH_2$, —NH($C_1-C_5$alkyl), —N($C_1-C_5$alkyl)$_2$, —NH($C_6$aryl), —N($C_5-C_6$aryl)$_2$, —CHO, —CO($C_1$-$C_6$alkyl), —CO(($C_5-C_6$)aryl), —$CO_2$(($C_1-C_6$)alkyl), and —$CO_2$(($C_5-C_6$)aryl). One of skill in art can readily choose a suitable substituent based on the stability and pharmacological and synthetic activity of the compounds described herein.

As used herein, the phrase "therapeutically effective amount" means the amount of active compound or pharmaceutical agent that elicits the biological or medicinal response that is being sought in a tissue, system, animal, individual or human by a researcher, veterinarian, medical doctor or other clinician. The therapeutic effect is dependent upon the disorder being treated or the biological effect desired. As such, the therapeutic effect can be a decrease in the severity of symptoms associated with the disorder and/or inhibition (partial or complete) of progression of the disorder, or improved treatment, healing, prevention or elimination of a disorder, or side-effects, or at least one adverse effect of a disorder is ameliorated or alleviated. The amount needed to elicit the therapeutic response can be determined based on the age, health, size and sex of the subject. Optimal amounts can also be determined based on monitoring of the subject's response to treatment.

As used herein, the terms "treat," "treated," or "treating" mean therapeutic treatment measures wherein the object is to slow down (lessen) an undesired physiological condition, disorder or disease, or obtain beneficial or desired clinical results. Beneficial or desired clinical results include, but are not limited to, alleviation of symptoms; diminishment of extent of condition, disorder or disease; stabilized (i.e., not worsening) state of condition, disorder or disease; delay in onset or slowing of condition, disorder or disease progression; amelioration of the condition, disorder or disease state or remission (whether partial or total), whether detectable or undetectable; an amelioration of at least one measurable physical parameter, not necessarily discernible by the patient; or enhancement or improvement of condition, disorder or disease. Treatment may include eliciting a clinically significant response without excessive levels of side effects. Treatment may also include prolonging survival as compared to expected survival if not receiving treatment.

The compounds of the disclosure are identified herein by their chemical structure and/or chemical name. Where a compound is referred to by both a chemical structure and a chemical name, and that chemical structure and chemical name conflict, the chemical structure is determinative of the compound's identity.

At various places in the present specification, substituents of compounds may be disclosed in groups or in ranges. It is specifically intended that the invention include each and every individual subcombination of the members of such groups and ranges. For example, the term "$C_{1-6}$alkyl" is specifically intended to individually disclose methyl, ethyl, propyl, $C_4$alkyl, $C_5$alkyl, and $C_6$alkyl, linear and/or branched.

For compounds in which a variable appears more than once, each variable can be a different moiety selected from the Markush group defining the variable. For example, where a structure is described having two R groups that are simultaneously present on the same compound, the two R groups can represent different moieties selected from the Markush groups defined for R. In another example, when an optionally multiple substituent is designated in the form, for example,

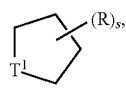

then it is understood that substituent R can occur "s" number of times on the ring, and R can be a different moiety at each occurrence. Further, in the above example, where the variable $T^1$ is defined to include hydrogens, such as when $T^1$ is $CH_2$, NH, etc., any H can be replaced with a substituent.

It is further appreciated that certain features of the disclosure, which are, for clarity, described in the context of separate embodiments, can also be provided in combination in a single embodiment. Conversely, various features of the disclosure which are, for brevity, described in the context of a single embodiment, can also be provided separately or in any suitable sub-combination.

It is understood that the present disclosure encompasses the use, where applicable, of stereoisomers, diastereomers and optical stereoisomers of the compounds of the disclosure, as well as mixtures thereof. Additionally, it is understood that stereoisomers, diastereomers, and optical stereoisomers of the compounds of the disclosure, and mixtures thereof, are within the scope of the disclosure. By way of non-limiting example, the mixture may be a racemate or the mixture may comprise unequal proportions of one particular stereoisomer over the other. Additionally, the compounds can be provided as a substantially pure stereoisomers, diastereomers and optical stereoisomers (such as epimers).

The compounds described herein may be asymmetric (e.g., having one or more stereocenters). All stereoisomers, such as enantiomers and diastereomers, are intended to be included within the scope of the disclosure unless otherwise indicated. Compounds that contain asymmetrically substituted carbon atoms can be isolated in optically active or racemic forms. Methods of preparation of optically active forms from optically active starting materials are known in the art, such as by resolution of racemic mixtures or by stereoselective synthesis. Many geometric isomers of olefins, C═N double bonds, and the like can also be present in the compounds described herein, and all such stable isomers are contemplated in the present disclosure. Cis and trans geometric isomers of the compounds are also included within the scope of the disclosure and can be isolated as a mixture of isomers or as separated isomeric forms. Where a compound capable of stereoisomerism or geometric isomerism is designated in its structure or name without reference to specific R/S or cis/trans configurations, it is intended that all such isomers are contemplated.

Resolution of racemic mixtures of compounds can be carried out by any of numerous methods known in the art, including, for example, fractional recrystallizaion using a chiral resolving acid which is an optically active, salt-forming organic acid. Suitable resolving agents for fractional recrystallization methods include, but are not limited to, optically active acids, such as the D and L forms of tartaric acid, diacetyltartaric acid, dibenzoyltartaric acid, mandelic acid, malic acid, lactic acid, and the various optically active camphorsulfonic acids such as β-camphorsulfonic acid. Other resolving agents suitable for fractional crystallization methods include, but are not limited to, stereoisomerically pure forms of α-methylbenzylamine (e.g., S and R forms, or diastereomerically pure forms), 2-phenylglycinol, norephedrine, ephedrine, N-methylephedrine, cyclohexylethylamine, 1,2-diaminocyclohexane, and the like. Resolution of racemic mixtures can also be carried out by elution on a column packed with an optically active resolving agent (e.g., dinitrobenzoylphenylglycine). Suitable elution solvent compositions can be determined by one skilled in the art.

Compounds may also include tautomeric forms. Tautomeric forms result from the swapping of a single bond with an adjacent double bond together with the concomitant migration of a proton. Tautomeric forms include prototropic tautomers which are isomeric protonation states having the same empirical formula and total charge. Examples of prototropic tautomers include, but are not limited to, ketone-enol pairs, amide-imidic acid pairs, lactam-lactim pairs, amide-imidic acid pairs, enamine-imine pairs, and annular forms where a proton can occupy two or more positions of a heterocyclic system including, but not limited to, 1H- and 3H-imidazole, 1H-, 2H- and 4H-1,2,4-triazole, 1H- and 2H-isoindole, and 1H- and 2H-pyrazole. Tautomeric forms can be in equilibrium or sterically locked into one form by appropriate substitution.

Compounds also include hydrates and solvates, as well as anhydrous and non-solvated forms.

Compounds can also include all isotopes of atoms occurring in the intermediates or final compounds. Isotopes include those atoms having the same atomic number but different mass numbers. For example, isotopes of hydrogen include tritium and deuterium.

In some embodiments, the compounds, or pharmaceutically acceptable salts thereof, are substantially isolated. Partial separation can include, for example, a composition enriched in the compound of the disclosure. Substantial separation can include compositions containing at least about 50%, at least about 60%, at least about 70%, at least about 80%, at least about 90%, at least about 95%, at least about 97%, or at least about 99% by weight of the compound of the disclosure, or pharmaceutically acceptable salt thereof. Methods for isolating compounds and their salts are routine in the art.

Although the disclosed compounds are suitable, other functional groups can be incorporated into the compound with an expectation of similar results. In particular, thioamides and thioesters are anticipated to have very similar properties. The distance between aromatic rings can impact the geometrical pattern of the compound and this distance can be altered by incorporating aliphatic chains of varying length, which can be optionally substituted or can comprise an amino acid, a dicarboxylic acid or a diamine. The distance between and the relative orientation of monomers within the compounds can also be altered by replacing the amide bond with a surrogate having additional atoms. Thus, replacing a carbonyl group with a dicarbonyl alters the distance between the monomers and the propensity of dicarbonyl unit to adopt an anti arrangement of the two carbonyl moiety and alter the periodicity of the compound. Pyromellitic anhydride represents still another alternative to simple amide linkages which can alter the conformation and physical properties of the compound. Modern methods of solid phase organic chemistry (E. Atherton and R. C. Sheppard, Solid Phase Peptide Synthesis A Practical Approach IRL Press Oxford 1989) now allow the synthesis of homodisperse compounds with molecular weights approaching 5,000 Daltons. Other substitution patterns are equally effective.

The compounds described herein also include derivatives referred to as prodrugs, which can be prepared by modifying functional groups present in the compounds in such a way that the modifications are cleaved, either in routine manipulation or in vivo, to the parent compounds. Examples of prodrugs include compounds as described herein that contain one or more molecular moieties appended to a hydroxyl, amino, sulfhydryl, or carboxyl group of the compound, and that when administered to a patient, cleaves in vivo to form the free hydroxyl, amino, sulfhydryl, or carboxyl group, respectively. Examples of prodrugs include, but are not limited to, acetate, formate and benzoate derivatives of alcohol and amine functional groups in the compounds described herein. Preparation and use of prodrugs is discussed in T. Higuchi et al., "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987, both of which are incorporated herein by reference in their entireties.

Compounds containing an amine function can also form N-oxides. A reference herein to a compound that contains an amine function also includes the N-oxide. Where a compound contains several amine functions, one or more than one nitrogen atom can be oxidized to form an N-oxide. Examples of N-oxides include N-oxides of a tertiary amine or a nitrogen atom of a nitrogen-containing heterocycle. N-Oxides can be formed by treatment of the corresponding amine with an oxidizing agent such as hydrogen peroxide or a per-acid (e.g., a peroxycarboxylic acid) (see, Advanced Organic Chemistry, by Jerry March, 4th Edition, Wiley Interscience).

The present disclosure provides compositions comprising one or more lyn kinase activators, or pharmaceutically acceptable salts thereof, and a TRPM8 agonist.

In some embodiments, the lyn kinase activator is of the formula:

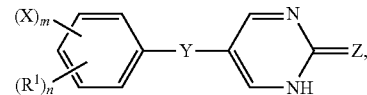

wherein: $R^1$ is an alkyl group; X is a halogen; Y is O, S, or NH; Z is O or S; and n is an integer from 0 to 5 and m is 0 or 1, wherein m+n is less than or equal to 5; or a pharmaceutically acceptable salt thereof.

In some embodiments, the alkyl group is methyl and n is 1. In some embodiments, the halogen is chlorine and m is 1. In some embodiments, Y is O. In some embodiments, Z is 0. In some embodiments, R is methyl, Y is O, Z is O, n is 1, and m is 0. In some embodiments, $R^1$ is in the meta position. In some embodiments, X is chlorine, Y is O, Z is 0, n is O, and m is 1. In some embodiments, X is in the meta position.

In some embodiments, the lyn kinase activator is of the formula:

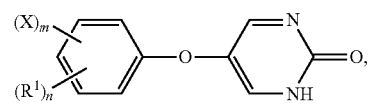

wherein: $R^1$ is an alkyl group; X is a halogen; and n is an integer from 0 to 5 and m is 0 or 1, wherein m+n is less than or equal to 5; or a pharmaceutically acceptable salt thereof.

In some embodiments, the alkyl group is methyl and n is 1. In some embodiments, the halogen is chlorine and m is 1. In some embodiments, $R^1$ is methyl, n is 1, and m is 0. In some embodiments, $R^1$ is in the meta position. In some embodiments, X is chlorine, n is O, and m is 1. In some embodiments, X is in the meta position.

In some embodiments, the lyn kinase activator is of the formula:

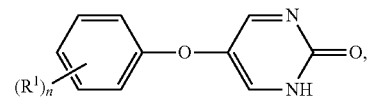

wherein $R^1$ is an alkyl group and n is an integer from 0 to 5; or a pharmaceutically acceptable salt thereof.

In some embodiments, $R^1$ is methyl, n is 1. In some embodiments, $R^1$ is in the meta position.

In some embodiments, the lyn kinase activator is of the formula:

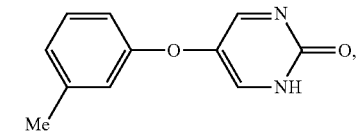

or a pharmaceutically acceptable salt thereof.

In some embodiments, the lyn kinase activator is of the formula:

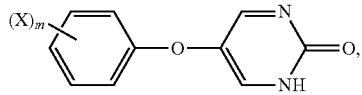

wherein X is a halogen and m is an integer from 0 to 1; or a pharmaceutically acceptable salt thereof. In some embodiments, X is chloro and m is 1. In some embodiments, X is in the meta position.

In some embodiments, the lyn kinase activator is of the formula:

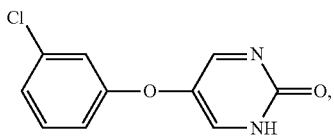

or a pharmaceutically acceptable salt thereof.

In some embodiments, the lyn kinase activator is of the formula:

(Compound 101)
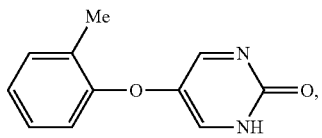

(Compound 102; MLR-1023)
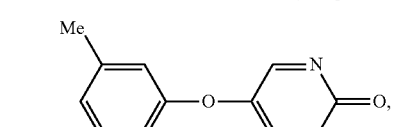

(Compound 103)
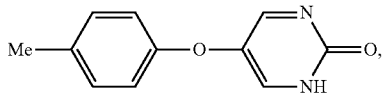

(Compound 104)
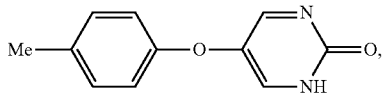

(Compound 105)
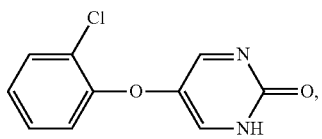

(Compound 106)
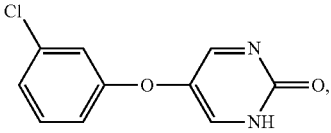 [SMILES: O=c1ncc(Oc2cccc(Cl)c2)c[nH]1]

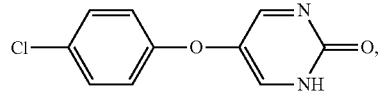

(Compound 107)
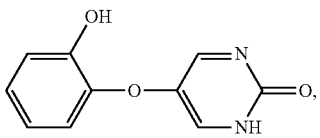

(Compound 108)
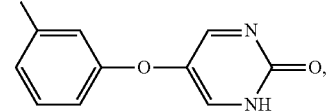

(Compound 109)
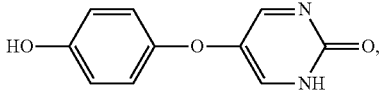

(Compound 110)
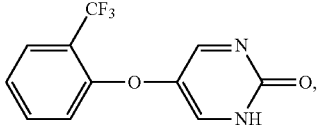

(Compound 111)
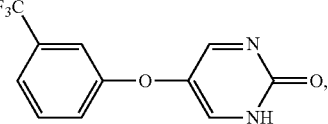

(Compound 112)
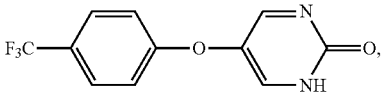

(Compound 113)
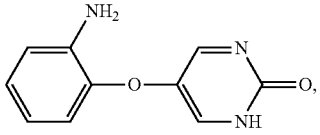

(Compound 114)
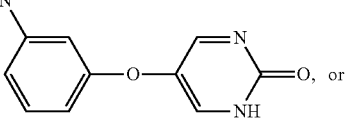

(Compound 115)
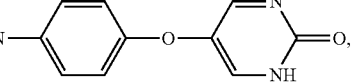

or a pharmaceutically acceptable salt thereof

In some embodiments, the lyn kinase activator is of the formula:

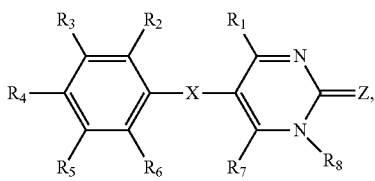

wherein:
each of $R_1$, $R_2$, $R_3$, $R_4$, $R_5$, $R_6$, and $R_7$ are, independently, a hydrogen, alkoxy, alkyl, alkenyl, alkynyl, aryl, aryloxy, benzyl, cycloalkyl, halogen, heteroaryl, heterocycloalkyl, —CN, —OH, —NO$_2$, —CF$_3$, —CO$_2$H, —CO$_2$alkyl, or —NH$_2$;

$R_8$ is an alkyl or hydrogen;

X is O, S, NH, or N-akyl; and

Z is O or S;

or a pharmaceutically acceptable salt thereof.

In some embodiments, $R_8$ is alkyl. In some embodiments, $R_8$ is methyl. In some embodiments, $R_8$ is hydrogen. In some embodiments, X is oxygen. In some embodiments, Z is oxygen. In some embodiments, at least one of $R_2$-$R_6$ is alkyl. In some embodiments, at least one of $R_2$-$R_6$ is methyl. In some embodiments, at least one of $R_2$-$R_6$ is halogen. In some embodiments, at least one of $R_2$-$R_6$ is chloro. In some embodiments, at least one of $R_2$-$R_6$ is —CN, —OH, —NO$_2$, —CF$_3$, —CO$_2$H, —NH$_2$, or alkoxy. In some embodiments, $R_2$ is alkyl, each of $R_1$ and $R_3$-$R_8$ is hydrogen, and X and Z are O. In some embodiments, $R_2$ is methyl. In some embodiments, $R_2$ is a halogen, each of $R_1$ and $R_3$-$R_8$ is hydrogen, and X and Z are O. In some embodiments, $R_2$ is chloro. In some embodiments, $R_3$ is alkyl, each of $R_1$, $R_2$ and $R_4$-$R_8$ is hydrogen, and X and Z are O. In some embodiments, $R_3$ is methyl. In some embodiments, $R_3$ is a halogen, each of $R_1$, $R_2$, and $R_4$-$R_8$ is hydrogen, and X and Z are O. In some embodiments, $R_3$ is chloro. In some embodiments, $R_4$ is alkyl, each of $R_1$-$R_3$ and $R_5$-$R_8$ is hydrogen, and X and Z are O. In some embodiments, $R_4$ is methyl. In some embodiments, $R_4$ is a halogen, each of $R_1$-$R_3$ and $R_5$-$R_8$ is hydrogen, and X and Z are O. In some embodiments, $R_4$ is chloro. In some embodiments, $R_5$ is —CF$_3$, each of $R_1$-$R_4$ and $R_6$-$R_8$ is hydrogen, and X and Z are O. In some embodiments, $R_5$ is —NH$_2$, each of $R_1$-$R_4$ and $R_6$-$R_8$ is hydrogen, and X and Z are O. In some embodiments, $R_6$ is —CF$_3$, each of $R_1$-$R_5$ and $R_7$-$R_8$ is hydrogen, and X and Z are O. In some embodiments, $R_6$ is —NH$_2$, each of $R_1$-$R_5$ and $R_7$-$R_8$ is hydrogen, and X and Z are O.

In some embodiments, the lyn kinase activator is of the formula:

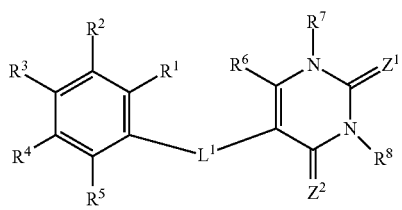

wherein:

$R^1$ is H, halo, $C_{1-6}$alkyl, $C_{2-6}$alkenyl, $C_{2-6}$alkynyl, $C_{1-6}$haloalkyl, $C_{1-6}$hydroxyalkyl, $C_{3-6}$cycloalkyl, aryl, heteroaryl, CN, NO$_2$, OR$^{a1}$, SR$^{a1}$, C(O)R$^{b1}$, C(O)NR$^{c1}$R$^{d1}$, C(O)OR$^{a1}$, OC(O)R$^{b1}$, OC(O)NR$^{c1}$R$^{d1}$, NR$^{c1}$R$^{d1}$, NR$^{c1}$C(O)R$^{b1}$, NR$^{c1}$C(O)NR$^{c1}$R$^{d1}$, NR$^{c1}$C(O)OR$^{a1}$, NR$^{c1}$S(O)$_2$NR$^{c1}$R$^{d1}$, S(O)R$^{b1}$, S(O)NR$^{c1}$R$^{d1}$, S(O)$_2$R$^{b1}$, NR$^{c1}$S(O)$_2$R$^{b1}$, or S(O)$_2$NR$^{c1}$R$^{d1}$, wherein each of $C_{1-6}$alkyl, $C_{2-6}$alkenyl, $C_{2-6}$alkynyl, $C_{1-6}$haloalkyl, $C_{1-6}$hydroxyalkyl, $C_{3-6}$cycloalkyl, aryl, and heteroaryl, is optionally substituted by 1, 2, 3, 4, or 5 substituents independently selected from halo, $C_{1-6}$alkyl, $C_{2-6}$alkenyl, $C_{2-6}$alkynyl, $C_{1-6}$haloalkyl, $C_{1-6}$hydroxyalkyl, $C_{3-6}$cycloalkyl, aryl, heteroaryl, CN, NO$_2$, OR$^{a2}$, SR$^{a2}$, C(O)R$^{b2}$, C(O)NR$^{c2}$R$^{d2}$, C(O)OR$^{a2}$, OC(O)R$^{b2}$, OC(O)NR$^{c2}$R$^{d2}$, NR$^{c2}$R$^{d2}$, NR$^{c2}$C(O)R$^{b2}$ NR$^{c2}$C(O)NR$^{c2}$R$^{d2}$, NR$^{c2}$S(O) NR$^{c2}$R$^{d2}$, S(O)R$^{b2}$, S(O)NR$^{c2}$R$^{d2}$, S(O)$_2$R$^{b2}$ NR$^{c2}$ S(O)$_2$R$^{b2}$, and S(O)$_2$NR$^{c2}$R$^{d2}$; $R^2$ is H, halo, $C_{1-6}$alkyl, $C_{2-6}$alkenyl, $C_{2-6}$alkynyl, $C_{1-6}$haloalkyl, $C_{1-6}$hydroxyalkyl, $C_{3-6}$cycloalkyl, aryl, heteroaryl, CN, NO$_2$, OR$^{a1}$, SR$^{a1}$, C(O)R$^{b1}$, C(O)NR$^{c1}$R$^{d1}$, C(O)OR$^{a1}$, OC(O)R$^{b1}$, OC(O)NR$^{c1}$R$^{d1}$, NR$^{c1}$R$^{d1}$, NR$^{c1}$C(O)R$^{b1}$, NR$^{c1}$C(O) NR$^{c1}$R$^{d1}$, NR$^{c1}$C(O)OR$^{a1}$, NR$^{c1}$S(O)$_2$NR$^{c1}$R$^{d1}$, S(O) R$^{b1}$, S(O)NR$^{c1}$R$^{a1}$, S(O)$_2$R$^{b1}$, NR$^{c1}$S(O)$_2$R$^{b1}$, or S(O)$_2$ NR$^{c1}$R$^{d1}$, wherein each of $C_{1-6}$alkyl, $C_{2-6}$alkenyl, $C_{2-6}$alkynyl, $C_{1-6}$haloalkyl, $C_{1-6}$hydroxyalkyl, $C_{3-6}$cycloalkyl, aryl, and heteroaryl, is optionally substituted by 1, 2, 3, 4, or 5 substituents independently selected from halo, $C_{1-6}$alkyl, $C_{2-6}$alkenyl, $C_{2-6}$alkynyl, $C_{1-6}$haloalkyl, $C_{1-6}$hydroxyalkyl, $C_{3-6}$cycloalkyl, aryl, heteroaryl, CN, NO$_2$, OR$^{a2}$, SR$^{a2}$, C(O)R$^{b2}$, C(O) NR$^{c2}$R$^{d2}$, C(O)OR$^{a2}$, OC(O)R$^{b2}$, OC(O)NR$^{c2}$R$^{d2}$, NR$^{c2}$R$^{d2}$, NR$^{c2}$C(O)R$^{b2}$ NR$^{c2}$C(O)NR$^{c2}$R$^{d2}$, NR$^{c2}$C (O)OR$^{a2}$, NR$^{c2}$S(O)NR$^{c2}$R$^{12}$, S(O)R$^{b2}$, S(O)NR$^{c2}$R$^{d2}$, S(O)$_2$R$^{b2}$ NR$^{c2}$S(O)$_2$R$^{b2}$, and S(O)$_2$NR$^{c2}$R$^{d2}$; $R^3$ is H, halo, $C_{1-6}$alkyl, $C_{2-6}$alkenyl, $C_{2-6}$alkynyl, $C_{1-6}$haloalkyl, $C_{1-6}$hydroxyalkyl, $C_{3-6}$cycloalkyl, aryl, heteroaryl, CN, NO$_2$, OR$^{a1}$, SR$^{a1}$, C(O)R$^{b}$, C(O)NR$^{c1}$R$^{d1}$, C(O) OR$^{a1}$ OC(O)R$^{b1}$, OC(O)NR$^{c1}$R$^{d1}$, NR$^{c1}$R$^{d1}$, NR$^{c1}$C(O) R$^{b1}$, NR$^{c1}$C(O)NR$^{c1}$R$^{d1}$, NR$^{c1}$C(O)OR$^{a1}$, NR$^{c1}$S(O)$_2$ NR$^{c1}$R$^{d1}$, S(O)R$^{b1}$, S(O)NR$^{c1}$R$^{a1}$, S(O)$_2$R$^{b1}$, NR$^{c1}$S (O)$_2$R$^{b1}$, or S(O)$_2$NR$^{c1}$R$^{d1}$, wherein each of $C_{1-6}$alkyl, $C_{2-6}$alkenyl, $C_{2-6}$alkynyl, $C_{1-6}$haloalkyl, $C_{1-6}$hydroxyalkyl, $C_{3-6}$cycloalkyl, aryl, and heteroaryl, is optionally substituted by 1, 2, 3, 4, or 5 substituents independently selected from halo, $C_{1-6}$alkyl, $C_{2-6}$alkenyl, $C_{2-6}$alkynyl, $C_{1-6}$haloalkyl, $C_{1-6}$hydroxyalkyl, $C_{3-6}$cycloalkyl, aryl, heteroaryl, CN, NO$_2$, OR$^{a2}$, SR$^{a2}$, C(O)R$^{b2}$, C(O) NR$^{c2}$R$^{d2}$, C(O)OR$^{a2}$, OC(O)R$^{b2}$, OC(O)NR$^{c2}$R$^{d2}$, NR$^{c2}$R$^{d2}$, NR$^{c2}$C(O)R$^{b2}$ NR$^{c2}$C(O)NR$^{c2}$R$^{d2}$, NR$^{c2}$C (O)OR$^{a2}$, NR$^{c2}$S(O)NR$^{c2}$R$^{d2}$, S(O)R$^{b2}$, S(O)NR$^{c2}$R$^{d2}$, S(O)$_2$R$^{b2}$ NR$^{c2}$S(O)$_2$R$^{b2}$, and S(O)$_2$NR$^{c2}$R$^{d2}$; $R^4$ is H, halo, $C_{1-6}$alkyl, $C_{2-6}$alkenyl, $C_{2-6}$alkynyl, $C_{1-6}$haloalkyl, $C_{1-6}$hydroxyalkyl, $C_{3-6}$cycloalkyl, aryl, heteroaryl, CN, NO$_2$, OR$^{a1}$, SR$^{a1}$, C(O)R$^{b}$, C(O)NR$^{c1}$R$^{d1}$, C(O) OR$^{a1}$ OC(O)R$^{b1}$, OC(O)NR$^{c1}$R$^{d1}$, NR$^{c1}$R$^{d1}$, NR$^{c1}$C(O) R$^{b1}$, NR$^{c1}$C(O)NR$^{c1}$R$^{d1}$, NR$^{c1}$C(O)OR$^{a1}$, NR$^{c1}$S(O)$_2$ NR$^{c1}$R$^{d1}$, S(O)R$^{b1}$, S(O)NR$^{c1}$R$^{d1}$, S(O)$_2$R$^{b1}$, NR$^{c1}$S (O)$_2$R$^{b1}$, or S(O)$_2$NR$^{c1}$R$^{a1}$, wherein each of $C_{1-6}$alkyl, $C_{2-6}$alkenyl, $C_{2-6}$alkynyl, $C_{1-6}$haloalkyl, $C_{1-6}$hydroxyalkyl, $C_{3-6}$cycloalkyl, aryl, and heteroaryl, is optionally substituted by 1, 2, 3, 4, or 5 substituents independently selected from halo, $C_{1-6}$alkyl, $C_{2-6}$alkenyl, $C_{2-6}$alkynyl, $C_{1-6}$haloalkyl, $C_{1-6}$hydroxyalkyl, $C_{3-6}$cycloalkyl, aryl, heteroaryl, CN, NO$_2$, OR$^{a2}$, SR$^{a2}$, C(O)R$^{b2}$, C(O) NR$^{c2}$R$^{d2}$, C(O)OR$^{a2}$, OC(O)R$^{b2}$, OC(O)NR$^{c2}$R$^{d2}$, NR$^{c2}$R$^{d2}$, NR$^{c2}$C(O)R$^{b2}$ NR$^{c2}$C(O)NR$^{c2}$R$^{d2}$, NR$^{c2}$C (O)OR$^{a2}$, NR$^{c2}$S(O)NR$^{c2}$R$^{d2}$, S(O)R$^{b2}$, S(O)NR$^{c2}$R$^{d2}$, S(O)$_2$R$^{b2}$ NR$^{c2}$S(O)$_2$R$^{b2}$, and S(O)$_2$NR$^{c2}$R$^{d2}$; $R^5$ is H, halo, $C_{1-6}$alkyl, $C_{2-6}$alkenyl, $C_{2-6}$alkynyl, $C_{1-6}$haloalkyl, $C_{1-6}$hydroxyalkyl, $C_{3-6}$cycloalkyl, aryl, heteroaryl, CN, NO$_2$, OR$^{a1}$, SR$^{a1}$, C(O)R$^{b1}$, C(O)NR$^{c1}$R$^{d1}$, C(O) OR$^{a1}$, OC(O)R$^{b1}$, OC(O)NR$^{c1}$R$^{d1}$, NR$^{c1}$R$^{d1}$, NR$^{c1}$C (O)R$^{b1}$, NR$^{c1}$C(O)NR$^{c1}$R$^{d1}$, NR$^{c1}$C(O)OR$^{a1}$, NR$^{c1}$S (O)$_2$NR$^{c1}$R$^{d1}$, S(O)R$^{b1}$, S(O)NR$^{c1}$R$^{d1}$, S(O)$_2$R$^{b1}$, NR$^{c1}$S(O)$_2$R$^{b1}$, or S(O)$_2$NR$^{c1}$R$^{d1}$, wherein each of $C_{1-6}$alkyl, $C_{2-6}$alkenyl, $C_{2-6}$alkynyl, $C_{1-6}$haloalkyl, $C_{1-6}$hydroxyalkyl, $C_{3-6}$cycloalkyl, aryl, and heteroaryl, is optionally substituted by 1, 2, 3, 4, or 5 substituents independently selected from halo, $C_{1-6}$alkyl, $C_{2-6}$alkenyl, $C_{2-6}$alkynyl, $C_{1-6}$haloalkyl, $C_{1-6}$hydroxyalkyl, $C_{3-6}$cycloalkyl, aryl, heteroaryl, CN, NO$_2$, OR$^{a2}$, SR$^{a2}$, C(O)R$^{b2}$, C(O)NR$^{c2}$R$^{d2}$, C(O)OR$^{a2}$, OC(O)R$^{b2}$, OC(O)NR$^{c2}$R$^{d2}$, NR$^{c2}$R$^{d2}$, NR$^{c2}$C(O)R$^{b2}$ NR$^{c2}$C(O)

$NR^{c2}R^{d2}$, $NR^{c2}C(O)OR^{a2}$, $NR^{c2}S(O)NR^{c2}R^{d2}$, $S(O)R^{b2}$, $S(O)NR^{c2}R^{d2}$, $S(O)_2R^{b2}$ $NR^{c2}S(O)_2R^{b2}$, and $S(O)_2 NR^{c2}R^{d2}$;

or two adjacent groups of $R^1$, $R^2$, $R^3$, $R^4$, and $R^5$ can link to form a fused cycloalkyl or fused heterocycloalkyl group, each optionally substituted by 1, 2, or 3 substituents independently selected from halo, $C_{1-6}$alkyl, $C_{2-6}$alkenyl, $C_{2-6}$alkynyl, $C_{1-6}$haloalkyl, $C_{1-6}$hydroxyalkyl, $C_{3-6}$cycloalkyl, aryl, heteroaryl, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$ $NR^{c2}C(O)NR^{c2}R^{d2}$, $NR^{c2}C(O)OR^{a2}$, $NR^{c2}S(O)NR^{c2}R^{d2}$, $S(O)R^{b2}$, $S(O)NR^{c2}R^{d2}$, $S(O)_2R^{b2}$ $NR^{c2}S(O)_2R^{b2}$, and $S(O)_2 NR^{c2}R^{d2}$;

$R^6$ is H, halo, $C_{1-6}$alkyl, $C_{2-6}$alkenyl, $C_{2-6}$alkynyl, $C_{1-6}$haloalkyl, $C_{1-6}$hydroxyalkyl, $C_{3-6}$cycloalkyl, aryl, heteroaryl, CN, $NO_2$, $OR^{a1}$, $SR^{a1}$, $C(O)R^b$, $C(O)NR^{c1}R^{d1}$, $C(O)OR^{a1}$ $OC(O)R^{b1}$, $OC(O)NR^{c1}R^{d1}$, $NR^{c1}R^{d1}$, $NR^{c1}C(O)R^{b1}$, $NR^{c1}C(O)NR^{c1}R^{d1}$, $NR^{c1}C(O)OR^{a1}$, $NR^{c1}S(O)_2NR^{c1}R^{d1}$, $S(O)R^{b1}$, $S(O)NR^{c1}R^{d1}$, $S(O)_2R^{b1}$, $NR^{c1}S(O)_2R^{b1}$, or $S(O)_2NR^{c1}R^{d1}$, wherein each of $C_{1-6}$alkyl, $C_{2-6}$alkenyl, $C_{2-6}$alkynyl, $C_{1-6}$haloalkyl, $C_{1-6}$hydroxyalkyl, $C_{3-6}$cycloalkyl, aryl, and heteroaryl, is optionally substituted by 1, 2, 3, 4, or 5 substituents independently selected from halo, $C_{1-6}$alkyl, $C_{2-6}$alkenyl, $C_{2-6}$alkynyl, $C_{1-6}$haloalkyl, $C_{1-6}$hydroxyalkyl, $C_{3-6}$cycloalkyl, CN, $NO_2$, $OR^{a2}$, $SR^{a2}$, $C(O)R^{b2}$, $C(O)NR^{c2}R^{d2}$, $C(O)OR^{a2}$ $OC(O)R^{b2}$, $OC(O)NR^{c2}R^{d2}$, $NR^{c2}R^2$, $NR^{c2}C(O)R^{b2}$, $NR^{c2}C(O)NR^{c2}R^{d2}$, $NR^{c2}C(O)OR^{a2}$ $NR^{c2}S(O)NR^{c2}R^{d2}$, $S(O)R^{b2}$, $S(O)NR^{c2}R^{d2}$, $S(O)_2R^{b2}$, $NR^{c2}S(O)_2R^{b2}$, and $S(O)_2NR^{c2}R^{d2}$ $R^7$ is H, $C_{1-6}$alkyl, $C_{1-6}$haloalkyl, $C_{1-6}$hydroxyalkyl, $C(O)R^{b1}$, $C(O)NR^{c1}R^{d1}$, $C(O)OR^{a1}$, $S(O)R^{b1}$, $S(O)NR^{c1}R^{d1}$, $S(O)_2R^{b1}$, or $S(O)_2NR^{c1}R^{d1}$;

$R^8$ is H, $C_{1-6}$alkyl, $C_{1-6}$haloalkyl, $C_{1-6}$hydroxyalkyl, $C(O)R^{b1}$, $C(O)NR^{c1}R^{d1}$, $C(O)OR^{a1}$, $S(O)R^{b1}$, $S(O)NR^{c1}R^{d1}$, $S(O)_2R^{b1}$, or $S(O)_2NR^{c1}R^{d1}$;

$R^{a1}$, $R^{b1}$, $R^{c1}$, and $R^{d1}$ are each, independently, selected from H, $C_{1-6}$alkyl, $C_{1-6}$haloalkyl, $C_{1-6}$hydroxyalkyl, $C_{2-6}$alkenyl, $C_{2-6}$alkynyl, aryl, cycloalkyl, heteroaryl, heterocycloalkyl, arylalkyl, heteroarylalkyl, cycloalkylalkyl, and heterocycloalkylalkyl, wherein each of $C_{1-6}$alkyl, $C_{1-6}$haloalkyl, $C_{1-6}$hydroxyalkyl, $C_{2-6}$alkenyl, $C_{2-6}$alkynyl, aryl, cycloalkyl, heteroaryl, heterocycloalkyl, arylalkyl, heteroarylalkyl, cycloalkylalkyl, and heterocycloalkylalkyl is optionally substituted with 1, 2, 3, 4, or 5 substituents independently selected from OH, $NO_2$, CN, amino, halo, $C_{1-6}$alkyl, $C_{1-6}$alkoxy, $C_{1-6}$haloalkyl, $C_{1-6}$hydroxyalkyl, and $C_{1-6}$haloalkoxy;

or $R^{c1}$ and $R^{d1}$ together with the N atom to which they are attached form a 4-, 5-, 6-, or 7-membered heterocycloalkyl group or heteroaryl group, each optionally substituted with 1, 2, or 3 substituents independently selected from OH, $NO_2$, CN, amino, halo, $C_{1-6}$alkyl, $C_{1-6}$alkoxy, $C_{1-6}$haloalkyl, $C_{1-6}$hydroxyalkyl, and $C_{1-6}$haloalkoxy;

$R^{a2}$, $R^{b2}$, $R^{c2}$, and $R^{d2}$ are each, independently, selected from H, $C_{1-6}$alkyl, $C_{1-6}$haloalkyl, $C_{1-6}$hydroxyalkyl, $C_{2-6}$alkenyl, $C_{2-6}$alkynyl, aryl, cycloalkyl, heteroaryl, heterocycloalkyl, arylalkyl, heteroarylalkyl, cycloalkylalkyl, and heterocycloalkylalkyl, wherein each of $C_{1-6}$alkyl, $C_{1-6}$haloalkyl, $C_{1-6}$hydroxyalkyl, $C_{2-6}$alkenyl, $C_{2-6}$alkynyl, aryl, cycloalkyl, heteroaryl, heterocycloalkyl, arylalkyl, heteroarylalkyl, cycloalkylalkyl, or heterocycloalkylalkyl is optionally substituted with 1, 2, or 3 substituents independently selected from OH, $NO_2$, CN, amino, halo, $C_{1-6}$alkyl, $C_{1-6}$alkoxy, $C_{1-6}$haloalkyl, $C_{1-6}$hydroxyalkyl, and $C_{1-6}$haloalkoxy;

or $R^{c2}$ and $R^{d2}$ together with the N atom to which they are attached form a 4-, 5-, 6-, or 7-membered heterocycloalkyl group or heteroaryl group, each optionally substituted with 1, 2, or 3 substituents independently selected from OH, $NO_2$, CN, amino, halo, $C_{1-6}$alkyl, $C_{1-6}$alkoxy, $C_{1-6}$haloalkyl, $C_{1-6}$hydroxyalkyl, and $C_{1-6}$haloalkoxy;

$Z^1$ is O, S, or $NR^9$;

$R^9$ is H, OH, $C_{1-6}$alkoxy, $C_{1-6}$haloalkyl, $C_{1-6}$hydroxyalkyl, aryloxy, heteroaryloxy, CN, or $NO_2$;

$Z^2$ is O, S, or $NR^{10}$;

$R^{10}$ is H, OH, $C_{1-6}$alkoxy, $C_{1-6}$haloalkyl, $C_{1-6}$hydroxyalkyl, aryloxy, heteroaryloxy, CN, or $NO_2$;

$L^1$ is O, S, or $NR^{11}$; and $R^{11}$ is H, $C_{1-6}$alkyl, $C_{1-6}$haloalkyl, $C_{1-6}$hydroxyalkyl, $C(O)R^{b1}$, $C(O)NR^{c1}R^{d1}$, $C(O)OR^{a1}$, $S(O)R^{b1}$, $S(O)NR^{c1}R^{d1}$, $S(O)_2R^{b1}$, or $S(O)_2NR^{c1}R^{d1}$;

or a pharmaceutically acceptable salt thereof.

In some embodiments, the lyn kinase activator is of the formula:

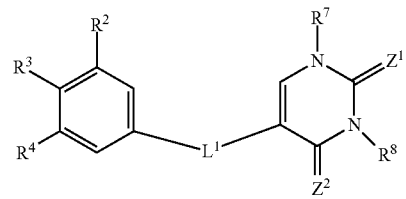

wherein:

$R^2$, $R^3$, and $R^4$ are each, independently, H, halo, $C_{1-6}$alkyl, $C_{1-6}$hydroxyalkyl, or $C_{1-6}$haloalkyl;

$R^7$ is H, $C_{1-6}$alkyl, $C(O)R^{b1}$, $C(O)R^{c1}R^{d1}$ or $C(O)OR^{a1}$;

$R^8$ is H, $C_{1-6}$alkyl, $C(O)R^{b1}$, $C(O)NR^{c1}R^{d1}$, or $C(O)OR^{a1}$;

$R^{a1}$, $R^{b1}$, $R^{e1}$, and $R^{d1}$ are each, independently, selected from H, $C_{1-6}$alkyl, $C_{1-6}$haloalkyl, $C_{1-6}$hydroxyalkyl, $C_{2-6}$alkenyl, $C_{2-6}$alkynyl, aryl, cycloalkyl, heteroaryl, heterocycloalkyl, arylalkyl, heteroarylalkyl, cycloalkylalkyl, and heterocycloalkylalkyl, wherein each of $C_{1-6}$alkyl, $C_{1-6}$haloalkyl, $C_{1-6}$hydroxyalkyl, $C_{2-6}$alkenyl, $C_{2-6}$alkynyl, aryl, cycloalkyl, heteroaryl, heterocycloalkyl, arylalkyl, heteroarylalkyl, cycloalkylalkyl, and heterocycloalkylalkyl is optionally substituted with 1, 2, 3, 4, or 5 substituents independently selected from OH, $NO_2$, CN, amino, halo, $C_{1-6}$alkyl, $C_{1-6}$alkoxy, $C_{1-6}$haloalkyl, $C_{1-6}$hydroxyalkyl, and $C_{1-6}$haloalkoxy;

or $R^e$ and $R^{d1}$ together with the N atom to which they are attached form a 4-, 5-, 6-, or 7-membered heterocycloalkyl group or heteroaryl group, each optionally substituted with 1, 2, or 3 substituents independently selected from OH, $NO_2$, CN, amino, halo, $C_{1-6}$alkyl, $C_{1-6}$alkoxy, $C_{1-6}$haloalkyl, $C_{1-6}$hydroxyalkyl, and $C_{1-6}$haloalkoxy;

$Z^1$ is O or S;

$Z^2$ is O or S; and $L^1$ is O or S;

or a pharmaceutically acceptable salt thereof.

In some embodiments, the lyn kinase activator is of the formula:

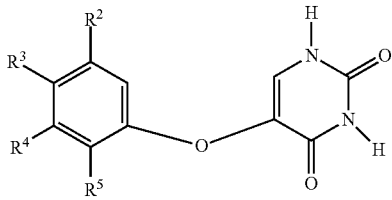

wherein: $R^2$, $R^3$, $R^4$, and $R^5$ are each, independently, H, F, Cl, $CH_3$, $SCH_3$, $OCH_3$, $C(CH_3)_3$, $CH(CH_3)_2$, or $C_2H_5$; or a pharmaceutically acceptable salt thereof.

In some embodiments, the lyn kinase activator is of the formula:

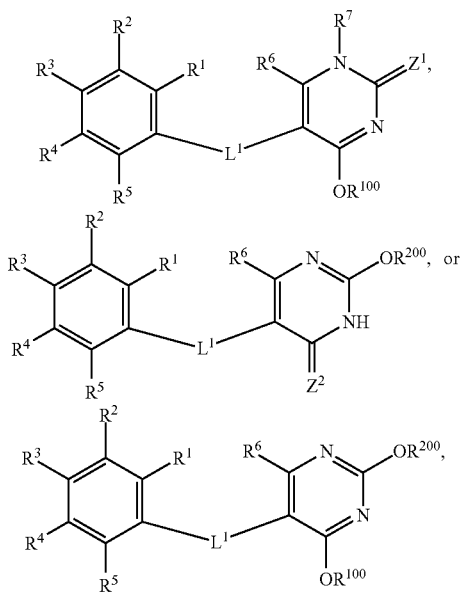

wherein:
$R^1$ is H, halo, $C_{1-6}$alkyl, $C_{2-6}$alkenyl, $C_{2-6}$alkynyl, $C_{1-6}$haloalkyl, $C_{1-6}$hydroxyalkyl, $C_{3-6}$cycloalkyl, aryl, heteroaryl, CN, $NO_2$, $OR^a$, $SR^{a1}$, $C(O)R^{b1}$, $C(O)NR^{c1}R^{d1}$, $C(O)OR^{a1}$ $OC(O)R^{b1}$, $OC(O)NR^{c1}R^{d1}$, $NR^{c1}R^{d1}$, $NR^{c1}C(O)R^{b1}$, $NR^{c1}C(O)NR^{c1}R^{d1}$, $NR^{c1}C(O)OR^{a1}$, $NR^{c1}S(O)_2NR^{c1}R^{d1}$, $S(O)R^{b1}$, $S(O)NR^{c1}R^{d1}$, $S(O)_2R^{b1}$, $NR^{c1}S(O)_2R^{b1}$, or $S(O)_2NR^{c1}R^{d1}$, wherein each of $C_{1-6}$alkyl, $C_{2-6}$alkenyl, $C_{2-6}$alkynyl, $C_{1-6}$haloalkyl, $C_{1-6}$hydroxyalkyl, $C_{3-6}$cycloalkyl, aryl, and heteroaryl, is optionally substituted by 1, 2, 3, 4, or 5 substituents independently selected from halo, $C_{1-6}$alkyl, $C_{2-6}$alkenyl, $C_{2-6}$alkynyl, $C_{1-6}$haloalkyl, $C_{1-6}$hydroxyalkyl, $C_{3-6}$cycloalkyl, aryl, heteroaryl, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$ $NR^{c2}C(O)NR^{c2}R^{d2}$, $NR^{c2}C(O)OR^{a2}$, $NR^{c2}S(O)NR^{c2}R^{d2}$, $S(O)R^{b2}$, $S(O)NR^{c2}R^{d2}$, $S(O)_2R^{b2}$ $NR^{c2}S(O)_2R^{b2}$, and $S(O)_2NR^{c2}R^{d2}$; $R^2$ is H, halo, $C_{1-6}$alkyl, $C_{2-6}$alkenyl, $C_{2-6}$alkynyl, $C_{1-6}$haloalkyl, $C_{1-6}$hydroxyalkyl, $C_{3-6}$cycloalkyl, aryl, heteroaryl, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)NR^{c1}R^{d1}$, $NR^{c1}C(O)OR^{a1}$, $NR^{c1}S(O)_2NR^{c1}R^{d1}$, $S(O)R^{b1}$, $S(O)NR^{c1}R^{d1}$, $S(O)_2R^{b1}$, $NR^{c1}S(O)_2R^{b1}$, or $S(O)_2NR^{c1}R^{d1}$, wherein each of $C_{1-6}$alkyl, $C_{2-6}$alkenyl, $C_{2-6}$alkynyl, $C_{1-6}$haloalkyl, $C_{1-6}$hydroxyalkyl, $C_{3-6}$cycloalkyl, aryl, and heteroaryl, is optionally substituted by 1, 2, 3, 4, or 5 substituents independently selected from halo, $C_{1-6}$alkyl, $C_{2-6}$alkenyl, $C_{2-6}$alkynyl, $C_{1-6}$haloalkyl, $C_{1-6}$hydroxyalkyl, $C_{3-6}$cycloalkyl, aryl, heteroaryl, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$ $NR^{c2}C(O)NR^{c2}R^{d2}$, $NR^{c2}C(O)OR^{a2}$, $NR^{c2}S(O)NR^{c2}R^{d2}$, $S(O)R^{b2}$, $S(O)NR^{c2}R^{d2}$, $S(O)_2R^{b2}$ $NR^{c2}S(O)_2R^{b2}$, and $S(O)_2NR^{c2}R^{d2}$;

$R^3$ is H, halo, $C_{1-6}$alkyl, $C_{2-6}$alkenyl, $C_{2-6}$alkynyl, $C_{1-6}$haloalkyl, $C_{1-6}$hydroxyalkyl, $C_{3-6}$cycloalkyl, aryl, heteroaryl, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)NR^{c1}R^{d1}$, $NR^{c1}C(O)OR^{a1}$, $NR^{c1}S(O)_2NR^{c1}R^{d1}$, $S(O)R^{b1}$, $S(O)NR^{c1}R^{d1}$, $S(O)_2R^{b1}$, $NR^{c1}S(O)_2R^{b1}$, or $S(O)_2NR^{c1}R^{d1}$, wherein each of $C_{1-6}$alkyl, $C_{2-6}$alkenyl, $C_{2-6}$alkynyl, $C_{1-6}$haloalkyl, $C_{1-6}$hydroxyalkyl, $C_{3-6}$cycloalkyl, aryl, and heteroaryl, is optionally substituted by 1, 2, 3, 4, or 5 substituents independently selected from halo, $C_{1-6}$alkyl, $C_{2-6}$alkenyl, $C_{2-6}$alkynyl, $C_{1-6}$haloalkyl, $C_{1-6}$hydroxyalkyl, $C_{3-6}$cycloalkyl, aryl, heteroaryl, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$ $NR^{c2}C(O)NR^{c2}R^{d2}$, $NR^{c2}C(O)OR^{a2}$, $NR^{c2}S(O)NR^{c2}R^{d2}$, $S(O)R^{b2}$, $S(O)NR^{c2}R^{d2}$, $S(O)_2R^{b2}$ $NR^{c2}S(O)_2R^{b2}$, and $S(O)_2NR^{c2}R^{d2}$;

$R^4$ is H, halo, $C_{1-6}$alkyl, $C_{2-6}$alkenyl, $C_{2-6}$alkynyl, $C_{1-6}$haloalkyl, $C_{1-6}$hydroxyalkyl, $C_{3-6}$cycloalkyl, aryl, heteroaryl, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)NR^{c1}R^{d1}$, $NR^{c1}C(O)OR^{a1}$, $NR^{c1}S(O)_2NR^{c1}R^{d1}$, $S(O)R^{b1}$, $S(O)NR^{c1}R^{d1}$, $S(O)_2R^{b1}$, $NR^{c1}S(O)_2R^{b1}$, or $S(O)_2NR^{c1}R^{d1}$, wherein each of $C_{1-6}$alkyl, $C_{2-6}$alkenyl, $C_{2-6}$alkynyl, $C_{1-6}$haloalkyl, $C_{1-6}$hydroxyalkyl, $C_{3-6}$cycloalkyl, aryl, and heteroaryl, is optionally substituted by 1, 2, 3, 4, or 5 substituents independently selected from halo, $C_{1-6}$alkyl, $C_{2-6}$alkenyl, $C_{2-6}$alkynyl, $C_{1-6}$haloalkyl, $C_{1-6}$hydroxyalkyl, $C_{3-6}$cycloalkyl, aryl, heteroaryl, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$ $NR^{c2}C(O)NR^{c2}R^{d2}$, $NR^{c2}C(O)OR^{a2}$, $NR^{c2}S(O)NR^{c2}R^{d2}$, $S(O)R^{b2}$, $S(O)NR^{c2}R^{d2}$, $S(O)_2R^{b2}$ $NR^{c2}S(O)_2R^{b2}$, and $S(O)_2NR^{c2}R^{d2}$;

$R^5$ is H, halo, $C_{1-6}$alkyl, $C_{2-6}$alkenyl, $C_{2-6}$alkynyl, $C_{1-6}$haloalkyl, $C_{1-6}$hydroxyalkyl, $C_{3-6}$cycloalkyl, aryl, heteroaryl, CN, $NO_2$, $OR^a$, $SR^{a1}$, $C(O)R^{b1}$, $C(O)NR^{c1}R^{d1}$, $C(O)OR^{a1}$ $OC(O)R^{b1}$, $OC(O)NR^{c1}R^{d1}$, $NR^{c1}R^{d1}$, $NR^{c1}C(O)R^{b1}$, $NR^{c1}C(O)NR^{c1}R^{d1}$, $NR^{c1}C(O)OR^{a1}$, $NR^{c1}S(O)_2NR^{c1}R^{d1}$, $S(O)R^{b1}$, $S(O)NR^{c1}R^{d1}$, $S(O)_2R^{b1}$, $NR^{c1}S(O)_2R^{b1}$, or $S(O)_2NR^{c1}R^{d1}$, wherein each of $C_{1-6}$alkyl, $C_{2-6}$alkenyl, $C_{2-6}$alkynyl, $C_{1-6}$haloalkyl, $C_{1-6}$hydroxyalkyl, $C_{3-6}$cycloalkyl, aryl, and heteroaryl, is optionally substituted by 1, 2, 3, 4, or 5 substituents independently selected from halo, $C_{1-6}$alkyl, $C_{2-6}$alkenyl, $C_{2-6}$alkynyl, $C_{1-6}$haloalkyl, $C_{1-6}$hydroxyalkyl, $C_{3-6}$cycloalkyl, aryl, heteroaryl, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$ $NR^{c2}C(O)NR^{c2}R^{d2}$, $NR^{c2}C(O)OR^{a2}$, $NR^{c2}S(O)NR^{c2}R^{d2}$, $S(O)R^{b2}$, $S(O)NR^{c2}R^{d2}$, $S(O)_2R^{b2}$ $NR^{c2}S(O)_2R^{b2}$, and $S(O)_2NR^{c2}R^{d2}$;

or two adjacent groups of $R^1$, $R^2$, $R^3$, $R^4$, and $R^5$ can link to form a fused cycloalkyl or fused heterocycloalkyl group, each optionally substituted by 1, 2, or 3 substituents independently selected from halo, $C_{1-6}$alkyl, $C_{2-6}$alkenyl, $C_{2-6}$alkynyl, $C_{1-6}$haloalkyl, $C_{1-6}$hydroxyalkyl, $C_{3-6}$cycloalkyl, aryl, heteroaryl, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$ $NR^{c2}C(O)$ $NR^{c2}R^{d2}$, $NR^{c2}C(O)OR^{a2}$, $NR^{c2}S(O)NR^{c2}R^{d2}$, $S(O)R^{b2}$, $S(O)NR^{c2}R^{d2}$, $S(O)_2R^{b2}$ $NR^{c2}S(O)_2R^{b2}$, and $S(O)_2 NR^{c2}R^{d2}$;

$R^6$ is H, halo, $C_{1-6}$alkyl, $C_{2-6}$alkenyl, $C_{2-6}$alkynyl, $C_{1-6}$haloalkyl, $C_{1-6}$hydroxyalkyl, $C_{3-6}$cycloalkyl, aryl, heteroaryl, CN, $NO_2$, $OR^{a1}$, $SR^{a1}$, $C(O)R^b$, $C(O)NR^{c1}R^{d1}$, $C(O)OR^{a1}$ $OC(O)R^{b1}$, $OC(O)NR^{c1}R^{d1}$, $NR^{c1}R^{d1}$, $NR^{c1}C(O)R^{b1}$, $NR^{c1}C(O)NR^{c1}R^{d1}$, $NR^{c1}C(O)OR^{a1}$, $NR^{c1}S(O)_2NR^{c1}R^{d1}$, $S(O)R^{b1}$, $S(O)NR^{c1}R^{d1}$, $S(O)_2R^{b1}$, $NR^{c1}S(O)_2R^{b1}$, or $S(O)_2NR^{c1}R^{d1}$, wherein each of $C_{1-6}$alkyl, $C_{2-6}$alkenyl, $C_{2-6}$alkynyl, $C_{1-6}$haloalkyl, $C_{1-6}$hydroxyalkyl, $C_{3-6}$cycloalkyl, aryl, and heteroaryl, is optionally substituted by 1, 2, 3, 4, or 5 substituents independently selected from halo, $C_{1-6}$alkyl, $C_{2-6}$alkenyl, $C_{2-6}$alkynyl, $C_{1-6}$haloalkyl, $C_{1-6}$hydroxyalkyl, $C_{3-6}$cycloalkyl, CN, $NO_2$, $OR^{a2}$, $SR^{a2}$, $C(O)R^{b2}$, $C(O)NR^{c2}R^{d2}$, $C(O)OR^{a2}$ $OC(O)R^{b2}$, $OC(O)NR^{c2}R^{d2}$, $NR^{c2}R^2$, $NR^{c2}C(O)R^{b2}$, $NR^{c2}C(O)NR^{c2}R^{d2}$, $NR^{c2}C(O)OR^{a2}$ $NR^{c2}S(O)NR^{c2}R^{d2}$, $S(O)R^{b2}$, $S(O)NR^{c2}R^{d2}$, $S(O)_2R^{b2}$, $NR^{c2}S(O)_2R^{b2}$, and $S(O)_2NR^{c2}R^{d2}$;

$R^7$ is H, $C_{1-6}$alkyl, $C_{1-6}$haloalkyl, $C(O)R^{b1}$, $C(O)NR^{c1}R^{d1}$, $C(O)OR^{a1}$, $S(O)R^{b1}$, $S(O)NR^{c1}R^{d1}$, $S(O)_2R^{b1}$, or $S(O)_2NR^{c1}R^{d1}$;

$R^{a1}$, $R^{b1}$, $R^{c1}$, and $R^{d1}$ are each, independently, selected from H, $C_{1-6}$alkyl, $C_{1-6}$haloalkyl, $C_{1-6}$hydroxyalkyl, $C_{2-6}$alkenyl, $C_{2-6}$alkynyl, aryl, cycloalkyl, heteroaryl, heterocycloalkyl, arylalkyl, heteroarylalkyl, cycloalkylalkyl, and heterocycloalkylalkyl, wherein each of $C_{1-6}$alkyl, $C_{1-6}$haloalkyl, $C_{1-6}$hydroxyalkyl, $C_{2-6}$alkenyl, $C_{2-6}$alkynyl, aryl, cycloalkyl, heteroaryl, heterocycloalkyl, arylalkyl, heteroarylalkyl, cycloalkylalkyl, and heterocycloalkylalkyl is optionally substituted with 1, 2, 3, 4, or 5 substituents independently selected from OH, $NO_2$, CN, amino, halo, $C_{1-6}$alkyl, $C_{1-6}$alkoxy, $C_{1-6}$haloalkyl, $C_{1-6}$hydroxyalkyl, and $C_{1-6}$haloalkoxy;

or $R^{c1}$ and $R^{d1}$ together with the N atom to which they are attached form a 4-, 5-, 6-, or 7-membered heterocycloalkyl group or heteroaryl group, each optionally substituted with 1, 2, or 3 substituents independently selected from OH, $NO_2$, CN, amino, halo, $C_{1-6}$alkyl, $C_{1-6}$alkoxy, $C_{1-6}$haloalkyl, $C_{1-6}$hydroxyalkyl, and $C_{1-6}$haloalkoxy;

$R^{a2}$, $R^{b2}$, $R^{c2}$, and $R^{d2}$ are each, independently, selected from H, $C_{1-6}$alkyl, $C_{1-6}$haloalkyl, $C_{1-6}$hydroxyalkyl, $C_{2-6}$alkenyl, $C_{2-6}$alkynyl, aryl, cycloalkyl, heteroaryl, heterocycloalkyl, arylalkyl, heteroarylalkyl, cycloalkylalkyl, and heterocycloalkylalkyl, wherein each of $C_{1-6}$alkyl, $C_{1-6}$haloalkyl, $C_{1-6}$hydroxyalkyl, $C_{2-6}$alkenyl, $C_{2-6}$alkynyl, aryl, cycloalkyl, heteroaryl, heterocycloalkyl, arylalkyl, heteroarylalkyl, cycloalkylalkyl, or heterocycloalkylalkyl is optionally substituted with 1, 2, or 3 substituents independently selected from OH, $NO_2$, CN, amino, halo, $C_{1-6}$alkyl, $C_{1-6}$alkoxy, $C_{1-6}$haloalkyl, $C_{1-6}$hydroxyalkyl, and $C_{1-6}$haloalkoxy;

or $R^{c2}$ and $R^{d2}$ together with the N atom to which they are attached form a 4-, 5-, 6-, or 7-membered heterocycloalkyl group or heteroaryl group, each optionally substituted with 1, 2, or 3 substituents independently selected from OH, $NO_2$, CN, amino, halo, $C_{1-6}$alkyl, $C_{1-6}$alkoxy, $C_{1-6}$haloalkyl, $C_{1-6}$hydroxyalkyl, and $C_{1-6}$haloalkoxy;

$Z^1$ is O, S, or $NR^9$;

$R^9$ is H, OH, $C_{1-6}$alkoxy, $C_{1-6}$haloalkyl, $C_{1-6}$hydroxyalkyl, aryloxy, heteroaryloxy, CN, or $NO_2$;

$Z^2$ is O, S, or $NR^{10}$;

$R^{10}$ is H, OH, $C_{1-6}$alkoxy, $C_{1-6}$haloalkyl, $C_{1-6}$hydroxyalkyl, aryloxy, heteroaryloxy, CN, or $NO_2$;

$L^1$ is O, S, or $NR^{11}$;

$R^{11}$ is H, $C_{1-6}$alkyl, $C_{1-6}$haloalkyl, $C_{1-6}$hydroxyalkyl, $C(O)R^{b1}$, $C(O)NR^{c1}R^{d1}$, $C(O)OR^{a1}$, $S(O)R^{b1}$, $S(O)NR^{c1}R^{d1}$, $S(O)_2R^{b1}$, or $S(O)_2NR^{c1}R^{d1}$;

$R^{100}$ is a hydroxyl protecting group, $C_{1-6}$alkyl, $C_{2-6}$alkenyl, $C_{2-6}$alkynyl, $C_{1-6}$ haloalkyl, $C_{1-6}$hydroxyalkyl, $C_{3-6}$cycloalkyl, heterocycloalkyl, aryl, heteroaryl, $C(O)R^{b1}$, $C(O)NR^{c1}R^{d1}$, $C(O)OR^{a1}$, $S(O)R^{b1}$, $S(O)NR^{c1}R^{d1}$, $S(O)_2R^{b1}$, $S(O)_2NR^{c1}R^{d1}$, $S(O)_2OR^{e1}$, $P(O)OR^{f1}OR^{g1}$, or $Si(R^{h1})_3$, wherein each of $C_{1-6}$alkyl, $C_{2-6}$alkenyl, $C_{2-6}$alkynyl, $C_{1-6}$haloalkyl, $C_{1-6}$hydroxyalkyl, $C_{3-6}$cycloalkyl, aryl, and heteroaryl, is optionally substituted by 1, 2, 3, 4 or substituents independently selected from halo, $C_{1-6}$alkyl, $C_{2-6}$alkenyl, $C_{2-6}$alkynyl, $C_{1-6}$haloalkyl, $C_{1-6}$hydroxyalkyl, $C_{3-6}$cycloalkyl, aryl, heteroaryl, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$ $NR^{c2}C(O)NR^{c2}R^{d2}$, $NR^{c2}C(O)OR^{a2}$, $NR^{c2}S(O)NR^{c2}R^{d2}$, $S(O)R^{b2}$, $S(O)NR^{c2}R^{d2}$, $S(O)_2R^{b2}$ $NR^{c2}S(O)_2R^{b2}$, and $S(O)_2NR^{c2}R^{d2}$;

$R^{200}$ is a hydroxyl protecting group, $C_{1-6}$alkyl, $C_{2-6}$alkenyl, $C_{2-6}$alkynyl, $C_{1-6}$haloalkyl, $C_{1-6}$hydroxyalkyl, $C_{3-6}$cycloalkyl, heterocycloalkyl, aryl, heteroaryl, $C(O)R^{b1}$, $C(O)NR^{c1}R^{d1}$, $C(O)OR^{a1}$, $S(O)R^{b1}$, $S(O)NR^{c1}R^{d1}$, $S(O)_2R^{b1}$, $S(O)_2NR^{c1}R^{d1}$, $S(O)_2OR^{e1}$, $P(O)OR^{f1}OR^{g1}$, or $Si(R^{h1})_3$, wherein each of $C_{1-6}$alkyl, $C_{2-6}$alkenyl, $C_{2-6}$alkynyl, $C_{1-6}$haloalkyl, $C_{1-6}$hydroxyalkyl, $C_{3-6}$cycloalkyl, aryl, and heteroaryl, is optionally substituted by 1, 2, 3, 4 or substituents independently selected from halo, $C_{1-6}$alkyl, $C_{2-6}$alkenyl, $C_{2-6}$alkynyl, $C_{1-6}$haloalkyl, $C_{1-6}$hydroxyalkyl, $C_{3-6}$cycloalkyl, aryl, heteroaryl, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$, $NR^{c2}C(O)NR^{c2}R^{d2}$, $NR^{c2}C(O)OR^{a2}$, $NR^{c2}S(O)NR^{c2}R^{d2}$, $S(O)R^{b2}$, $S(O)NR^{c2}R^{d2}$, $S(O)_2R^{b2}$ $NR^{c2}S(O)_2R^{b2}$, and $S(O)_2NR^{c2}R^{d2}$;

each $R^{e1}$ is, independently, H, $C_{1-6}$alkyl, $C_{1-6}$haloalkyl, $C_{1-6}$hydroxyalkyl, $C_{2-6}$alkenyl, $C_{2-6}$alkynyl, aryl, cycloalkyl, heteroaryl, heterocycloalkyl, cycloalkylalkyl, heterocycloalkylalkyl, arylalkyl, or heteroarylalkyl;

each $R^{f1}$ is, independently, H, $C_{1-6}$alkyl, $C_{1-6}$haloalkyl, $C_{1-6}$hydroxyalkyl, $C_{2-6}$alkenyl, $(C_{1-6}$alkoxy$)$-$C_{1-6}$alkyl, $C_{2-6}$alkynyl, aryl, cycloalkyl, heteroaryl, heterocycloalkyl, arylalkyl, cycloalkylalkyl, heteroarylalkyl, or heterocycloalkylalkyl;

each $R^{g1}$ is, independently, H, $C_{1-6}$alkyl, $C_{1-6}$haloalkyl, $C_{1-6}$hydroxyalkyl, $C_{2-6}$alkenyl, $C_{2-6}$alkynyl, aryl, cycloalkyl, heteroaryl, or heterocycloalkyl; and each $R^{h1}$ is, independently, H, $C_{1-6}$alkyl, $C_{1-6}$haloalkyl, $C_{1-6}$hydroxyalkyl, $C_{2-6}$alkenyl, $C_{2-6}$alkynyl, aryl, cycloalkyl, heteroaryl, heterocycloalkyl, cycloalkylalkyl, heterocycloalkylalkyl, arylalkyl, or heteroarylalkyl;

or a pharmaceutically acceptable salt thereof.

In some embodiments, the lyn kinase activator is a compound of the formula:

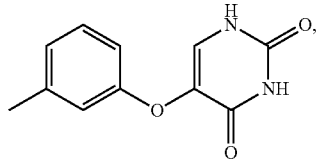

(Compound 116)

which is also known as 5-(m-tolyloxy)pyrimidine-2,4(1H,3H)-dione.

In some embodiments, the TRPM8 agonist is menthol, icilin, WS 3, or WS 23. In some embodiments, the TRPM8 agonist is menthol. Icilin (CAS 36945-98-9) is also known as 3-(2-hydroxyphenyl)-6-(3-nitrophenyl)-3,4-dihydropyrimidin-2(1H)-one, and has the formula:

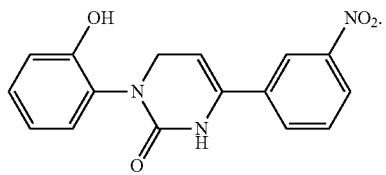 [SMILES: O=C1NC(c2cccc([N+](=O)[O-])c2)=CCN1c1ccccc1O]

WS 3 (CAS 39711-79-0) is also known as N-ethyl-2-isopropyl-5-methylcyclo-hexanecarboxamide, and has the formula:

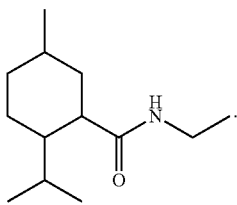

WS 23 (CAS 51115-67-4) is also known as N,2,3-trimethyl-2-propan-2-ylbutanamide, and has the formula:

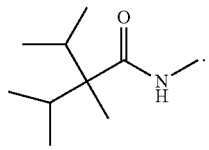

In some embodiments, more than one TRPM8 agonist can be used with one or more lyn kinase activators.

In some embodiments, the composition comprises Compound 102 and menthol. In some embodiments, no other active ingredient is present in the composition.

In some embodiments, the compositions described herein are pharmaceutical compositions and comprise a pharmaceutically acceptable carrier, vehicle, diluent, or excipient.

It will be understood that the compounds are illustrative only and not intended to limit the scope of the claims to only those compounds.

The compounds described herein can be synthesized by standard organic chemistry techniques known to those of ordinary skill in the art, for example as described in U.S. Pat. Nos. 3,922,345 and 4,080,454, each of which is incorporated herein by reference in its entirety.

Preparation of the compounds described herein can involve the protection and deprotection of various chemical groups. The need for protection and deprotection, and the selection of appropriate protecting groups, can be readily determined by one skilled in the art. The chemistry of protecting groups can be found, for example, in T. W. Greene and P. G. M. Wuts, Protective Groups in Organic Synthesis, 3rd Ed., Wiley & Sons, Inc., New York (1999), which is incorporated herein by reference in its entirety. Suitable hydroxyl protecting groups include, but are not limited to, tert-butyldimethylsilyl (TBS), methoxymethyl ether (MOM), tetrahydropyranyl ether (THP), t-Butyl ether, allyl ether, benzyl ether, t-Butyldimethylsilyl ether (TBDMS), t-Butyldiphenylsilyl ether (TBDPS), acetic acid ester, and the like.

The compositions described herein contain a therapeutically effective amount of one or more of the lyn kinase activators and one or more TRPM8 agonists, such as menthol, together with a suitable amount of a pharmaceutically acceptable vehicle to provide the desired form for administration to the patient.

Vehicles include, but are not limited to a diluent, adjuvant, excipient, or carrier with which a compound is administered. Such pharmaceutical vehicles can be liquids, such as water and oils, including those of petroleum, animal, vegetable or synthetic origin, such as peanut oil, soybean oil, mineral oil, sesame oil and the like. The pharmaceutical vehicles can be saline, gum acacia, gelatin, starch paste, talc, keratin, colloidal silica, urea, and the like. In addition, auxiliary, stabilizing, thickening, lubricating and coloring agents may be used. When administered to a patient, the compounds and pharmaceutically acceptable vehicles are preferably sterile. Water is a suitable vehicle when the compound is administered intravenously. Saline solutions and aqueous dextrose and glycerol solutions can also be employed as liquid vehicles, particularly for injectable solutions. Suitable pharmaceutical vehicles also include excipients such as starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The present compositions, if desired, can also contain minor amounts of wetting or emulsifying agents, or pH buffering agents.

The present compositions can take the form of solutions, suspensions, emulsion, tablets, pills, pellets, capsules, capsules containing liquids, powders, sustained-release formulations, suppositories, emulsions, aerosols, sprays, suspensions, or any other form suitable for use. In some embodiments, the pharmaceutically acceptable vehicle is a capsule (see e.g., U.S. Pat. No. 5,698,155). Other examples of suitable pharmaceutical vehicles are described in Remington's Pharmaceutical Sciences, A. R. Gennaro (Editor) Mack Publishing Co.

The compounds can be contained in such formulations with pharmaceutically acceptable diluents, fillers, disintegrants, binders, lubricants, surfactants, hydrophobic vehicles, water soluble vehicles, emulsifiers, buffers, humectants, moisturizers, solubilizers, preservatives and the like. The pharmaceutical compositions can also comprise suitable solid or gel phase carriers or excipients. Examples of such carriers or excipients include, but are not limited to, calcium carbonate, calcium phosphate, various sugars, starches, cellulose derivatives, gelatin, and polymers such as polyethylene glycols. In some embodiments, the compounds described herein can be used with agents including, but not limited to, topical analgesics (e.g., lidocaine), barrier devices (e.g., GelClair), or rinses (e.g., Caphosol).

Suitable compositions include, but are not limited to, oral non-absorbed compositions. Suitable compositions also include, but are not limited to saline, water, cyclodextrin solutions, and buffered solutions of pH 3-9.

The compounds described herein, or pharmaceutically acceptable salts thereof, can be formulated with numerous excipients including, but not limited to, purified water, propylene glycol, PEG 400, glycerin, DMA, ethanol, benzyl alcohol, citric acid/sodium citrate (pH3), citric acid/sodium citrate (pH5), tris(hydroxymethyl)amino methane HCl (pH7.0), 0.9% saline, and 1.2% saline, and any combination thereof. In some embodiments, excipient is chosen from propylene glycol, purified water, and glycerin.

In some embodiments, the formulation can be lyophilized to a solid and reconstituted with, for example, water prior to use.

When administered to a human, the compounds can be sterile. Water is a suitable carrier when the compound is administered intravenously. Saline solutions and aqueous dextrose and glycerol solutions can also be employed as liquid carriers, particularly for injectable solutions. Suitable pharmaceutical carriers also include excipients such as starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The present compositions, if desired, can also contain minor amounts of wetting or emulsifying agents, or pH buffering agents.

In some embodiments, the compounds are formulated in accordance with routine procedures as a pharmaceutical composition adapted for administration to humans. Typically, compounds are solutions in sterile isotonic aqueous buffer. Where necessary, the compositions can also include a solubilizing agent. Compositions for intravenous administration may optionally include a local anesthetic such as lidocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the compound is to be administered by infusion, it can be dispensed, for example, with an infusion bottle containing sterile pharmaceutical grade water or saline. Where the compound is administered by injection, an ampoule of sterile water for injection or saline can be provided so that the ingredients may be mixed prior to administration.

The pharmaceutical compositions can be in unit dosage form. In such form, the composition can be divided into unit doses containing appropriate quantities of the active component. The unit dosage form can be a packaged preparation, the package containing discrete quantities of the preparations, for example, packeted tablets, capsules, and powders in vials or ampules. The unit dosage form can also be a capsule, cachet, or tablet itself, or it can be the appropriate number of any of these packaged forms.

In some embodiments, a composition can be in the form of a liquid wherein the active agent (i.e., one of the facially amphiphilic polymers or oligomers disclosed herein) is present in solution, in suspension, as an emulsion, or as a solution/suspension. In some embodiments, the liquid composition is in the form of a gel. In other embodiments, the liquid composition is aqueous. In other embodiments, the composition is in the form of an ointment.

Suitable preservatives include, but are not limited to, mercury-containing substances such as phenylmercuric salts (e.g., phenylmercuric acetate, borate and nitrate) and thimerosal; stabilized chlorine dioxide; quaternary ammonium compounds such as benzalkonium chloride, cetyltrimethylammonium bromide and cetylpyridinium chloride; imidazolidinyl urea; parabens such as methylparaben, ethylparaben, propylparaben and butylparaben, and salts thereof; phenoxyethanol; chlorophenoxyethanol; phenoxypropanol; chlorobutanol; chlorocresol; phenylethyl alcohol; disodium EDTA; and sorbic acid and salts thereof.

Optionally one or more stabilizers can be included in the compositions to enhance chemical stability where required. Suitable stabilizers include, but are not limited to, chelating agents or complexing agents, such as, for example, the calcium complexing agent ethylene diamine tetraacetic acid (EDTA). For example, an appropriate amount of EDTA or a salt thereof, e.g., the disodium salt, can be included in the composition to complex excess calcium ions and prevent gel formation during storage. EDTA or a salt thereof can suitably be included in an amount of about 0.01% to about 0.5%. In those embodiments containing a preservative other than EDTA, the EDTA or a salt thereof, more particularly disodium EDTA, can be present in an amount of about 0.025% to about 0.1% by weight.

One or more antioxidants can also be included in the compositions. Suitable antioxidants include, but are not limited to, ascorbic acid, sodium metabisulfite, sodium bisulfite, acetylcysteine, polyquaternium-1, benzalkonium chloride, thimerosal, chlorobutanol, methyl paraben, propyl paraben, phenylethyl alcohol, edetate disodium, sorbic acid, or other agents know to those of skill in the art. Such preservatives are typically employed at a level of from about 0.001% to about 1.0% by weight.

In some embodiments, the compounds are solubilized at least in part by an acceptable solubilizing agent. Certain acceptable nonionic surfactants, for example polysorbate 80, can be useful as solubilizing agents, as can acceptable glycols, polyglycols, e.g., polyethylene glycol 400 (PEG-400), and glycol ethers.

Suitable solubilizing agents for solution and solution/suspension compositions are cyclodextrins. Suitable cyclodextrins include α-cyclodextrin, β-cyclodextrin, γ-cyclodextrin, alkylcyclodextrins (e.g., methyl-β-cyclodextrin, dimethyl-β-cyclodextrin, and diethyl-β-cyclodextrin), hydroxyalkylcyclodextrins (e.g., hydroxyethyl-β-cyclodextrin, hydroxypropyl-β-cyclodextrin), carboxy-alkylcyclodextrins (e.g., carboxymethyl-β-cyclodextrin), sulfoalkylether cyclodextrins (e.g., sulfobutylether-β-cyclodextrin), and the like. Applications of cyclodextrins have been reviewed in Rajewski et al., J. Pharm. Sciences, 1996, 85, 1155-1159. An acceptable cyclodextrin can optionally be present in a composition at a concentration from about 1 to about 200 mg/ml, from about 5 to about 100 mg/ml, or from about 10 to about 50 mg/ml.

In some embodiments, the composition optionally contains a suspending agent. For example, in those embodiments in which the composition is an aqueous suspension or solution/suspension, the composition can contain one or more polymers as suspending agents. Useful polymers include, but are not limited to, water-soluble polymers such as cellulosic polymers, for example, hydroxypropyl methylcellulose, and water-insoluble polymers such as cross-linked carboxyl-containing polymers. However, in some embodiments, compositions do not contain substantial amounts of solid particulate matter, whether of the antimicrobial polymer or oligomer active agent, an excipient, or both, as solid particulate matter, if present, can cause discomfort and/or irritation of a treated eye.

One or more acceptable pH adjusting agents and/or buffering agents can be included in the compositions, including acids such as acetic, boric, citric, lactic, phosphoric and hydrochloric acids; bases such as sodium hydroxide, sodium phosphate, sodium borate, sodium citrate, sodium acetate, sodium lactate and tris-hydroxymethylaminomethane; and buffers such as citrate/dextrose, sodium bicarbonate and ammonium chloride. Such acids, bases and buffers are included in an amount required to maintain pH of the composition in an acceptable range.

Optionally one or more acceptable surfactants, such as nonionic surfactants, or co-solvents can be included in the compositions to enhance solubility of the components of the compositions or to impart physical stability, or for other purposes. Suitable nonionic surfactants include, but are not limited to, polyoxyethylene fatty acid glycerides and vegetable oils, e.g., polyoxyethylene (60) hydrogenated castor oil; and polyoxyethylene alkylethers and alkylphenyl ethers, e.g., octoxynol 10, octoxynol 40; polysorbate 20, 60 and 80; polyoxyethylene/polyoxypropylene surfactants (e.g., Pluronic® F-68, F84 and P-103); cyclodextrin; or other agents known to those of skill in the art. Typically, such co-solvents or surfactants are employed in the compositions at a level of from about 0.01% to about 2% by weight.

One or more lubricating agents can also be included optionally in the compositions to promote lacrimation or as a "dry eye" medication. Such agents include, but are not limited to, polyvinyl alcohol, methylcellulose, hydroxypropyl methylcellulose, polyvinylpyrrolidone, and the like. It will be understood that promotion of lacrimation is beneficial in the present invention only where lacrimation is naturally deficient, to restore a normal degree of secretion of lacrimal fluid. Where excessive lacrimation occurs, residence time of the composition in the eye can be reduced.

The compounds described herein can be formulated for parenteral administration by injection, such as by bolus injection or continuous infusion. The compounds can be administered by continuous infusion subcutaneously over a period of about 15 minutes to about 24 hours. Formulations for injection can be presented in unit dosage form, such as in ampoules or in multi-dose containers, with an added preservative. The compositions can take such forms as suspensions, solutions or emulsions in oily or aqueous vehicles, and can contain formulatory agents such as suspending, stabilizing and/or dispersing agents. In some embodiments, the injectable is in the form of short-acting, depot, or implant and pellet forms injected subcutaneously or intramuscularly. In some embodiments, the parenteral dosage form is the form of a solution, suspension, emulsion, or dry powder.

In some embodiments, the compounds are formulated in accordance with routine procedures as a pharmaceutical composition adapted for intravenous administration to human beings. Typically, compounds for intravenous administration are solutions in sterile isotonic aqueous buffer. Where necessary, the compositions may also include a solubilizing agent. Compositions for intravenous administration may optionally include a local anesthetic such as lidocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the compound is to be administered by infusion, it can be dispensed, for example, with an infusion bottle containing sterile pharmaceutical grade water or saline. Where the compound is administered by injection, an ampoule of sterile water for injection or saline can be provided so that the ingredients may be mixed prior to administration.

The compounds described herein can also be formulated as a depot preparation. Such long acting formulations can be administered by implantation (for example subcutaneously or intramuscularly) or by intramuscular injection. Depot injections can be administered at about 1 to about 6 months or longer intervals. Thus, for example, the compounds can be formulated with suitable polymeric or hydrophobic materials (for example as an emulsion in an acceptable oil) or ion exchange resins, or as sparingly soluble derivatives, for example, as a sparingly soluble salt.

In some embodiments, the compositions can be administered orally. Compositions for oral delivery may be in the form of tablets, lozenges, aqueous or oily suspensions, granules, powders, emulsions, capsules, syrups, or elixirs, for example. Orally administered compositions may contain one or more optionally agents, for example, sweetening agents such as fructose, aspartame or saccharin; flavoring agents such as peppermint, oil of wintergreen, or cherry; coloring agents; and preserving agents, to provide a pharmaceutically palatable preparation. Moreover, where in tablet or pill form, the compositions may be coated to delay disintegration and absorption in the gastrointestinal tract thereby providing a sustained action over an extended period of time. Selectively permeable membranes surrounding an osmotically active driving compound are also suitable for orally administered compounds. In these later platforms, fluid from the environment surrounding the capsule is imbibed by the driving compound, which swells to displace the agent or agent composition through an aperture. These delivery platforms can provide an essentially zero order delivery profile as opposed to the spiked profiles of immediate release formulations. A time delay material such as glycerol monostearate or glycerol stearate may also be used. Oral compositions can include standard vehicles such as mannitol, lactose, starch, magnesium stearate, sodium saccharine, cellulose, magnesium carbonate, etc. Such vehicles can be pharmaceutical grade.

For oral administration, the compounds described herein can be formulated by combining the compounds with pharmaceutically acceptable carriers well known in the art. Such carriers enable the compounds to be formulated as tablets, pills, dragees, capsules, emulsions, liquids, gels, syrups, caches, pellets, powders, granules, slurries, lozenges, aqueous or oily suspensions, and the like, for oral ingestion by a patient to be treated. Pharmaceutical preparations for oral use can be obtained by, for example, adding a solid excipient, optionally grinding the resulting mixture, and processing the mixture of granules, after adding suitable auxiliaries, if desired, to obtain tablets or dragee cores. Suitable excipients include, but are not limited to, fillers such as sugars, including, but not limited to, lactose, sucrose, mannitol, and sorbitol; cellulose preparations such as, but not limited to, maize starch, wheat starch, rice starch, potato starch, gelatin, gum tragacanth, methyl cellulose, hydroxypropylmethylcellulose, sodium carboxymethylcellulose, and polyvinylpyrrolidone (PVP). If desired, disintegrating agents can be added, such as, but not limited to, the cross-linked polyvinyl pyrrolidone, agar, or alginic acid or a salt thereof such as sodium alginate.

Orally administered compositions can contain one or more optional agents, for example, sweetening agents such as fructose, aspartame or saccharin; flavoring agents such as peppermint, oil of wintergreen, or cherry; coloring agents; and preserving agents, to provide a pharmaceutically palatable preparation. Moreover, where in tablet or pill form, the compositions may be coated to delay disintegration and absorption in the gastrointestinal tract thereby providing a sustained action over an extended period of time. Selectively permeable membranes surrounding an osmotically active driving compound are also suitable for orally administered compounds. Oral compositions can include standard vehicles such as mannitol, lactose, starch, magnesium stearate, sodium saccharine, cellulose, magnesium carbonate, etc. Such vehicles are suitably of pharmaceutical grade.

Dragee cores can be provided with suitable coatings. For this purpose, concentrated sugar solutions can be used, which can optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments can be added to the tablets or dragee coatings for identification or to characterize different combinations of active compound doses.

Pharmaceutical preparations which can be used orally include, but are not limited to, push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds can be dissolved or suspended in suitable liquids, such as fatty oils, liquid paraffin, or liquid polyethylene glycols. In addition, stabilizers can be added.

For buccal administration, the compositions can take the form of, such as, tablets or lozenges formulated in a conventional manner.

In some embodiments, the compounds can be delivered in a controlled release system. In one embodiment, a pump may be used (see Langer, supra; Sefton, CRC Crit. Ref. Biomed. Eng., 1987, 14, 201; Buchwald et al., Surgery, 1980, 88, 507 Saudek et al., N. Engl. J. Med., 1989, 321, 574). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger et al., J. Macromol. Sci. Rev. Macromol. Chem., 1983, 23, 61; see, also Levy et al., Science, 1985, 228, 190; During et al., Ann. Neurol., 1989, 25, 351; Howard et al., J. Neurosurg., 1989, 71, 105). In yet another embodiment, a controlled-release system can be placed in proximity of the target of the compounds described herein, such as the liver, thus requiring only a fraction of the systemic dose (see, e.g., Goodson, in Medical Applications of Controlled Release, supra, vol. 2, pp. 115-138 (1984)). Other controlled-release systems discussed in the review by Langer, Science, 1990, 249, 1527-1533) may be used.

In some embodiments, the compounds described herein can be delivered in a vesicle, in particular a liposome (see, Langer, Science, 1990, 249, 1527-1533; Treat et al., in Liposomes in the Therapy of Infectious Disease and Cancer, Lopez-Berestein and Fidler (eds.), Liss, New York, pp. 353-365 (1989); Lopez-Berestein, ibid., pp. 317-327; see generally ibid.).

For administration by inhalation, the compounds described herein can be delivered in the form of an aerosol spray presentation from pressurized packs or a nebulizer, with the use of a suitable propellant, such as dichlorodifluoromethane, trichlorofluoromethane, dichlorotetrafluoroethane, carbon dioxide or other suitable gas. In the case of a pressurized aerosol the dosage unit can be determined by providing a valve to deliver a metered amount. Capsules and cartridges of, such as gelatin for use in an inhaler or insufflator can be formulated containing a powder mix of the compound and a suitable powder base such as lactose or starch.

The compounds described herein can also be formulated in rectal compositions such as suppositories or retention enemas, such as containing conventional suppository bases such as cocoa butter or other glycerides. The compounds described herein can also be formulated in vaginal compositions such as vaginal creams, suppositories, pessaries, vaginal rings, and intrauterine devices.

In transdermal administration, the compounds can be applied to a plaster, or can be applied by transdermal, therapeutic systems that are consequently supplied to the organism. In some embodiments, the compounds are present in creams, solutions, powders, fluid emulsions, fluid suspensions, semi-solids, ointments, pastes, gels, jellies, and foams, or in patches containing any of the same.

The amount of a lyn kinase activator that will be effective in the treatment of a particular disorder or condition disclosed herein will depend on the nature of the disorder or condition, and can be determined by standard clinical techniques. In addition, in vitro or in vivo assays may optionally be employed to help identify optimal dosage ranges. The precise dose to be employed in the compositions will also depend on the route of administration, and the seriousness of the disease or disorder, and should be decided according to the judgment of the practitioner and each patient's circumstances. However, suitable dosage ranges for oral administration are generally about 0.001 milligram to 200 milligrams of a compound per kilogram body weight. In some embodiments, the oral dose is about 0.01 milligram to about 70 milligrams per kilogram body weight, about 0.1 milligram to about 50 milligrams per kilogram body weight, about 0.5 milligram to about 20 milligrams per kilogram body weight, about 1 milligram to about 10 milligrams per kilogram body weight, or about 5 milligrams of a compound per kilogram body weight. The dosage amounts described herein refer to total amounts administered; that is, if more than one compound is administered, the dosages correspond to the total amount of the compounds administered. Oral compositions can contain 10% to 95% active ingredient by weight.

Suitable dosage ranges for intravenous (i.v.) administration are about 0.01 milligram to about 100 milligrams per kilogram body weight, about 0.1 milligram to about 35 milligrams per kilogram body weight, and about 1 milligram to about 10 milligrams per kilogram body weight. Suitable dosage ranges for intranasal administration are generally about 0.01 pg/kg body weight to about 1 mg/kg body weight. Suppositories generally contain about 0.01 milligram to about 50 milligrams of a compound per kilogram body weight and comprise active ingredient in the range of about 0.5% to about 10% by weight. Recommended dosages for intradermal, intramuscular, intraperitoneal, subcutaneous, epidural, sublingual, intracerebral, intravaginal, transdermal administration or administration by inhalation are in the range of about 0.001 milligram to about 200 milligrams per kilogram of body weight. Suitable doses of the compounds for topical administration are in the range of about 0.001 milligram to about 1 milligram, depending on the area to which the compound is administered. Effective doses may be extrapolated from dose-response curves derived from in vitro or animal model test systems. Such animal models and systems are well known in the art.

The amount of TRPM8 agonist that will be effective in the treatment of a particular disorder or condition disclosed herein will depend on the nature of the disorder or condition, and can be determined by standard clinical techniques. In addition, in vitro or in vivo assays may optionally be employed to help identify optimal dosage ranges. The precise dose to be employed in the compositions will also depend on the route of administration, and the seriousness of the disease or disorder, and should be decided according to the judgment of the practitioner and each patient's circumstances. However, suitable dosage ranges for administration of the TRPM8 agonist are generally from about 0.01 μM to about 200 μM, from about 0.1 μM to about 150 μM, from about 1 μM to about 100 μM, from about 5 μM to about 50 μM, from about 10 μM to about 40 μM, from about 15 μM to about 35 μM, or from about 20 μM to about 30 μM. In some embodiments, a suitable dosage for administration of the TRPM8 agonist is about 0.1 μM, about 1 μM, about 5 μM, about 10 μM, about 15 μM, about 20 μM, about 25 μM, about 30 μM, about 35 μM, about 40 μM, about 45 μM, about 50 μM, about 55 μM, about 60 μM, about 65 μM, about 70 μM, about 75 μM, about 80 μM, about 85 μM, about 90 μM, about 95 μM, about 100 μM, about 105 μM, about 110 μM, about 115 μM, about 120 μM, about 125 μM, about 130 μM, about 135 μM, about 140 μM, about 145 μM, about 150 μM, about 155 μM, about 160 μM, about 165 μM, about 170 μM, about 175 μM, about 180 μM, about 185 μM, about 190 μM, about 195 μM, or about 200 μM.

The present disclosure also provides pharmaceutical packs or kits comprising one or more containers filled with one or more compositions. Optionally associated with such container(s) can be a notice in the form prescribed by a governmental agency regulating the manufacture, use or sale of pharmaceuticals or biological products, which notice reflects approval by the agency of manufacture, use or sale for human administration. In some embodiments, the kit contains more than one lyn kinase activator. In some embodiments, the kit contains more than one TRPM8 agonist. In some embodiments, the kit comprises a lyn kinase activator and TRPM8 agonist in separate containers.

In some embodiments, the compositions can be used in combination therapy with at least one other therapeutic agent. The compound and the additional therapeutic agent can act additively or synergistically. In some embodiments, a composition described herein is administered concurrently with the administration of another therapeutic agent, which can be part of the same composition as the compound or a different composition. In some embodiments, a composition described herein is administered prior or subsequent to administration of another therapeutic agent. As many of the disorders for which the compositions are useful in treating are chronic disorders, in some embodiments the combination therapy involves alternating between administering a composition described herein and a composition comprising another therapeutic agent, e.g., to minimize the toxicity associated with a particular drug. The duration of administration of each drug or therapeutic agent can be, e.g., one month, three months, six months, or a year. In some embodiments, when a composition described herein is administered concurrently with another therapeutic agent that potentially produces adverse side effects, including but not limited to, toxicity, the therapeutic agent can advantageously be administered at a dose that falls below the threshold at which the adverse side is elicited.

The present compositions can be administered together or separately, with a statin. Statins include but are not limited to atorvastatin, pravastatin, fluvastatin, lovastatin, simvastatin, and cerivastatin. In some embodiments, the composition comprises a lyn kinase activator, a TRPM8 agonist, and a statin.

The present compositions can also be administered together, or separately, with a PPAR agonist, for example a thiazolidinedione or a fibrate. Thiazolidinediones include but are not limited to 5-((4-(2-(methyl-2-pyridinylamino) ethoxy)phenyl)methyl)-2,4-thiazolidinedione, troglitazone, pioglitazone, ciglitazone, WAY-120,744, englitazone, AD 5075, darglitazone, and rosiglitazone. Fibrates include but are not limited to gemfibrozil, fenofibrate, clofibrate, or ciprofibrate. As mentioned previously, a therapeutically effective amount of a fibrate or thiazolidinedione often has toxic side effects. Accordingly, in some embodiments, when a composition described herein is administered in combination with a PPAR agonist, the dosage of the PPAR agonist is below that which is accompanied by toxic side effects. In some embodiments, the composition comprises a lyn kinase activator, a TRPM8 agonist, and a PPAR agonist.

The present compositions can also be administered together, or separately, with a bile-acid-binding resin. Bile-acid-binding resins include but are not limited to cholestyramine and colestipol hydrochloride. In some embodiments, the composition comprises a lyn kinase activator, a TRPM8 agonist, and a bile-acid-binding resin.

The present compositions can also be administered together, or separately, with niacin or nicotinic acid. In some embodiments, the composition comprises a lyn kinase activator, a TRPM8 agonist, and niacin or nicotinic acid.

The present compositions can also be administered together, or separately, with a RXR agonist. RXR agonists include but are not limited to LG 100268, LGD 1069, 9-cis retinoic acid, 2-(1-(3,5,5,8,8-pentamethyl-5,6,7,8-tetrahydro-2-naphthyl)-cyclopropyl)-pyridine-5-carboxylic acid, or 4-((3,5,5,8,8-pentamethyl-5,6,7,8-tetrahydro-2-naphthyl)$_2$ -carbonyl)-benzoic acid. In some embodiments, the composition comprises a lyn kinase activator, a TRPM8 agonist, and a RXR agonist.

The present compositions can also be administered together, or separately, with an anti-obesity drug. Anti-obesity drugs include but are not limited to 0-adrenergic receptor agonists, preferably β-3 receptor agonists, sibutramine, bupropion, fluoxetine, and phentermine. In some embodiments, the composition comprises a lyn kinase activator, a TRPM8 agonist, and an anti-obesity drug.

The present compositions can also be administered together, or separately, with a hormone. Hormones include but are not limited to thyroid hormone, estrogen and insulin. Suitable insulins include but are not limited to injectable insulin, transdermal insulin, inhaled insulin, or any combination thereof. As an alternative to insulin, an insulin derivative, secretagogue, sensitizer or mimetic may be used. Insulin secretagogues include but are not limited to forskolin, dibutryl cAMP or isobutylmethylxanthine (IBMX). In some embodiments, the composition comprises a lyn kinase activator, a TRPM8 agonist, and a hormone.

The present compositions can also be administered together, or separately, with a tyrophostine or an analog thereof. Tyrophostines include but are not limited to tryophostine 51. In some embodiments, the composition comprises a lyn kinase activator, a TRPM8 agonist, and tyrophostine or an analog thereof.

The present compositions can also be administered together, or separately, with sulfonylurea-based drugs.

Sulfonylurea-based drugs include, but are not limited to, glisoxepid, glyburide, acetohexamide, chlorpropamide, glibornuride, tolbutamide, tolazamide, glipizide, gliclazide, gliquidone, glyhexamide, phenbutamide, and tolcyclamide. In some embodiments, the composition comprises a lyn kinase activator, a TRPM8 agonist, and a sulfonylurea-based drug.

The present compositions can also be administered together, or separately, with a biguanide. Biguanides include but are not limited to metformin, phenformin and buformin. In some embodiments, the composition comprises a lyn kinase activator, a TRPM8 agonist, and a biguanide.

The present compositions can also be administered together, or separately, with an α-glucosidase inhibitor. α-glucosidase inhibitors include but are not limited to acarbose and miglitol. In some embodiments, the composition comprises a lyn kinase activator, a TRPM8 agonist, and an α-glucosidase inhibitor.

The present compositions can also be administered together, or separately, with an apo A-I agonist. In some embodiments, the apo A-I agonist is the Milano form of apo A-I (apo A-IM). In some embodiments, the apo A-IM is produced by the method of U.S. Pat. No. 5,721,114. In some embodiments, the apo A-I agonist is a peptide agonist. In some embodiments, the apo A-I peptide agonist is a peptide of U.S. Pat. No. 6,004,925 or 6,037,323. The present compositions can also be administered together with apolipoprotein E (apo E). In some embodiments, the apoE is produced by the method of U.S. Pat. No. 5,834,596. In some embodiments, the present compositions can be administered together with an HDL-raising drug; an HDL enhancer; or a regulator of the apolipoprotein A-I, apolipoprotein A-IV and/or apolipoprotein genes. In some embodiments, the composition comprises a lyn kinase activator, a TRPM8 agonist, and an apo A-I agonist.

The present compositions can be administered together, or separately, with a known cardiovascular drug. Cardiovascular drugs include but are not limited to peripheral antiadrenergic drugs, centrally acting antihypertensive drugs (e.g., methyldopa, methyldopa HCl), antihypertensive direct vasodilators (e.g., diazoxide, hydralazine HCl), drugs affecting renin-angiotensin system, peripheral vasodilators, phentolamine, antianginal drugs, cardiac glycosides, inodilators (e.g., amrinone, milrinone, enoximone, fenoximone, imazodan, sulmazole), antidysrhythmic drugs, calcium entry blockers, ranitine, bosentan, and rezulin. In some embodiments, the composition comprises a lyn kinase activator, a TRPM8 agonist, and a cardiovascular drug.

The present compositions can also comprise, and be administered together, or separately, with a GLP-1 agonist such as, for example, liraglutide (VICTOZA®, SAXENDA®), exenatide (BYETTA®, BYDUREON®), lixisenatide (LYXUMIA®), albiglutide (TANZEUM®), dulaglutide (TRULICITY®), and semaglutide (OZEMPIC®). In some embodiments, the composition comprises a lyn kinase activator, a TRPM8 agonist, and a GLP-1 agonist.

The present compositions can also comprise, and be administered together, or separately, with a PPARα/δ dual agonist such as, for example, Elafibranor. In some embodiments, the composition comprises a lyn kinase activator, a TRPM8 agonist, and a PPARα/δ dual agonist.

The present compositions can also comprise, and be administered together, or separately, with an ACC inhibitor such as, for example, GS-0976. In some embodiments, the composition comprises a lyn kinase activator, a TRPM8 agonist, and an ACC inhibitor.

The present compositions can also comprise, and be administered together, or separately, with a growth factor such as, for example, Pegylated FGF21. In some embodiments, the composition comprises a lyn kinase activator, a TRPM8 agonist, and a growth factor.

The present compositions can also comprise, and be administered together, or separately, with a CCR2/5 blocker such as, for example, Ceniciviroc (CVC). In some embodiments, the composition comprises a lyn kinase activator, a TRPM8 agonist, and a CCR2/5 blocker.

The present compositions can also comprise, and be administered together (e.g., within the same composition), or separately, with any one or more of the following: hexadecanoic acid, linoleic acid, phloretin, Vitamin D3, docosanoic acid, quercetin, D-erythro-sphingosine, ricinoleic acid, dodecanoic acid, gossypol, ellagic acid, damnacanthal, heptadecanoic acid, gamma-linolenic acid eicosanoic acid, arachidonic acid, pentacosanoic acid, hexacosanoic acid, dequalinium chloride, tetradecanoic acid, hispidin, tetracosanoic acid, tridecanoic acid, DL-3,4-dihydroxymandelic acid, pentadecanoic acid, ETYA, MNS, palmitoyl-DL-carnitine, adrenic acid, thiazolidinedione, heneicosanoic acid, tricosanoic acid, chelerythrine chloride, aminoindole, docosahexaenoic acid, 5-amino-2-methylindole, cobalt chloride ($CoCl_2$), piceatannol, eicosapentaenoic acid, sodium nitride ($Na_3N$), radicicol, safingol, myricitrin, 13-HODE, calcifediol, mead acid, 5-iodotubercidin, sphingosine-1-phosphate, docosadienoic acid, heptadecenoic acid, geldanamycin, calcitriol, eicosadienoic acid, melittin, 4-hydroxy-tamoxifen, hydroxyeicosatetraenoic acid, herbimycin A, ET-18-OCH$_3$, 15-HETE, 5-HETE, eicosatrienoic acid, bryostatin 1, ilmofosine, H-9, H-8, K-252c, HA-1004, K-252a, K-252b, HA-1077, 9-HODE, MDL-27032, UCN-01, bisindolylmaleimide V, calphostin C, 7-oxostaurosporine, bisindolylmaleimide VIII, lavendustin A, lavendustin C, KRIBB3, bisindolylmaleimide X, bisindolylmaleimide I, NGIC-I, Go 6976, bisindolylmaleimide III, bisindolylmaleimide II, bisindolylmaleimide VI, bisindolylmaleimide VII, dihydrochloride, Pp60 c-src, Ro-32-0432, Go 7874, fingolimod, enzastaurin, PP1, PP2, HA-100 dihydrochloride, PD 166285, PP1, 1-NM-PP1, CGP77675, PD 180970, dasatinib, PD173952, SU 6656, A-419259, saracatinib, bosutinib, sotrastaurin, KX1-004, CID 755673, ZM 306416, AZM 475271, WH-4-023, TC-S 7003, dasatinib monohydrate, TG 100572, A-770041, KX2-391, NVP-BHG712, ER 27319 maleate, TCS 21311, KB SRC 4, and PKC 20-28.

The present compositions can be administered together, or separately, with treatment with irradiation or one or more chemotherapeutic agents. For irradiation treatment, the irradiation can be gamma rays or X-rays. Useful chemotherapeutic agents include, but are not limited to, methotrexate, taxol, mercaptopurine, thioguanine, hydroxyurea, cytarabine, cyclophosphamide, ifosfamide, nitrosoureas, cisplatin, carboplatin, mitomycin, dacarbazine, procarbizine, etoposides, campathecins, bleomycin, doxorubicin, idarubicin, daunorubicin, dactinomycin, plicamycin, mitoxantrone, asparaginase, vinblastine, vincristine, vinorelbine, paclitaxel, and docetaxel. In some embodiments, a composition described herein further comprises one or more chemotherapeutic agents and/or is administered concurrently with radiation therapy. In some embodiments, chemotherapy or radiation therapy is administered prior or subsequent to administration of a present composition, at least an hour, five hours, 12 hours, a day, a week, a month, or several months (e.g., up to three months), subsequent to administration of a composition described herein.

The present disclosure also provides methods of reducing blood glucose levels, weight gain, or fat depot levels in a mammal in need thereof, comprising administering to the mammal an effective amount of any one or more of the compositions described herein, or comprising administering a lyn kinase activator and a TRPM8 agonist in separate administrations. Any combination of lyn kinase activator and a TRPM8 agonist can be used in the present methods.

The present disclosure also provides methods of treating metabolic syndrome, Syndrome X, obesity, prediabetes, type II diabetes, type I diabetes in a mammal in need thereof, comprising administering to the mammal an effective amount of any one or more of the compositions described herein, or comprising administering a lyn kinase activator and a TRPM8 agonist in separate administrations. Any combination of lyn kinase activator and a TRPM8 agonist can be used in the present methods.

The present disclosure also provides methods of treating hypercholesterolemia, hypertension, coronary heart disease, diabetic neuropathy, lipodystrophy, diabetic retinopathy, erectile dysfunction, kidney disease, dyslipidemia, dyslipoproteinemia, a peroxisome proliferator activated receptor-associated disorder, septicemia, a thrombotic disorder, or pancreatitis in a mammal in need thereof, comprising administering to the mammal an effective amount of any one or more of the compositions described herein, or comprising administering a lyn kinase activator and a TRPM8 agonist in separate administrations. Any combination of lyn kinase activator and a TRPM8 agonist can be used in the present methods.

The present disclosure also provides methods of inducing the beiging of adipocytes in a mammal in need thereof, comprising administering to the mammal an effective amount of any one or more of the compositions described herein, or comprising administering a lyn kinase activator and a TRPM8 agonist in separate administrations. Any combination of lyn kinase activator and a TRPM8 agonist can be used in the present methods.

The present disclosure also provides methods of preventing pancreatic beta cell degeneration in a mammal in need thereof, comprising administering to the mammal an effective amount of any one or more of the compositions described herein, or comprising administering a lyn kinase activator and a TRPM8 agonist in separate administrations. Any combination of lyn kinase activator and a TRPM8 agonist can be used in the present methods.

The present compositions can be administered orally. The compositions can also be administered by any other convenient route, for example, by infusion or bolus injection, by absorption through epithelial or mucocutaneous linings (e.g., oral mucosa, rectal and intestinal mucosa, etc.) and can be administered together with another biologically active agent. Administration can be systemic or local. Various delivery systems are known, e.g., encapsulation in liposomes, microparticles, microcapsules, capsules, etc., and can be used to administer the compositions. In some embodiments, more than one composition is administered to a patient. Methods of administration include, but are not limited to intradermal, intramuscular, intraperitoneal, intravenous, subcutaneous, intranasal, epidural, oral, sublingual, intranasal, intracerebral, intravaginal, transdermal, rectally, by inhalation, or topically, particularly to the ears, nose, eyes, or skin. The desired mode of administration is left to the discretion of the practitioner, and will depend in-part upon the site of the medical condition.

In some embodiments, it may be desirable to administer one or more compositions locally to the area in need of treatment. This may be achieved, for example, and not by way of limitation, by local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers. In some embodiments, administration can be by direct injection at the site (or former site) of an atherosclerotic plaque tissue.

Pulmonary administration can also be employed, e.g., by use of an inhaler or nebulizer, and formulation with an aerosolizing agent, or via perfusion in a fluorocarbon or synthetic pulmonary surfactant. In some embodiments, the compositions can be formulated as a suppository, with traditional binders and vehicles such as triglycerides.

The present disclosure also provides compositions described herein for use in reducing blood glucose levels, weight gain, or fat depot levels in a mammal in need thereof, comprising administering to the mammal an effective amount of any one or more of the compositions described herein.

The present disclosure also provides compositions described herein for use in treating metabolic syndrome, Syndrome X, obesity, prediabetes, type II diabetes, type I diabetes in a mammal in need thereof, comprising administering to the mammal an effective amount of any one or more of the compositions described herein.

The present disclosure also provides compositions described herein for use in treating hypercholesterolemia, hypertension, coronary heart disease, diabetic neuropathy, lipodystrophy, diabetic retinopathy, erectile dysfunction, kidney disease, dyslipidemia, dyslipoproteinemia, a peroxisome proliferator activated receptor-associated disorder, septicemia, a thrombotic disorder, or pancreatitis in a mammal in need thereof, comprising administering to the mammal an effective amount of any one or more of the compositions described herein.

The present disclosure also provides compositions described herein for use in inducing the beiging of adipocytes in a mammal in need thereof, comprising administering to the mammal an effective amount of any one or more of the compositions described herein. In some embodiments, a lyn kinase activator, such as Compound 102, can be used without a TRPM8 agonist to induce beiging of adipocytes in a mammal in need thereof.

The present disclosure also provides compositions described herein for use in preventing pancreatic beta cell degeneration in a mammal in need thereof, comprising administering to the mammal an effective amount of any one or more of the compositions described herein.

The present disclosure also provides lyn kinase activators and TRPM8 agonist for use in reducing blood glucose levels, weight gain, or fat depot levels in a mammal in need thereof, comprising administering to the mammal an effective amount of any one or more of the compositions described herein.

The present disclosure also provides lyn kinase activators and TRPM8 agonist for use in treating metabolic syndrome, Syndrome X, obesity, prediabetes, type II diabetes, type I diabetes in a mammal in need thereof, comprising administering to the mammal an effective amount of any one or more of the compositions described herein.

The present disclosure also provides lyn kinase activators and TRPM8 agonist for use in treating hypercholesterolemia, hypertension, coronary heart disease, diabetic neuropathy, lipodystrophy, diabetic retinopathy, erectile dysfunction, kidney disease, dyslipidemia, dyslipoproteinemia, a peroxisome proliferator activated receptor-associated disorder, septicemia, a thrombotic disorder, or pancreatitis in a mammal in need thereof, comprising administering to the mammal an effective amount of any one or more of the compositions described herein.

The present disclosure also provides lyn kinase activators and TRPM8 agonist for use in inducing the beiging of adipocytes in a mammal in need thereof, comprising administering to the mammal an effective amount of any one or more of the compositions described herein. In some embodiments, a lyn kinase activator, such as Compound 102, can be used without a TRPM8 agonist to induce beiging of adipocytes in a mammal in need thereof.

The present disclosure also provides lyn kinase activators and TRPM8 agonist for use in preventing pancreatic beta cell degeneration in a mammal in need thereof, comprising administering to the mammal an effective amount of any one or more of the compositions described herein.

The present disclosure also provides compositions described herein for use in preparation of a medicament for reducing blood glucose levels, weight gain, or fat depot levels in a mammal in need thereof, comprising administering to the mammal an effective amount of any one or more of the compositions described herein.

The present disclosure also provides compositions described herein for use in preparation of a medicament for treating metabolic syndrome, Syndrome X, obesity, prediabetes, type II diabetes, type I diabetes in a mammal in need thereof, comprising administering to the mammal an effective amount of any one or more of the compositions described herein.

The present disclosure also provides compositions described herein for use in preparation of a medicament for treating hypercholesterolemia, hypertension, coronary heart disease, diabetic neuropathy, lipodystrophy, diabetic retinopathy, erectile dysfunction, kidney disease, dyslipidemia, dyslipoproteinemia, a peroxisome proliferator activated receptor-associated disorder, septicemia, a thrombotic disorder, or pancreatitis in a mammal in need thereof, comprising administering to the mammal an effective amount of any one or more of the compositions described herein.

The present disclosure also provides compositions described herein for use in preparation of a medicament for inducing the beiging of adipocytes in a mammal in need thereof, comprising administering to the mammal an effective amount of any one or more of the compositions described herein.

The present disclosure also provides compositions described herein for use in preparation of a medicament for preventing pancreatic beta cell degeneration in a mammal in need thereof, comprising administering to the mammal an effective amount of any one or more of the compositions described herein.

In order that the subject matter disclosed herein may be more efficiently understood, examples are provided below. It should be understood that these examples are for illustrative purposes only and are not to be construed as limiting the claimed subject matter in any manner. Throughout these examples, molecular cloning reactions, and other standard recombinant DNA techniques, were carried out according to methods described in Maniatis et al., Molecular Cloning—A Laboratory Manual, 2nd ed., Cold Spring Harbor Press (1989), using commercially available reagents, except where otherwise noted.

EXAMPLES

Example 1: Progressive Reduction in Fasting Glucose

Figure 2:
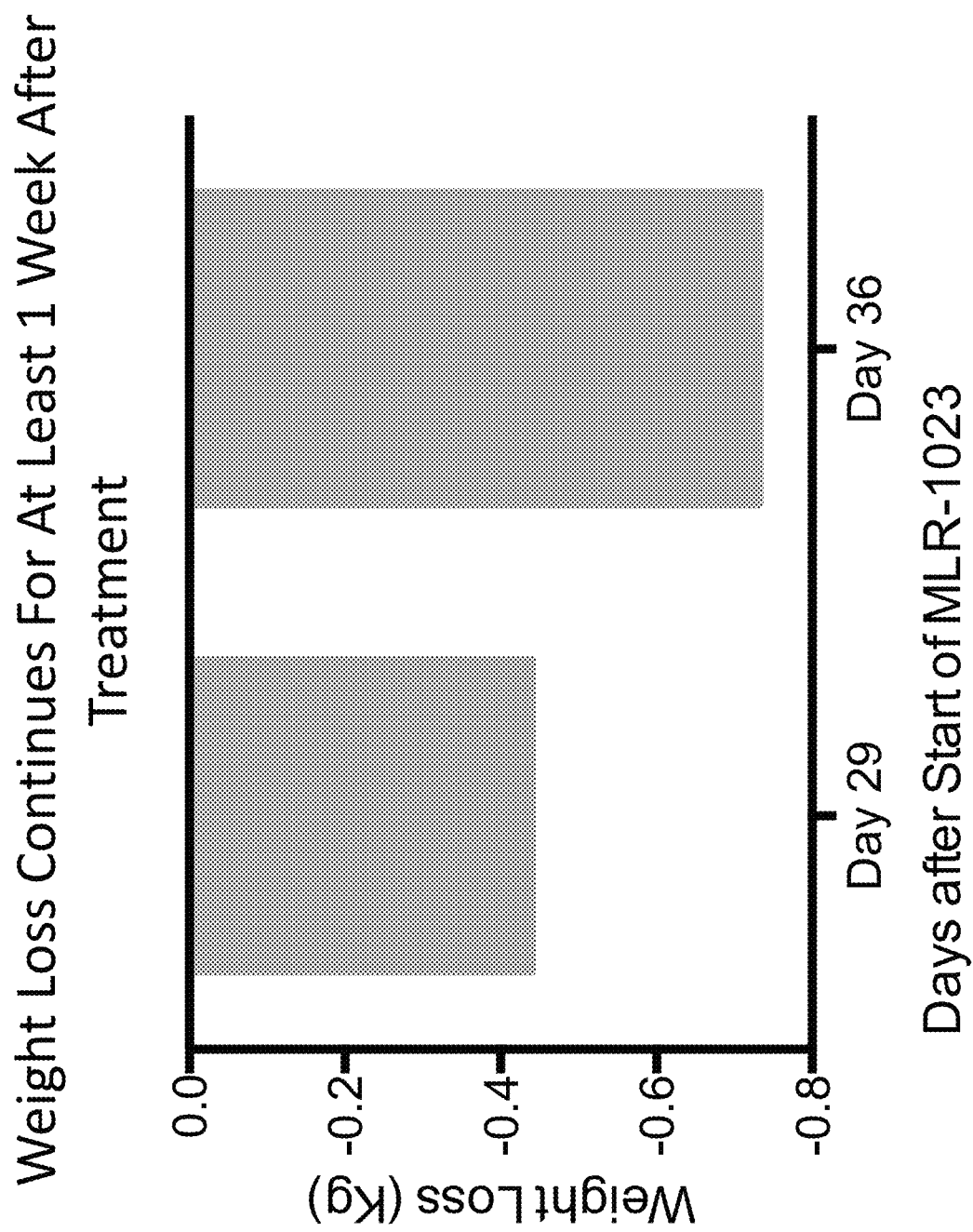
FIG. 2 shows continued weight loss 1 week after treatment with Compound 102.

This Phase 2a clinical trial was conducted in the U.S. (103 subjects) and Korea (27 subjects). Subjects were 18-75 years of age, possessed BMIs of 20-40 kg/m$^2$, possessed glycosylated HbA1c of 7-10%, were either metformin-naive or washed off of metformin, and were not exposed to other anti-diabetic agents within the previous 6 months. Subjects were treated with one of four active doses (100 mg once-daily (qd), 100 mg twice-daily (bid), 200 mg qd, or 200 mg bid) of Compound 102 or placebo for 4 weeks after having 3 weeks of placebo run-in. FIG. 1 shows the progressive reduction in fasting plasma glucose (FPG). Body weights, as secondary endpoints, were measured at Day 1 and Day 29 and at the follow-up visit 1 week after treatment stopped, at Day 35. This study revealed statistically significant improvements in body weight loss over the 4-week treatment period. In general, all treatment groups exhibited some degree of weight loss at Day 29 even when they were not significant. Also, all groups except for the 200 mg bid group showed continued loss 1 week after treatment (Day 35) compared to Day 29 (see, FIG. 2). The effect was most pronounced in the U.S. subjects and in the 100 qd dose group.

The fact that weight loss continued for at least 1 week after treatment was terminated, at a time when drug has long since left the body, is consistent with a mechanism whereby Compound 102 transforms white adipose tissue to "beige" adipose tissue, which is able to burn energy and effect weight loss. The transformed state of tissue type would be expected to last longer than the presence of the drug.

Example 2: Compound 102 Induces Beige Adipocyte Gene Expression

Human adipocyte precursor cells isolated from subcutaneous abdominal fat were purchased from LaCell, LLC, New Orleans, La. Cells were seeded and grown to confluence in DMEM/F12 with 10% heat inactivated FBS. Differentiation to mature adipocytes was induced in medium composed of 70% DMEM and 30% DMEMF12 supplemented with 3% FBS, 1 μM dexamethasone (Sigma D4902), 33 μM biotin (Sigma B4639), 100 nM insulin (Sigma I5500), 20 μM pantothenate (Sigma P5155), 5 μM rosiglitazone (AK Scientific F325) and 500 NM IBMX (Sigma 15879) for four days. Cells were maintained in medium composed of 70% DMEM and 30% DMEMF12 supplemented with 3% FBS, 1 μM dexamethasone, 33 μM biotin, 100 nM insulin, and 20 NM pantothenate for seven days before experimental treatment.

A solution of 10 mM Compound 102 was prepared in DMSO and diluted to 60 μM or 30 μM in maintenance medium without dexamethasone for cell treatment. In some experiments, cells were treated with 20 μM menthol (Sigma M2772).

Total RNA was isolated from adipocyte cultures grown in 12-well plates using Trizol and Qiagen RNAeasy kits. Reverse transcriptase and PCR were conducted in one reaction with the reverse PCR primer priming cDNA synthesis using SuperScript® III Platinum® One-Step Quantitative RT-PCR System with Rox from Invitrogen (11745). Predesigned Taqman primer-probe sets were purchased from Applied Biosystems for the following human transcript sequences: UCP1 (Hs249211), PPARGC1α (HS527078), PPARU (Hs103110), CPT1b (Hs439777), and GLUT4/SLC2A4 (Hs380691). Aplicons were designed to span an intron-exon junction to avoid amplification of genomic sequences. Each sample RT-PCR assay was conducted in duplicate.

Figure 3:
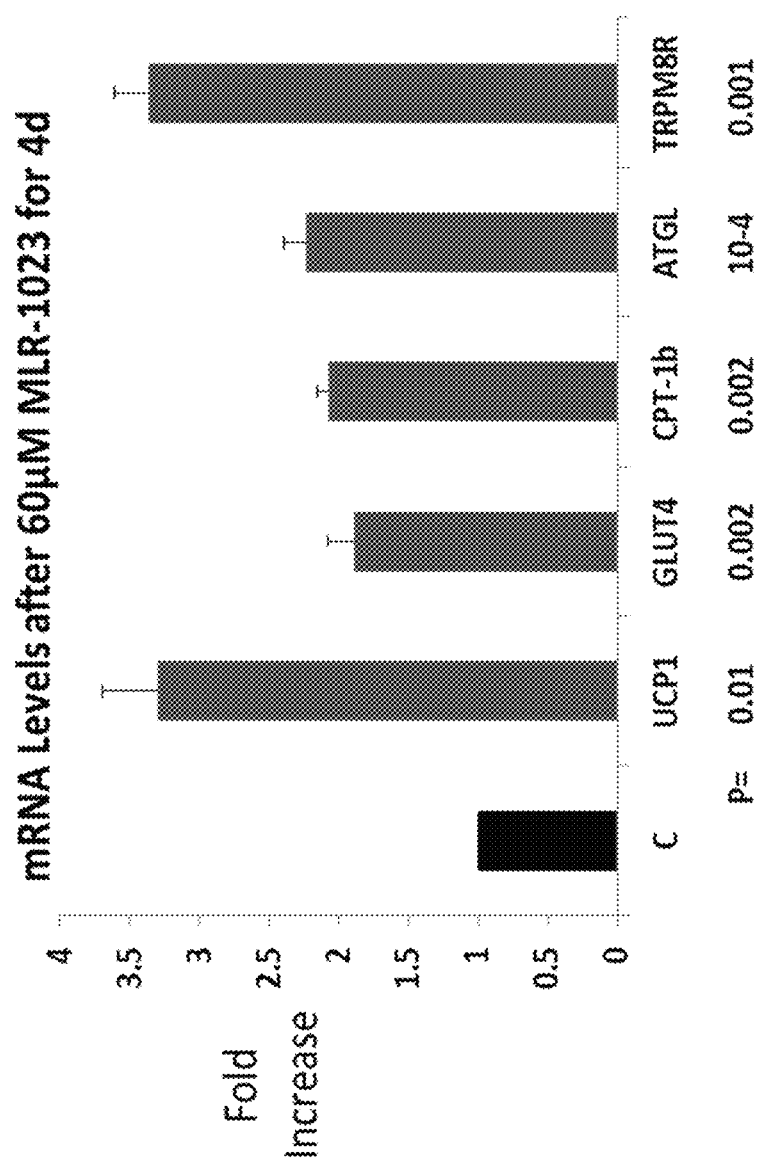
FIG. 3 shows human adipocytes treated with Compound 102 experienced significant increases, at day 4, in the expression of several genes associated with the beiging of white adipose tissue.

As depicted in FIG. 3, human adipocytes treated with Compound 102 experienced significant increases, at day 4, in the expression of several genes associated with the beiging of white adipose tissue: 1) UCP-1, which triggers mitochondrial fat oxidation and is associated with the differentiation of white adipocytes into beige adipocytes; 2) GLUT4, which increases glucose utilization and can be seen as a result of "beiging"; 3) Carnitine palmitoyltransferase-Ib (CPT-1b), which is induced during "beiging" and involved in the oxidization of fat in mitochondria; 4) Adipose Triglyceride Lipase (ATGL), the rate limiting enzyme for lipolysis; and 5) Transient Potential Melastatin 8 Receptor (TRPM8R).

Figure 4:
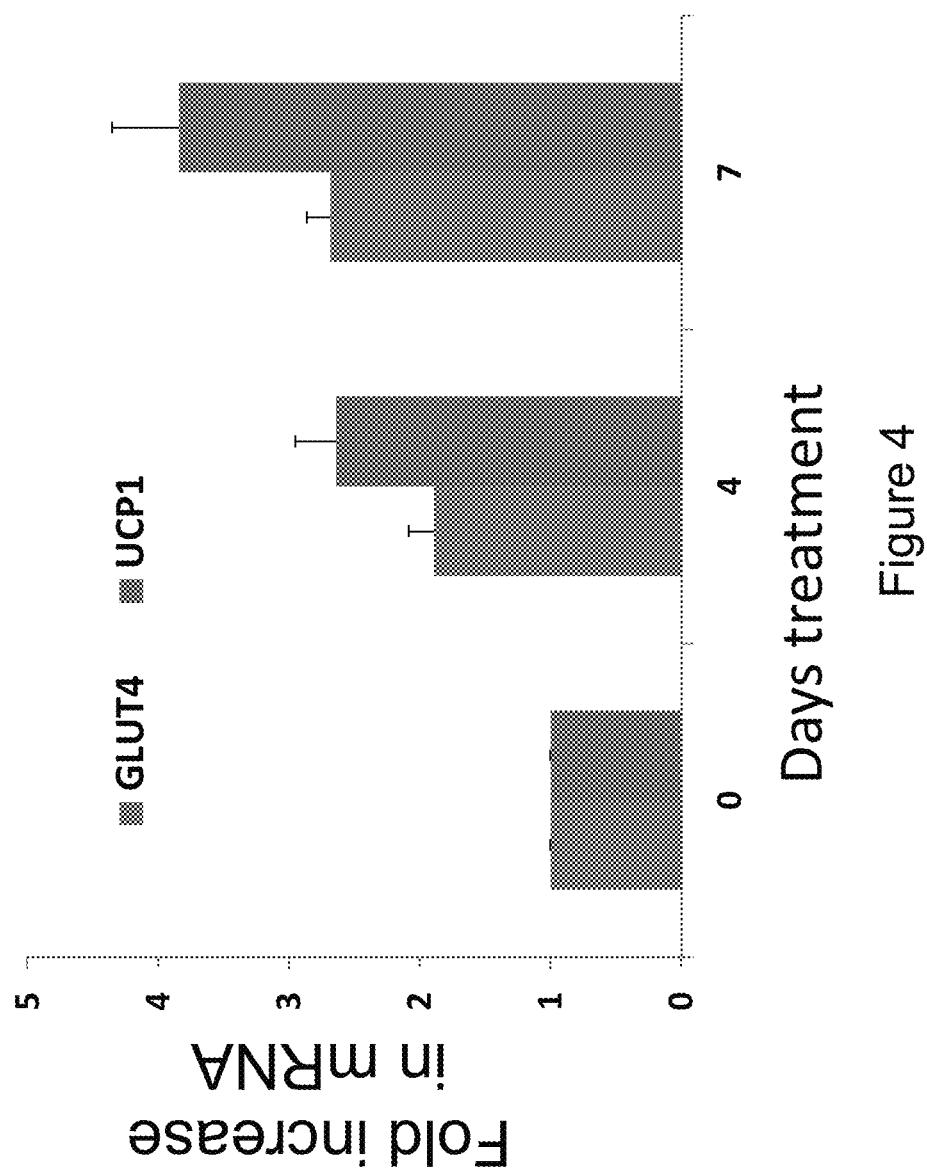
FIG. 4 shows continued to increase of beige adipose tissue GLUT4 rRNA and UCP1 mRNA over a 7-day treatment period in primary cultured human adipocytes.

As depicted in FIG. 4, markers of beige adipose tissue GLUT4 rRNA and UCP1 mRNA continued to increase over the 7-day treatment period in primary cultured human adipocytes.

Figure 5:
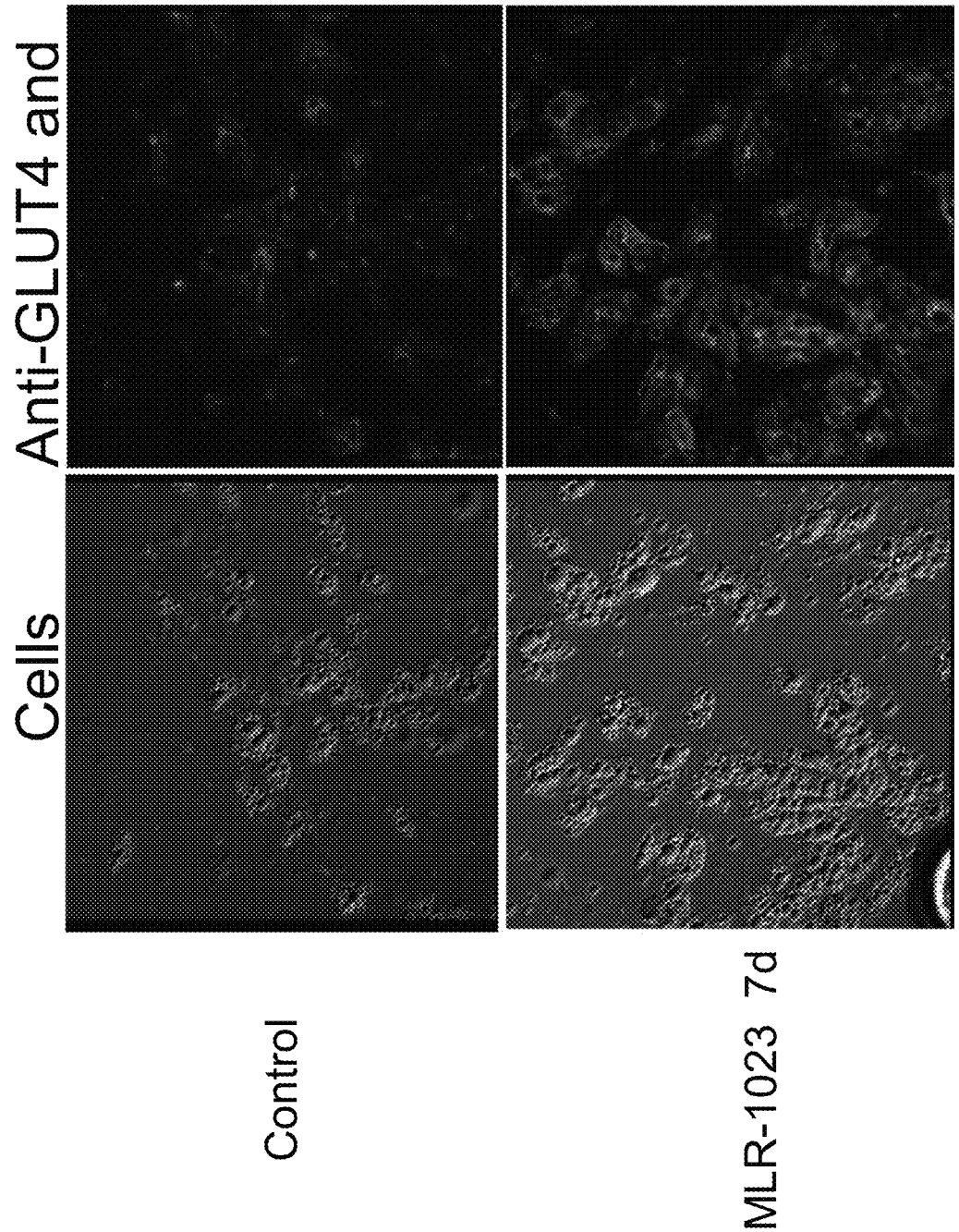
FIG. 5 shows continued expression of GLUT4 protein over a 7-day treatment period in primary cultured human adipocytes (40× magnification).

As depicted in FIG. 5, expression of GLUT4 protein continued to exist over the 7-day treatment period in primary cultured human adipocytes.

Figure 6:
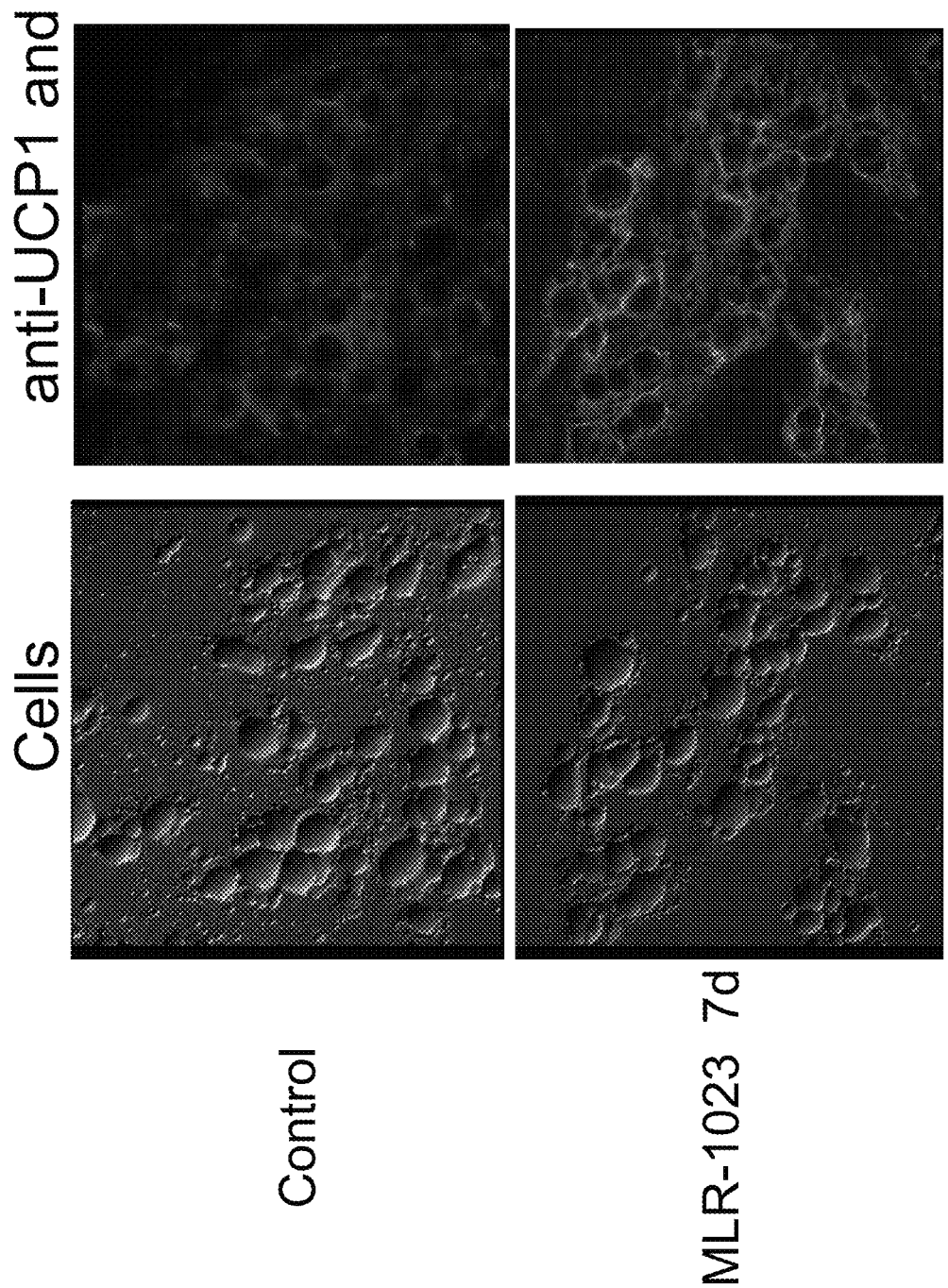
FIG. 6 shows continued expression of UCP1 protein over a 7-day treatment period in primary cultured human adipocytes (40× magnification).

As depicted in FIG. 6, expression of UCP1 protein continued to exist over the 7-day treatment period in primary cultured human adipocytes.

Figure 7:
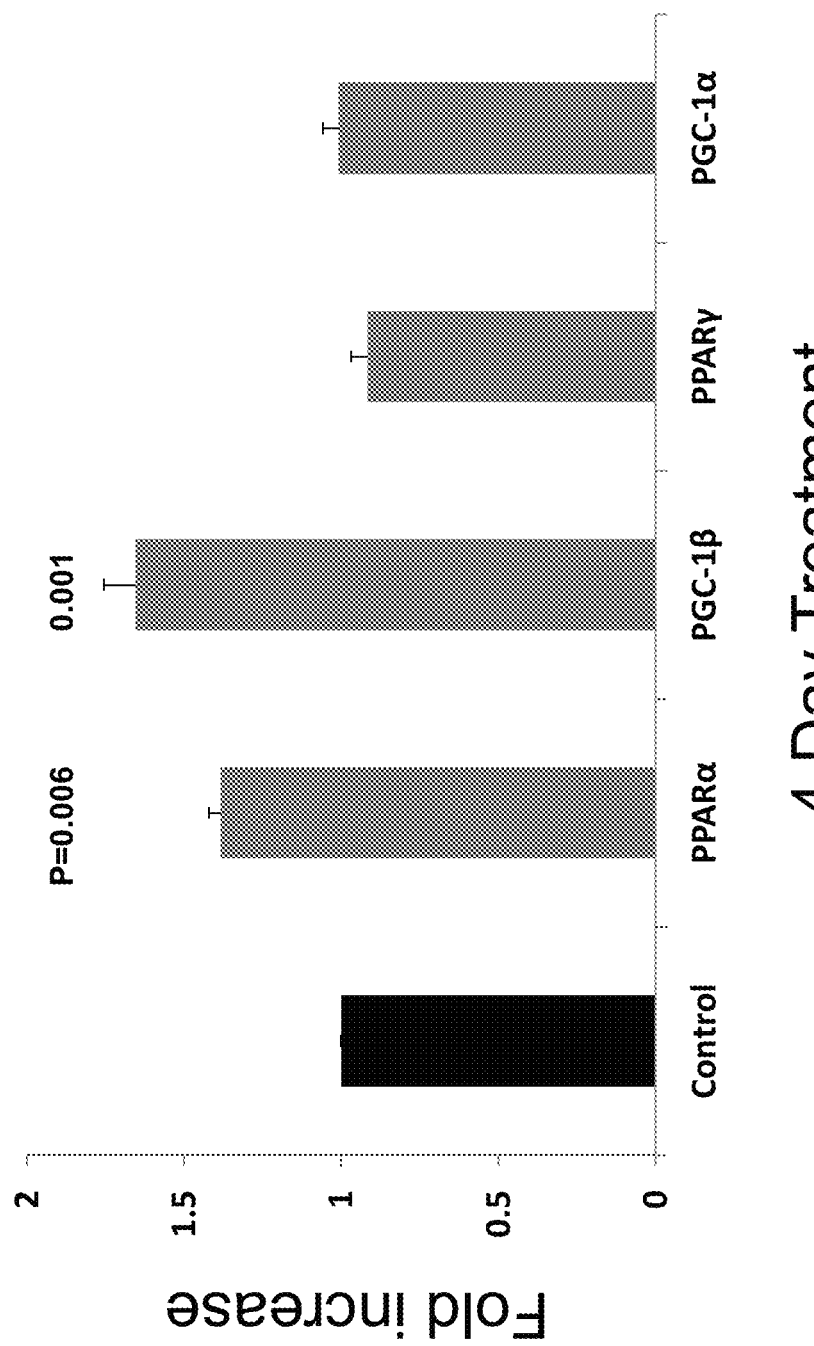
FIG. 7 shows induction of UCP1 Activators, PPARα and PGC-10, by treatment with Compound 102.

As depicted in FIG. 7, Compound 102 induced the expression of the UCP1 activators PPARα and PGC-10.

Figure 8:
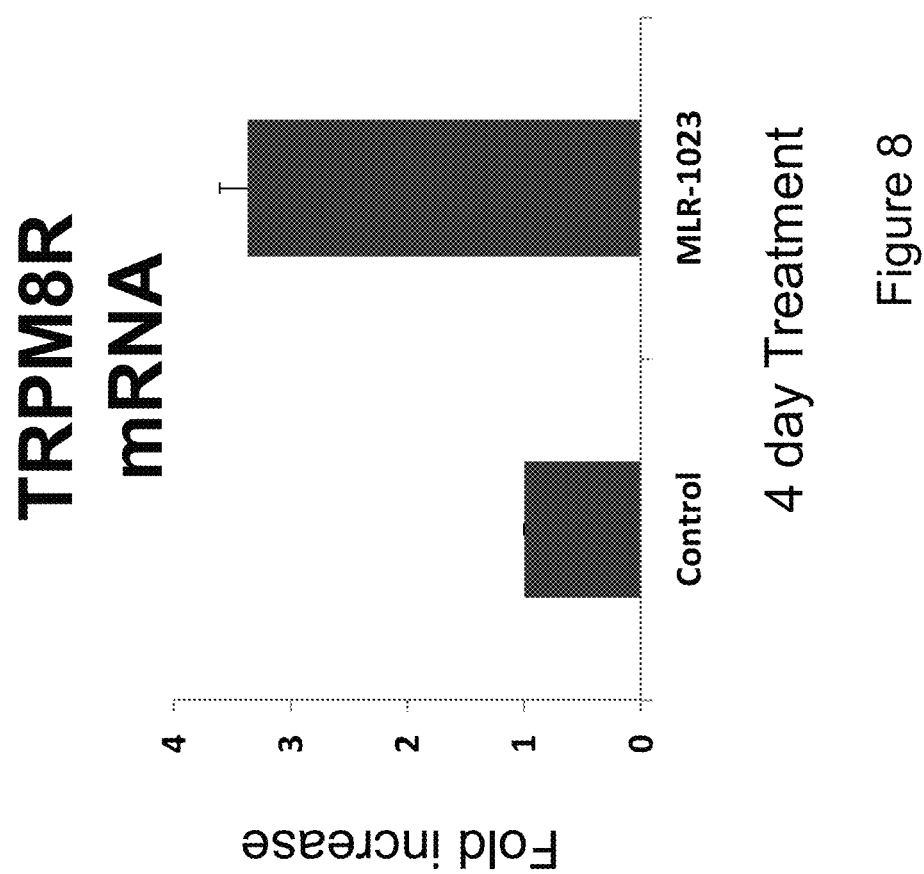
FIG. 8 shows induced expression of TRPM8 menthol receptor mRNA by treatment with Compound 102.

As depicted in FIG. 8, Compound 102 induced the expression of TRPM8 menthol receptor mRNA.

Figure 9:
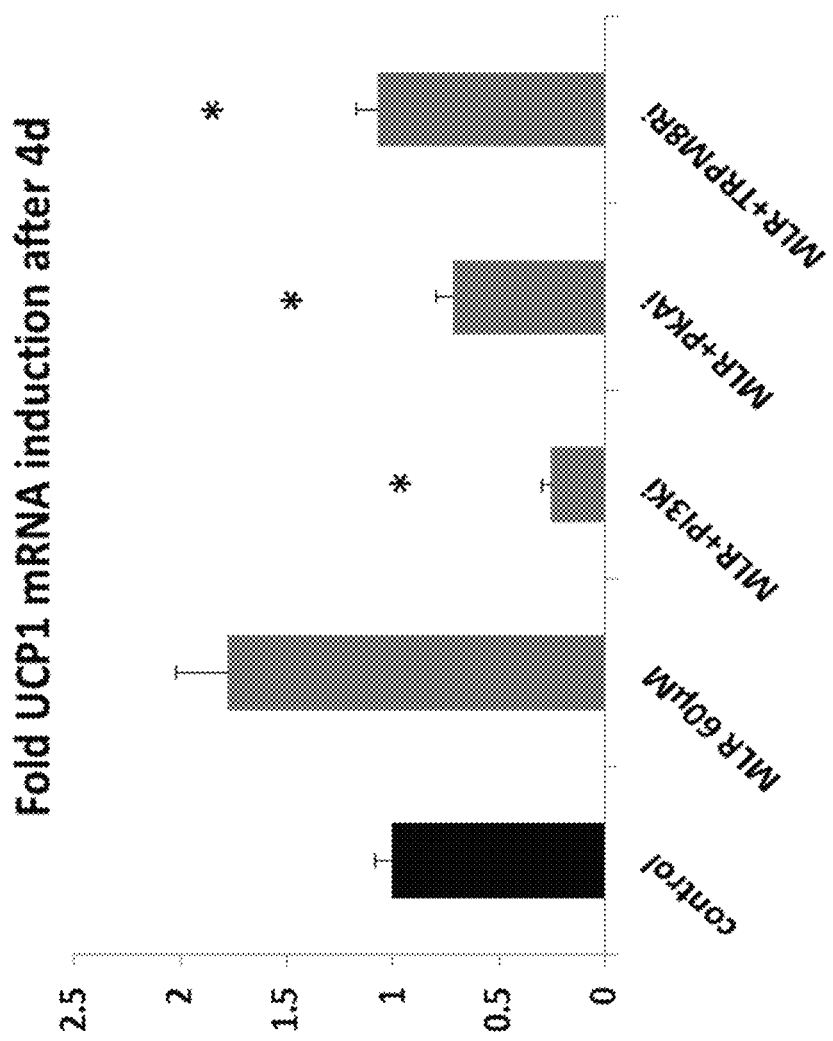
FIG. 9 shows the reduction of Compound 102-induced UCP1 levels by PI3Ki, PKAi, and TRPM8Ri.

Compound 102 is an activator of the IRS1/PI3 kinase pathway (PI3K). PI3K produces PIP2, a membrane phospholipid that is required for activity of the TRPM8 receptor. The following inhibitors were used to determine their effect on lowering Compound 102-induced UCP1 expression over 4 days: 1) a specific PI3K inhibitor, LY294002 (20 µM), 2) a PKA inhibitor, H89 (20 µM), and 3) a TRPM8R inhibitor, PBMC (20 nM). All three inhibitors reduced UCP1 mRNA to levels of unstimulated controls or lower (see, FIG. 9). These results indicate that PI3K activity, PKA activity, and TRPM8 receptor activity are required for UCP1 expression after treatment with Compound 102.

Figure 10:
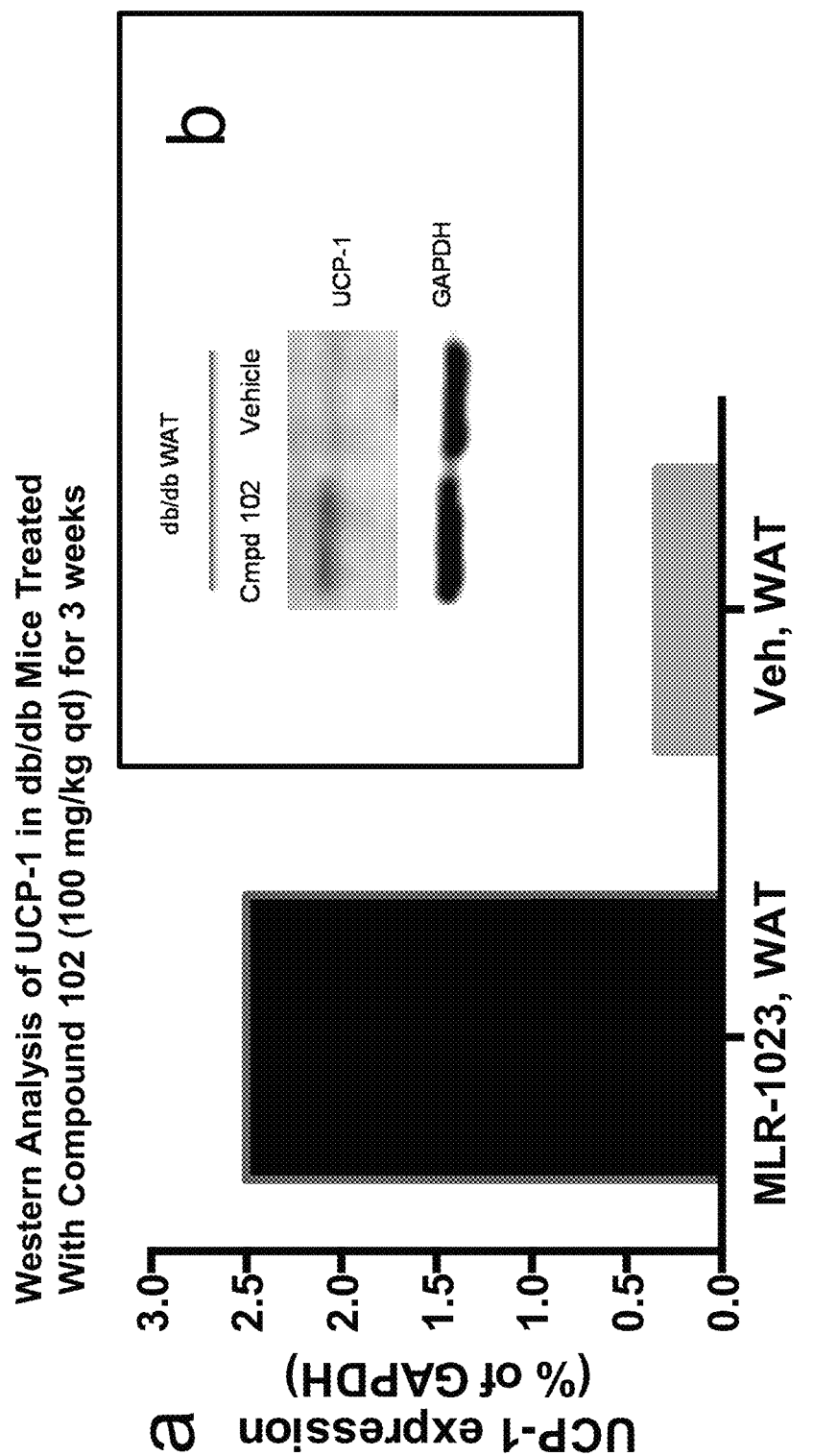
FIG. 10 (panel a) shows densitometry quantitation for levels of UCP-1 adipose tissue protein observed in db/db mice treated for 3 weeks with Compound 102 (100 mg/kg qd)

Increased levels of UCP-1 adipose tissue protein was observed in db/db mice treated for 3 weeks with Compound 102 (100 mg/kg qd). Adipose tissue was collected 4 hours after the last dose of Compound 102. Densitometry quantitation from 4 separate experiments was performed to obtain the values shown in FIG. 10 (panel a). A representative Western blot from 4 separate experiments conducted is shown in FIG. 10 (panel b). In agreement with the increased levels of UCP-1 mRNA and protein observed in primary human adipocytes, increased levels of UCP-1 protein in mice treated with Compound 102 was also observed.

Figure 11:
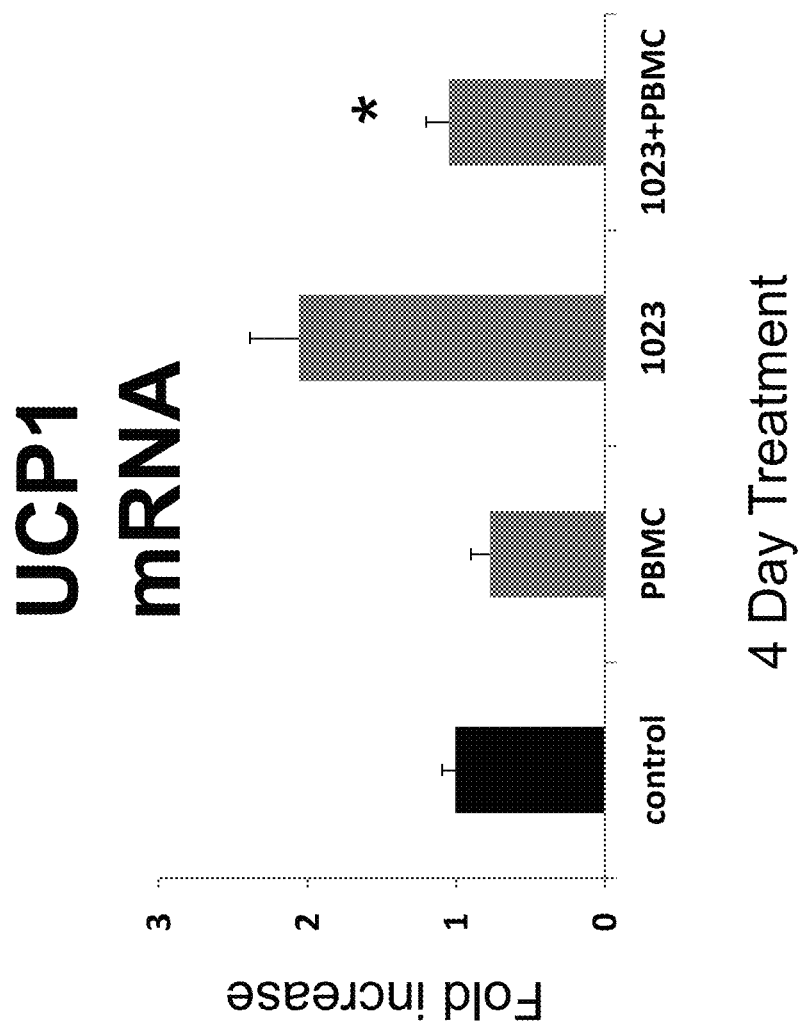
FIG. 11 shows blocking of Compound 102-induction of UCP-1 with a TRPM8 inhibitor.

As depicted in FIG. 11, a TRPM8 inhibitor blocked Compound 102-induction of UCP-1, demonstrating that lyn kinase activation induces UCP-1 via the action of TRPM8.

Figure 12:
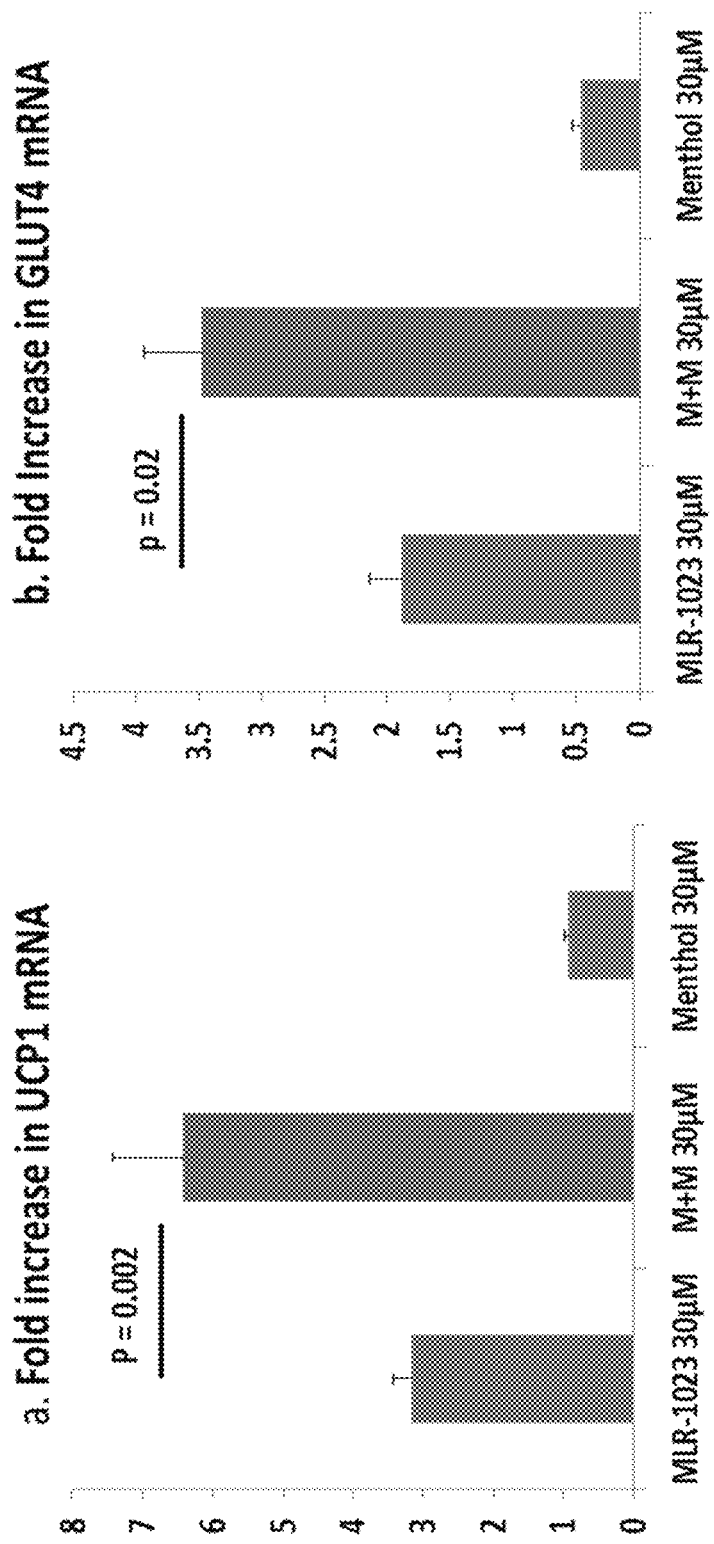
FIG. 12 (panels a and b) shows that menthol by itself does not induce "beiging" effects but, rather, potentiates the induction of beiging by Compound 102 in cultured primary human adipocytes.

The ability of menthol and Compound 102 to induce UCP1 in adipocytes was also examined. Treatment with 30 µM menthol (serum $C_{max}$) and 30 NM Compound 102 together synergitically elevated UCP1 expression over levels stimulated by Compound 102 alone in a 7 day treatment (see, FIG. 12, panel a). Menthol alone did not induce expression. A similar increase was observed in GLUT4 expression when menthol was added to Compound 102 (see, FIG. 12, panel b). Menthol doubles the induction of UCP1 and GLUT4 by Compound 102.

As depicted in FIG. 13, menthol by itself does effect insulin sensitization or glycemic control in a rodent oral glucose tolerance test. In contrast, menthol potentiates the the insulin sensitizing action of Compound 102 in a rodent oral glucose tolerance test.

Various modifications of the described subject matter, in addition to those described herein, will be apparent to those skilled in the art from the foregoing description. Such modifications are also intended to fall within the scope of the appended claims. Each reference (including, but not limited to, journal articles, U.S. and non-U.S. patents, patent application publications, international patent application publications, gene bank accession numbers, and the like) cited in the present application is incorporated herein by reference in its entirety.

What is claimed is:

1. A method of treating hypertension, coronary heart disease, diabetic neuropathy, lipodystrophy, or pancreatitis in a mammal in need thereof, comprising administering to the mammal an effective amount of a lyn kinase activator and a TRPM8 agonist;
   wherein the lyn kinase activator is of formula:

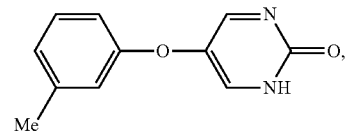 [SMILES: Cc1cccc(Oc2cnc(=O)[nH]c2)c1]

or a pharmaceutically acceptable salt thereof; and
   the TRPM8 agonist is menthol.

2. The method of claim 1, wherein the lyn kinase activator and TRPM8 agonist are present in the same composition.

3. A method of treating hypertension, coronary heart disease, diabetic neuropathy, or lipodystrophy, in a mammal in need thereof, comprising administering to the mammal an effective amount of a lyn kinase activator and a TRPM8 agonist;
   wherein the lyn kinase activator is of formula:

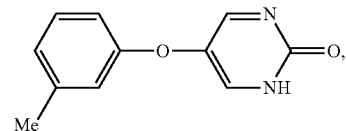 [SMILES: Cc1cccc(Oc2cnc(=O)[nH]c2)c1]

or a pharmaceutically acceptable salt thereof; and
   the TRPM8 agonist is menthol.

4. The method of claim 3, wherein the lyn kinase activator and TRPM8 agonist are present in the same composition.

* * * * *